(12) United States Patent
Sutton et al.

(10) Patent No.: US 8,629,254 B2
(45) Date of Patent: Jan. 14, 2014

(54) BORON TRANSPORTER

(75) Inventors: Tim Sutton, Stirling (AU); Ute Baumann, Myrtle Bank (AU); Julie Hayes, Crafers West (AU); Peter Langridge, Teringie (AU)

(73) Assignee: Australian Centre for Plant Functional Genomics PTY Ltd., South Australia (AU)

( * ) Notice: Subject to any disclaimer, the term of this patent is extended or adjusted under 35 U.S.C. 154(b) by 668 days.

(21) Appl. No.: 12/522,673

(22) PCT Filed: Jan. 11, 2008

(86) PCT No.: PCT/AU2008/000018
§ 371 (c)(1),
(2), (4) Date: Jul. 14, 2010

(87) PCT Pub. No.: WO2008/083441
PCT Pub. Date: Jul. 17, 2008

(65) Prior Publication Data
US 2010/0281583 A1 Nov. 4, 2010

(30) Foreign Application Priority Data

Jan. 12, 2007 (AU) ............................... 2007900157

(51) Int. Cl.
*C07K 14/415* (2006.01)
*C12N 15/09* (2006.01)
*C12N 15/62* (2006.01)
*C12N 15/63* (2006.01)
*C12N 15/82* (2006.01)

(52) U.S. Cl.
USPC ......... 536/23.1; 536/23.6; 800/295; 800/298; 800/278; 435/320.1

(58) Field of Classification Search
None
See application file for complete search history.

(56) References Cited

U.S. PATENT DOCUMENTS 7,569,389 B2 * 8/2009 Feldmann et al. ............ 435/468

FOREIGN PATENT DOCUMENTS

| JP | 2005185101 | * | 7/2005 | ............ C12N 15/09 |
| JP | 2005253430 | * | 9/2005 | ............ C12N 15/09 |

OTHER PUBLICATIONS

Maniatis T et al. Molecular Cloning. A Laboratory Manual. 1982. pp. 387-389.*
Guo HH. Protein tolerance to random amino acid change. PNAS. 101(25): 9205-9210.*
Kennell DE. Principles and practices of nucleic acid hybridization. Progress in Nucleic Acid Research and Molecular Biology. 1971(11), pp. 259-301.*
Kasai K. High Boron-induced ubiquitination regulates vacuolar sorting of the BOR1 borate transporter in *Arabidopsis thaliana*. The Journal of Biologcal Chemistry. 2011. 286(8): 6175-6183.*
Tingay et al. *Agrobacterium tumefaciens*-mediated barley transformation. The Plant Journal. 1997. 11(6), 1369-1376.*
Miwa et al. Improvement of seed yields under boron limiting conditions through overexpression of BOR1, a boron transporter for xylem loading, in *Arabidopsis thaliana*. The Plant Journal. 2006. 46: 1084-1091.*
Hayes, J., et al., "Boron Tolerance in Barley is Mediated by Efflux of Boron from the Roots," *Plant Physiology*, vol. 136(2), pp. 3376-3382 (Oct. 2004).
Hedley, P., et al., "EBma08_SQ004_J05_R maternal, 28 DPA, no treatment, cv Optic, EBma08 Hordeum vulgare subsp. Vulgare cDNA clone EBma08_SQ004_J05 5', mRNA sequence," Database Genbank, Database Accession No. BM371977, 2 pgs. (Jul. 23, 2002).
Miwa, K., et al., "Improvement of seed yields under boron-limiting conditions through overexpression of BOR1, a boron transporter for xylem loading, in *Arabidopsis thaliana*," The Plant Journal, vol. 46(6), pp. 1084-1091 (2006).
Nozawa, A., et al., "Roles of BOR1, DUR3, and FBS1 in boron transport and tolerance in *Saccharomyces cerevisiae*," FEMS Microbiology Letters, vol. 262(2), pp. 216-222 (2006).
Park, M., et al., "NaBC1 Is a Ubiquitous Electrogenic Na$_+$—Coupled Borate Transporter Essential for Cellular Boron Homeostasis and Cell Growth and Proliferation," *Molecular Cell*, vol. 16(3), pp. 331-341 (Nov. 5, 2004).
Sasaki, T., et al., "*Oryza sativa*(japonica cultivar-group) genomic DNA, chromosome 1, PAC clone: P0013F10," Database Genbank, Database Accession No. AP002523, 40 pgs. (Jan. 19, 2005).
Sasaki, T., et al., "Band 3 anion transport protein—like [*Oryza sativa* Japonica Group]," gENpEPT Accession No. BAD67809, 2 pgs. (Feb. 16, 2008).
Sato, K., et al., "BJ473417 K. Sato unpublished cDNA library, cv. Haruna Nijo adult, heading stage top three leaves *Hordeum vulgare* subsp. Vulgare cDNA clone baal12f24 3-,mRNA sequence," Database Genebank, Database assession No. BJ473417, 2 pgs. (May 23, 2002).
Takano, J., et al., "*Arabidopsis* boron transporter for xylem loading," *Nature*, vol. 420(6913), pp. 337-340 (2002).
Yokoi, K.N., et al., "*Oryza sativa* (japonica cultivar-group) boron transporter (BOR2) mRNA, complete cds," Database Genbank, Database Accession No. DQ421408, 2 pgs. (Mar. 21, 2006).

(Continued)

*Primary Examiner* — Cathy Kingdon Worley
*Assistant Examiner* — Ashley K Buran
(74) *Attorney, Agent, or Firm* — Klarquist Sparkman, LLP

(57) ABSTRACT

The present invention relates to boron transporters and, in particular, to boron transporters derived from plants. The present invention also relates to methods that utilize boron transporters, such as methods for modulating boron transport in cells and methods for determining the level or rate of boron transport in a cell or organism on the basis of the expression level of one or more boron transporters.

15 Claims, 14 Drawing Sheets

(56) References Cited

OTHER PUBLICATIONS

Figure 1:
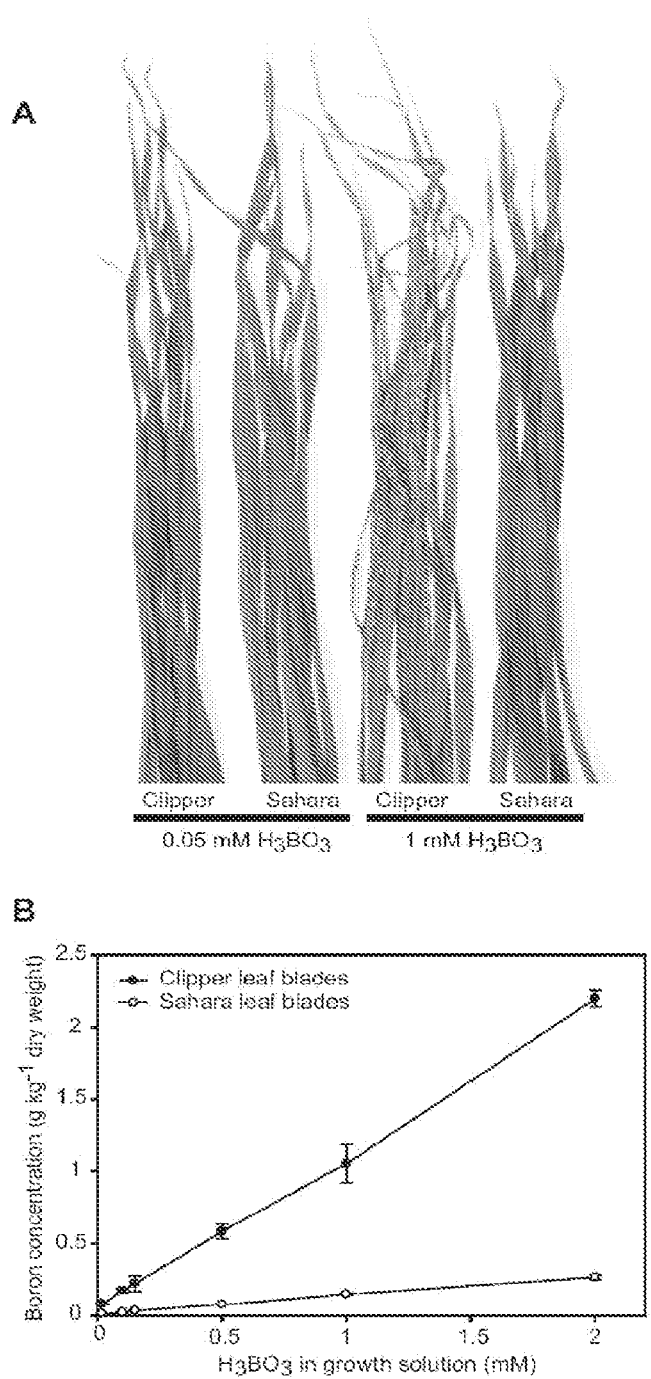

Yokoi, K.N., et al., "*Oryza sativa* (japonica cultivar-group) boron transporter (BOR4) mRNA, complete cds," Database Genbank, Database Accession No. DQ421409, 2 pgs. (Mar. 21, 2006).

Database GQPAT—GenomeQuest, sequence identifier JP2005253430-0010, JP2005253430 (Japan Science and Technology Agency), 2 pgs. (Sep. 22, 2005).

* cited by examiner

FIG. 11A

```
                     1                                                50
        Bot1     (1) -----MDLLRNPPKGVVADVKGRAPWYKDDWLAGLRACEG---------I
  Os12g37840.1   (1) -----MEESFVPLRGIKNDLHGRLQCYKQDWTGGFRACIR---------I
    Os01g08040   (1) -----MDLLRTPPKGVVADIEGRVAWYKHDVVAGFRSCFR---------I
    Os01g08020   (1) -----MELLKIPPKGVVADIEGRAAWYKHDWLEGFHSCFR---------I
    Os05g08430   (1) ----MTGTVKAPPEGVVNDFKGRLSCYKQDWIDGFRTCFR---------I
   At2g47160.1   (1) -----MEETFVPPEGIKNDLKGRLMCYKQDWTGGFKACFR---------I
   At3g62270.1   (1) -----MEETFVPPEGIKNDLKGRLMCYKQDWTGGIKACFR---------I
   At3g06450.1   (1) ---MDEAESFVPPQGIKKDVKGRLNCYKQDWISGLRACFR---------I
   At1g15460.1   (1) MEERVDSSKRLFRGIVADLRGRALCYKEDWVAGLRSCFG---------I
   At1g74810.1   (1) MEERVEGSKRPPQGIIRDVKGRALCYKQDWIAGLRSCFG---------I
   At5g25430.1   (1) ---MKSEGESGPPQGILRDIEGRRKCYKQDWIRGIKTCG-----------
   At4g32510.1   (1) -----MEGVKFPPGIINDFNGRRKCYKQDWLAAFNSCVRYYTLFMLFSI
                     51                                               100
        Bot1    (37) LAPTMYIFFASALPVIAFGEQLSNETNG-ILSIVETLASTAICGIIHAIL
  Os12g37840.1  (37) LAPTTYIFFASAIPVISFGEQLERNIDG-VLTAVQTLASTALCGIIHSFL
    Os01g08040  (37) LAPTMYIFFASALPVIAFGAQLSRETNG-ILTIVETLASTALCGIIHSIL
    Os01g08020  (37) LAPTMYIFFASALPVIAFGTQLSRETNG-ILTTVETLASTAICGIIHSIL
    Os05g08430  (38) LAPTLYIFFASALPVVAFGEQLSNDTDG-ALTIVETLASTAICGIIHSIL
   At2g47160.1  (37) LAPTTYIFFASAIPVISFGEQLERSTDG-VLTAVQTLASTAICGMIHSII
   At3g62270.1  (37) LAPTTYIFFASAIPVISFGEQLERSTDG-VLTAVQTLASTAICGIIHSII
   At3g06450.1  (39) LAPTTYIFFASAIPVITFGEQLERDTDG-KITAVQTLVSTALCGVIHSII
   At1g15460.1  (42) LAPTTYIFFASALPVIAFGEQLSRDTEG-ALSTVETLASTALCGVIHSIL
   At1g74810.1  (42) LAPTTYVFFASALPVIAFGEQLSHDTER-SLSTVETLSTALCGVIHSLL
   At5g25430.1  (37) ----------------------------ALSAVETLASTSICGIIHAIF
   At4g32510.1  (46) LAPTLYIFIASALPVIAFGEQLSRETGDRYLGIAESLASTALCGIIHSVF
                     101                                              150
        Bot1    (86) GGQPMMIVGVAEPTIIMYTYLYNFAKKQPGLGERLYLAWAGWVCIWTAIM
  Os12g37840.1  (86) GGQPLLILGVAEPTVLMYTFMFNFAKDRPDLGRRLFLAWTGWVCVWTAIL
    Os01g08040  (86) GGQPLLIVGVAEPTIIMYTYLYNFAKNQQALGERLYLAWAGWVCIWTALM
    Os01g08020  (86) GGQPLLIVGVAEPTIIMYTYLYNFAKNQQALGERLYLAWAGWVCIWTAIM
    Os05g08430  (87) GGQPLLIVGVAEPTIIMYTYIYNFAKNHPNLGERLFLPWAGWVCIWTAFM
   At2g47160.1  (86) GGQPLLILGVAEPTVIMYTFMFNFAKARPELGRDLFLAWSGWVCVWTALM
   At3g62270.1  (86) GGQPLLILGVAEPTVIMYTFMFNFAKGRPELGRNLFLAWSGWVCVWTSLI
   At3g06450.1  (88) GGQPLLILGVAEPTVIMYTFMFNFAKSRTDLGSNLFLAWTGWVCLWTGLL
   At1g15460.1  (91) GGQPLLILGVAEPTVLMYVYLYNFAIGRPELGKQLYLAWAAWVCWTALL
   At1g74810.1  (91) GGQPLLILGVAEPTVLMYKYLYDFAKGRPELGKQLYLAWVAWVCVWTALL
   At5g25430.1  (58) GGQPLLIVGVAEPTIIMYTYLYSFCISRPDIGRELYLAWVAWVCWTSVL
   At4g32510.1  (96) GGQPLLIVGVAEPTIIMYTYLHSFSKSRPELGQKLYLAWAGWVCVWTAVL
                     151                                              200
        Bot1   (136) LFLLAMFNASNVISRFTRVAGELFGMLITVLFLQEAIKG-------IVGE
  Os12g37840.1 (136) LFLLAILGACSIINRFTRIAGELFGLLIAMLFMQQAIKG-------LVDE
    Os01g08040 (136) LFLLAMFNASNVISRFTRVAGELFGMLITVLFLQQAIKG-------IIEE
    Os01g08020 (136) LFLLAMFNASNVISRFTRVAGELFGMLITVLFLQQAIKG-------IIEE
    Os05g08430 (137) LFLMAMFNAAVVINRFTRFAGELFGMLITILFMQEAVKG-------MLGE
   At2g47160.1 (136) LFVLAICGACSIINRFTRVAGELFGMLIAMLFMQQAIKG-------LVDE
   At3g62270.1 (136) LFVLAICGACSFINRFTRVAGELFGMLIAMLFMQQAIKG-------LVDE
   At3g06450.1 (138) LFLLAVLGACTFINRFTRLAGELFGILIAMLFMQEAIRG-------IVDE
   At1g15460.1 (141) LFVMAILNTADIINRFTRVAGELFGMLISVLFIQQAIKG-------MVSE
   At1g74810.1 (141) LFLMAIFNMAYIINRFTRIAGELFGMLIAVLFLQQTIKG-------MVSE
   At5g25430.1 (108) LILLSIFNAGTIITRFTRIAGELFGMLIAVLFLQEAIK------G-LISE
   At4g32510.1 (146) LMLLAMLNACNIISRFTRIAGELFGMLITVLFIQEAVKVVMGIYMGLIGE
```

FIG. 11B

```
                        201                                                250
          Bot1   (179)  FSMPKDAEIFDRSSPIYQFQWIYVNGLLGVIFSIGLYYSALKTRRARSNL
   Os12g37840.1  (179)  FRIPER---ENRKALEFVSSWRFANGMFAIVLSFGLLLTALRSRKARSNR
      Os01g08040 (179)  FKVPRD---ADHSSPIYQFQWLYVNGLLGVIFSIGLYTALRSRRAPSNV
      Os01g08020 (179)  FKVPGG---VDHSSPIYRFQWLYVNGLLGVIFSIGLYYTALRSRRAPSNV
      Os05g08430 (180)  FSVPEG---KDHSLPIYQFQWAYVNGLLGIIFSMGLYTAIRSRSARSSL
    At2g47160.1 (179)   FRIPER---ENQKLKEFLPSWRFANGMFALVLSFGLLLTGLRSRKARSNR
    At3g62270.1 (179)   FRAPAR---EDLKLVEFLPSWRFANGMFALVLSFGLLITALRSRKARSNR
    At3g06450.1 (181)   FGVPGR---TNPRSAEFQPAWVFANGMFGLVLSSGLYTGLKSRKARSNR
    At1g15460.1 (184)   FGMPKD---EDSKLEKYKFEWLYTNGLLGLIFTFGLLYTALKSRKARSNR
    At1g74810.1 (184)   FRIPKG---EDSKLEKYQFEWLYTNGLLGLIFTVGLVYTALKSRKARSNP
    At5g25430.1 (151)   FHAPEI---KNQEGKSHFLLIYANGLLAVIFSLGLLITALKSRRAKSNK
    At4g32510.1 (196)   FLVPKS---DDPSLEVYQFQWRYTNGLLAVIFSFGLYTALKSRRAPSNK
                        251                                                300
          Bot1   (229)  YGIGWLRSFIADYGVPLMVIVWTAFSYALPSGVPSGVPRRLFSPLPWESS
   Os12g37840.1  (226)  YGIGWLRGFIADYGVPLMVLVWTGVSYIPYGSVPKGIPRRLFSPNPWSPG
      Os01g08040 (226)  YGQGWLRGFIADYGVPLMVIVWTAFSYTLPKDVPSGVPRRLFSPLPWESS
      Os01g08020 (226)  YGQGWLRGFISDYGVPLMVIVWTALSYALPKDVPSGVPRRLFSPLPWESS
      Os05g08430 (227)  YGTGWQRSFIADYGVPLMVVWTALSYSLPSKIPSGVPRRLFTPLPWEPK
    At2g47160.1 (226)   YGIGWLRSLIADYGVPLMVLVWTGVSYIPAGDVPKGIPRRLFSPNPWSPG
    At3g62270.1 (226)   YGIGWLRSLVADYGVPLMVLVWTGVSYIPTGDVPKGIPRRLFSPNPWSPG
    At3g06450.1 (228)   FGAEWLRGFIADYGVPVMVVWTCISYIPWKSVPQGIPRRLVSPNPWSPG
    At1g15460.1 (231)   YGTGWYRSFIADYGVPLMVVWTALSFSTPSKLPSGVPRRLFSPLPWDSP
    At1g74810.1 (231)   YGTGCCRSFVADYGVPLMVVWTALSFSTPSKLPSGVPRRLVSPLPWDSV
    At5g25430.1 (198)   YGFGWLRSFIGDYGVPLMVLLWTALSYTVPSEVLPSVPRRLECPLPWEPA
    At4g32510.1 (243)   YGFRWMRGFIGDYGTLLMLVLWSAFSYTVPRNLEEGVPRRLELPLPWASE
                        301                                                350
          Bot1   (279)  SLGHWTVAKDLFSVPPAYIFAAIVPALMVAGLYFFDHSVASQIAQQQEFN
   Os12g37840.1  (276)  AYDNWTVIRDMPNVPLLYIIGAFIPATMIAVLYYFDHSVASQIAQQKEFN
      Os01g08040 (276)  SLQHWTVAKDLFSVPPAYIFAAILPALMVAGLYFFDHSVASQIAQQKEFN
      Os01g08020 (276)  SLHHWTIAKDLFSVPPAYIFAAILPALMIAGLYFFDHSVASQIAQQKEFN
      Os05g08430 (277)  SLQHWTVAKDLFSVPPPYIFLAIVPAVMVAGLYFFDHSVASQIAQQKEFN
    At2g47160.1 (276)   AYGNWTVVKEMLDVPIVYIIGAFIPASMIAVLYYFDHSVASQIAQQKEFN
    At3g62270.1 (276)   AYENWTVVKEMLQVPIVYIIGAFIPATMIAVLYYFDHSVASQIAQQKEFN
    At3g06450.1 (278)   AYQNWTVIKEMVDVPVLYILLAVVPASMIAVLYYFDHSVASQIAQQEDFN
    At1g15460.1 (281)   SLSHWTVIKDMGKVSPGYIFAAIPALMIAGLYFFDHSVASQIAQQKEFN
    At1g74810.1 (281)   SLTHWTVIKDMGKVSPGYIFAAIPALMIAGLYFFDHVVSQIAQQKEFN
    At5g25430.1 (248)   SLYHWTVVKDMGKVPIMYILAAFIPGVMIAGLYFFDHSVASQMAQQKEFN
    At4g32510.1 (293)   SLYHWTVVKDMAKVPPLYILAAFIPAIMIAGLYFFDHCVSAQMAQQKEFN
                        351                                                400
          Bot1   (329)  LKKPSAYHYDILVLGFMVLLCGLIGIPPANGVIPQSPMHTRSLAVLKGQL
   Os12g37840.1  (326)  LRKPPSFHYDLLLLGFLTLLCGLIGIPPANGVIPQSPMHTKSLATLKHQL
      Os01g08040 (326)  LKKPSAYHYDILVLGFMVLLCGLIGIPPNGVIPQSPMHTRSLAVLKGQL
      Os01g08020 (326)  LKKPSAYHYDILVLGFMVLLCGLIGIPPNGVIPQSPMHTRSLAVLKGQL
      Os05g08430 (327)  LKNPSAYHYDILVLSFMVLICGLIGIPPNGVIPQSPMHTRSLAVLKGQL
    At2g47160.1 (326)   LRKPSSYHYDLLLLGFLTLMCGLLGVPPSNGVIPQSPMHTRSLATLKYQL
    At3g62270.1 (326)   LRKPSSYHYDLLLLGFLTLMCGLLGVPPSNGVIPQSPMHTKSLATLKYQL
    At3g06450.1 (328)   LRKPPAYHYDLFLLGFLTILCGLIGIPPSNGVIPQSPMHTKSLATLNHQL
    At1g15460.1 (331)   LKKPSAYHYDILILLGFMTLLCGLLGLPPSNGVLPQSPMHTKSLAVLKRQL
    At1g74810.1 (331)   LKNPSAYHYDILLLGFMVLICGMLGLPPSNGVLPQSPMHTKSLAVFKRQL
    At5g25430.1 (298)   LKNPSAYHYDIFLLGIITLICGLLGLPPSNGVLPQAPMHTKSLAVLNRQL
    At4g32510.1 (343)   LKNPTAYHYDIFILGIMTLICGLLGLPPSNGVIPQSPMHTKSLAVLKKQQ
```

FIG. 11C

```
                        401                                               450
        Bot1    (379)  MRKRMLRTAKEGMSNRASSLEIYGKMHEVFIEMDNKQDADS---------
  Os12g37840.1  (376)  LRNRLVATARQSMSQNASLSQLYGSMQEAYQQMQTPLIYQQPS-------
    Os01g08040  (376)  LRKKMVQTANEGLMNRASSLEIYGKIQGVFIEMDCEKNTDS---------
    Os01g08020  (376)  LRKKMVQTANEGLMNRASSLEIYGKMQGVFIEMDCEKNTDS---------
    Os05g08430  (377)  LRKKMVQTAKEGMMNNASSSEVYGKMQEVFIKMDDKSNAKS---------
   At2g47160.1  (376)  LRNRLVATARRSIKTNASLGQLYDNMQEAYHHMQTPLVYQQP--------
   At3g62270.1  (376)  LRNRLVATARKSIKQNASLGQLYGNMQDVYNQMQTPLVYQQP--------
   At3g06450.1  (378)  LRNKLVAAARKCIRNNATIGEVYGSMEEAYQQMQSPLIHQEP--------
   At1g15460.1  (381)  IRRKMVKTAKESIRKRETSSQVYENMQEVFIEMDKSPLAQTDP-------
   At1g74810.1  (381)  MRRKMVMTAKESIRQKATSSQVYEDMEQVFIEMDKSPLAETHT-------
   At5g25430.1  (348)  IRKKMVKKAKECMKMKASKSEIYGRMQSVFIEMETSPPQDN---------
   At4g32510.1  (393)  MRKKMVQKAKECMREKASNSEIYGRMQDVFIEMETSPKASNHICLINSLP
                        451                                               500
        Bot1    (420)  -----------VDKDLKSLKDAVLREGDE-----DGKLAGEFDPRKHIEA
  Os12g37840.1  (419)  -----------VKGLNELKDSTVQMASSMGNIDAPVDETVFDIEKEIDD
    Os01g08040  (417)  -----------VDKELKSLKDAILQEVDK-----EGTLAEEFDPIKHIEA
    Os01g08020  (417)  -----------VDKELKSLKDAMLQEGDK-----EGTLAEEFDPIKHIEA
    Os05g08430  (418)  -----------VRKELKELKDAVIPEGNG-----AGRVSEVFDPEKHIEA
   At2g47160.1  (418)  -------------QGLKELKESTIQATTFTGNLNAPVDETLFDIEKEIDD
   At3g62270.1  (418)  -------------QGLKELRESTIQATTFTGNLDAPVDETLFDIEKEIDD
   At3g06450.1  (420)  -------------SRIQGLKQSHIQKAS---NADALVDETVFDIETEVEN
   At1g15460.1  (424)  ----------SVIIELQDLKEAVMKSNDEE---REGDEESGFDPEKHLDA
   At1g74810.1  (424)  ----------TLINELQDLKEAVMKKSDDD---GDTGEESGFDPEKHVDA
   At5g25430.1  (389)  ----------SVATDLKELKEVVMRPDEGG----DTKG--KFDPDVHIEA
   At4g32510.1  (443)  LFLFSYQEATSVVKELENLKEAVMKADDGG---GETKGK-KFDPEVHIED
                        501                                               550
        Bot1    (454)  HLPVRVNEQRLSNLQSLLVGGCVGAMPVIKMIPTSVLWGYFAYMAIDSL
  Os12g37840.1  (457)  LLPIEVKEQRLSNLQATMVGGCVAAMPLLKKIPTSVLWGYFAFMAIESL
    Os01g08040  (451)  HLPVRVEQRLSNLQSLLVGACVGAMPVIKMIPTSVLWGYFAYMAIDSL
    Os01g08020  (451)  HLPVRVEQRLSNLQSLLVGACVGAMPVIKMIPTSVLWGYFAYMAIDSL
    Os05g08430  (452)  YLPVRVNEQRVSNLQSLLIAGCVGVMPIIQKIPTSVLWGYFAYMSIDSV
   At2g47160.1  (455)  LLPVEVKEQRSNLQSTMVGGCVAAMPILKMIPTSVLWGYFAFMAIESL
   At3g62270.1  (455)  LLPIEVKEQRSNLQAVMGGCVAAMPLLKMIPTSVLWGYFAFMAIESL
   At3g06450.1  (454)  ILPVEVKEQRVSNFQAMMVAGCVAAMPLIKRIPSSVLWGYFAYMAIESL
   At1g15460.1  (461)  YLPVRVNEQRSNLQSLLVAGAVLAMPAIKLIPTSILWGYFAYMAIDSL
   At1g74810.1  (461)  YLPVRVNEQRSNLQSLLVIGAVFALPVIKLIPISLLWGYFAYMAIDSL
   At5g25430.1  (423)  NLPVRVNEQRSNLQSVLVGLTLLAVTVIKMIPSSVLWGYFAYMAIDSL
   At4g32510.1  (489)  HLPVRVNEQRSNLQSVLVGLLILAVPVLRMIPTSVLWGYFTXMAVESL
                        551                                               600
        Bot1    (504)  PGNQFWERIQLLFVGASRRYKVLEGPHASFVESVSSRTIYVFTIFQIVYF
  Os12g37840.1  (507)  PGNQFWERILLLFTAPSRRYKVLEEYHTTFVETVPFKTIAMFTLFQTMYL
    Os01g08040  (501)  PGNQFWERLRLIFIPSSRRYKVLEGPHASFMESVPSKTITVFTIFQLVYL
    Os01g08020  (501)  PGNQFWERIRLIFIPSSRRYKVLEGPHASFMESVPSKTITVFTIFQLVYL
    Os05g08430  (502)  PGNQFWERTQLLFISPQRRYKLLEGAHASFMESVPIKKISAFTIFQLVYL
   At2g47160.1  (505)  PGNQFWERILLLFTAPSRRFKVLEDYHATFVETVPFKTIAMFTIFQTTYL
   At3g62270.1  (505)  PGNQFWERILLLFTAPSRRFKVLEDNHATFVETVPFKTIAMFTIFQTTYL
   At3g06450.1  (504)  PGNQFWERVLLLFTAPSRRFKVLEDNHAVFIETVPFKTMAMFTLFQTAYL
   At1g15460.1  (511)  PGNQFFERLTLLFVPTSRRFKVLEGAHASFVEKVPYKSMAAFTLLQIFYF
   At1g74810.1  (511)  PDNQFFERTVLLFVPPTRRFKVLEGAHASFVEKVPHKSIAAFTLFCILYF
   At5g25430.1  (473)  PGNQFWERLLLLFIPPSRLFKVLEGVHASFVELVPYRVIVTFTLFQLVYF
   At4g32510.1  (539)  PGNQFWERLQLLFITPGRRFKVLEGLHASFVEIVPYKSIVMFTLFQLLYF
```

FIG. 11D

```
                    601                                              650
      Bot1    (554) LICEGTWIPIAGILPPLPFFLMILIRQYLLPKFFEPNDLRELDAAEYDE
Os12g37840.1  (557) LVCEGITWIPIAGVLPPLMIMLLVPVRQYILPKLFKGAHLTDLDAAEYEE
  Os01g08040  (551) LICEGITWIPIAGILPPLPFFLMILIRQHVLPKFFEPNDLRELDAAEYEE
  Os01g08020  (551) LICEGITWIPIAGILPPLPFFLMILIRQHVLPKFFEPNDLRELDAAEYEE
  Os05g08430  (552) LIVWGMTWIPVAGILPPLFFFLIVIRQYILPKFFDPRHLWELDAAEYEE
  At2g47160.1 (555) LICEGLTWIPIAGVMPPLMIMFLIPVRQYLLPRFEKGAHLQDLDAAEYEE
  At3g62270.1 (555) LTCEGLTWIPIAGVMPPLIMFLIPVRQYILPRFKSAHLQDLDAAEYEE
  At3g06450.1 (554) LVCEGITWVPVAGVLPPLMIMFLVPVRQYVLPNFKGAHLQDLDAAEYEE
  At1g15460.1 (561) GLCYGVTWIPVAGIMPPVPFFLLIAIRQYILPKLNPAHLRELDAAEYCE
  At1g74810.1 (561) GLCYGVTWIPVAGIMPPVLFFLLVAIRQYLLPKLFKPAYLRELDAAEYEE
  At5g25430.1 (523) LLCYGMTWIPMAGIFPPALFFLLISIREHLLPKLFDMQHLQVLDASDYEE
  At4g32510.1 (589) LICYGVTWIPVGGILPPLPFFILIALRQYILQRLFDPSHLQVLDSSEYEE
                    651                                              700
      Bot1    (604) LEGVQHEHTLEEDGS---ISGSCDG---------RIDAEILDELITH-RG
Os12g37840.1  (607) SPAIPFIAAQ---DIDVALARTQSA------------EILDDIVTRSRG
  Os01g08040  (601) LEGVHHDHTLEDGES---DSGSCGS---------RDDAEIFDELITN-RG
  Os01g08020  (601) LEGVHHDHTLEDGAS---DSESCGS---------RDDAEILDELITN-RG
  Os05g08430  (602) LEGVRRDPSTDEDAS---VSRCSDAS--------PEYASEILDEFITN-RG
  At2g47160.1 (605) APALPFNLAA-ETEIGSTTSYPGDL------------EILDEVMTRSRG
  At3g62270.1 (605) APALPFHLAVPEAEMGSTASYPCDS------------EILDEFITRSRG
  At3g06450.1 (604) APAILSFNLKPEGEVSRATSFADSG-----------EVMDGMFTRSRG
  At1g15460.1 (611) IPGTPRNPLELSFR-----SNDSKR------GVQEGDAEILDELITS-RG
  At1g74810.1 (611) IPGTPRNPLELSFR-----SNNSAR------GVQECDAEILDELITS-RG
  At5g25430.1 (573) IVAAPIQHSSFAYR-KLGSSHHLSE-----GEDEFYDAEILDEMITS-RG
  At4g32510.1 (639) MVGAPQRNSSFGFNGELREAHNIPLSVVENSEDEFYDAEILDEIITS-RG
                    701                                              750
      Bot1    (641) ELKHRVVSHREERHLQVHSNAVQPSV----------------------
Os12g37840.1  (641) EIKRLNSPKITS--SGGTPVAELKG-IRSPCISERAYSPCITELRHDRSP
  Os01g08040  (638) ELKHRTSSHREERHLQVHSNAIQPRCGDTENLSEC---------------
  Os01g08020  (638) ELKHRTFNHREERHPQAHTKAVQPRCGDTENWSEC---------------
  Os05g08430  (641) ELKHRTKSFRDERLIQLNSVKMTRELSRIPTFTPPRS-------------
  At2g47160.1 (641) EFRHTSSPKVTS--SSSTPVNNRS--------LSQVFSPRVSGIRLGQMS
  At3g62270.1 (642) EFRHTCSPKVTS--STSTPVYNRN--------LSQVFSPRVIDLR-GEMS
  At3g06450.1 (641) EIRKVSSLKLGGGGSGSTVGSPAGGGVELMRRVVSFQNPRVSEKVYIRSL
  At1g15460.1 (649) ELKVRTLNLNEDKGNQIYPKEKVKAGDGDMSTTRE---------------
  At1g74810.1 (649) ELKVRTLGHNEDKGHQIYPKEIVEVGDGDMSSSRE---------------
  At5g25430.1 (616) EIRIRTISFKEVHPE---PEEKHVTFEPH---------------------
  At4g32510.1 (688) ELKHRTLSVKEDRSQ---MVKIYNHS------------------------
                    751                                          793
      Bot1    (667) ------------------------------------------
Os12g37840.1  (688) LGGRG----SPRTGETRSSKLGEGSTPK---------------
  Os01g08040  (673) ------------------------------------------
  Os01g08020  (673) ------------------------------------------
  Os05g08430  (678) ------------------------------------------
  At2g47160.1 (681) PRVVG---NSPKPASCGRSPLNQSSSN---------------
  At3g62270.1 (681) PRLSGKGQNSPK-----PSPLNPSSSSK--------------
  At3g06450.1 (691) SDFRGGGEISPR-SSAGRAPFSPRSATGGGGGEQRLSNLGKSV
  At1g15460.1 (684) ------------------------------------------
  At1g74810.1 (684) ------------------------------------------
  At5g25430.1 (642) ------------------------------------------
  At4g32510.1 (711) ------------------------------------------
```

BORON TRANSPORTER

PRIORITY CLAIM

The present application is a U.S. National Stage Application of PCT/AU2008/000018, filed Jan. 11, 2008, which claims priority to Australian provisional patent application 2007900157, the contents of which are hereby incorporated by reference.

FIELD OF THE INVENTION

The present invention relates to boron transporters and, in particular, to boron transporters derived from plants. The present invention also relates to methods that utilise boron transporters, such as methods for modulating boron transport in cells and methods for determining the level or rate of boron transport in a cell or organism on the basis of the expression level of one or more boron transporters.

INCORPORATION-BY-REFERENCE OF MATERIAL SUBMITTED AS AN ASCII TEXT FILE

A replacement Sequence Listing is submitted herewith as an ASCII compliant text file named "Replacement_Sequence_Listing.txt", created on Feb. 19, 2013, and having a size of ~95.9 kilobytes, as permitted under 37 CFR 1.821(c). The material in the aforementioned file is hereby incorporated by reference in its entirety.

BACKGROUND OF THE INVENTION

Boron is an essential plant micronutrient that is toxic at high soil concentrations. The range between boron deficiency and toxicity is narrow for plants, and imbalances in boron nutrition are common in agriculture. Whilst deficiency may be addressed easily through the application of boron rich fertilisers, boron toxicity is more difficult to manage agronomically. Boron levels are generally higher in subsoils than the surface root zone, making amelioration through soil modification difficult and impractical.

Boron toxicity is a major limitation to cereal production in southern Australia, and is also a problem in arid and semi-arid parts of the world including Asia and Africa. Yield penalties of up to 17% between adjacent areas of barley have been attributed to differences in shoot boron concentration. Similar figures (11%) have been reported for wheat in southern Australia. Soils high in boron tend to be associated with low rainfall environments (250-450 mm per year) and primarily derived from clay rich sediments of marine origin. Increasingly, boron toxicity is becoming associated with irrigated environments, where groundwater application contributes to an excessive accumulation of boron. Frequently boron is found at high concentrations in saline soils.

The known function of boron in plants is as a structural and functional component of cells walls and the plasma membrane. In plants boron exists primarily as boric acid [$B(OH)_3$], and to a lesser extent at neutral and alkaline pH as the borate anion [$B(OH)_4^-$]. Under adequate boron supply, uptake from the soil into plant roots via the plasma membrane is a passive process, and one that occurs rapidly: The half-time of influx into barley roots is approximately six minutes. Inside the plant cell, the ability of boron to form stable complexes with hydroxy compounds has been studied extensively. Examples of molecules that form complexes with boric acid include ribose, apiose, sorbitol and other polyols, glycoproteins and glycolipids. The binding of boron to apiose, the central component of the rhamnogalacturonan-II complex in primary plant cell walls is needed to maintain the normal physical properties of cell walls.

In vascular plants, boron moves from the roots within the transpiration stream and accumulates at the tips of older leaves. A sharp concentration gradient is observed within the leaf, and toxicity symptoms are directly correlated with boron distribution. Symptoms appear first at the tips of older leaves, where a high boron concentration leads to chlorosis and necrosis, first extending down the leaf margins. In barley this generally occurs at cellular concentrations in excess of 23 mM.

Variation in tolerance to boron toxicity exists both between and within species. The primary mechanism of tolerance appears to be similar for all species studied: an ability to maintain low concentrations of boron in plant tissues. However, the molecular basis for this is currently unknown. Boron tolerant genotypes generally accumulate lower concentrations of boron than intolerant genotypes, suggesting that exclusion rather than internal tolerance mechanisms are operating. It is however likely that other mechanisms related to internal tissue tolerance to boron are present in plants and have a significant role.

Interval regression mapping in both wheat and barley has identified the chromosomal location of several QTL for various boron tolerance traits. In barley, four QTL (on 2HS, 3HS, 4HL, 6HL) have been identified that have detectable effects on boron tolerance in barley. These are: Leaf Symptom Expression (a measure of severity of symptoms on the basis of leaf damage), Relative Root Length (root length at boron 100 mg/L$^{-1}$ expressed as a percentage of the root length at boron 0 mg/L$^{-1}$), Whole-shoot boron Concentration (shoot boron concentration of 5 week old plants as measured by Inductively Coupled Plasma Spectrometry, ICP) and Dry Matter Production (dry weight).

TABLE 1

Percentage variation associated with boron tolerance QTL:

| Parameter | Loci | Percentage trait variation |
| --- | --- | --- |
| Leaf Symptom Expression | 2HS, 4HL | 38 |
| Relative Root Length | 3HS, 4HL | 39 |
| Whole-shoot Boron Concentration | 4HL, 6HL | 53 |
| Dry Matter Production | 4HL | 34 |

It would be desirable to identify the nucleotide and amino acid sequences which encode boron transporters, and a way in which these could be expressed in plant tissues to avoid boron toxicity. The identification of such sequences would allow, among other things, the introduction, removal or modulation of boron transport activity in a range of cells and/or organisms, including plant cells and plants.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification of polypeptides, and their corresponding nucleic acids, that encode boron transporter molecules.

Throughout the text, the word boron is used as shorthand to refer to boron-containing compounds such as boric acid ($H_3BO_3$), the borate anion ($H_4BO_4$) and various boron-containing organic compounds, as opposed to elemental B specifically.

In particular, the present invention is predicated in part on the isolation of a polypeptide sequence from barley (*Hordeum vulgare*) which encodes a boron transporter that is associated with increased boron tolerance in at least the barley cultivars Sahara 3771. This polypeptide has been designated HvBot1, and comprises the amino acid sequence set forth in SEQ ID NO: 2. The open reading frame nucleic acid sequence which encodes the HvBot1 polypeptide has also been determined. This nucleotide sequence is designated as HvBot1 and comprises the nucleotide sequence set forth in SEQ ID NO: 1.

Accordingly, in a first aspect, the present invention provides an isolated nucleic acid comprising a nucleotide sequence selected from the list consisting of:
 (i) a nucleotide sequence which encodes a polypeptide comprising the amino acid sequence set forth in SEQ ID NO: 2;
 (ii) a nucleotide sequence which encodes a functional homolog of the polypeptide comprising the amino acid sequence set forth in SEQ ID NO: 2;
 (iii) a nucleotide sequence which is the complement or reverse complement of the nucleotide sequence referred to at (i) or (ii); and
 (iv) a fragment of the nucleotide sequence referred to at any of (i), (ii) or (iii).

The nucleotide sequences of the first aspect of the invention are also referred to herein as "Bot1 nucleic acids" or "Bot1 nucleic acid sequences".

Generally, the Bot1 nucleic acids of the present invention encode boron-transporter polypeptides.

In specific embodiments, the isolated Bot1 nucleic acid comprises a nucleic acid selected from the list consisting of:

(i) a nucleic acid comprising the nucleotide sequence set forth in SEQ ID NO: 1;

(ii) a nucleic acid comprising a nucleotide sequence which is at least 81% identical to the nucleotide sequence set forth in SEQ ID NO: 1;

(iii) a nucleic acid which hybridizes to a nucleic acid comprising the nucleotide sequence set forth in SEQ ID NO: 1 under stringent conditions;

(iv) a nucleic acid comprising a nucleotide sequence which is the complement or reverse complement of any one of (i) to (iii); and (v) a fragment of any of (i), (ii), (iii) or (iv).

The Bot1 nucleic acids of the present invention may be derived from any source. For example, the Bot1 nucleic acids may be derived from an organism, such as a plant.

In a second aspect, the present invention provides a nucleic acid construct or vector comprising the nucleic acid of the first aspect of the invention.

In a third aspect, the present invention provides a genetically modified cell comprising an introduced nucleic acid selected from the list consisting of:

(i) an isolated Bot1 nucleic acid of the first aspect of the invention; and (ii) a nucleic acid construct or vector of the second aspect of the invention.

Furthermore, in a fourth aspect, the present invention provides a multicellular structure comprising one or more cells of the third aspect of the invention.

As referred to herein, a "multicellular structure" includes any aggregation of one or more cells. As such, a multicellular structure specifically encompasses tissues, organs, whole organisms and parts thereof. Furthermore, a multicellular structure should also be understood to encompass multicellular aggregations of cultured cells such as colonies, plant calli, suspension cultures and the like.

In a fifth aspect, the present invention provides an isolated polypeptide selected from the list consisting of:

(i) a polypeptide comprising the amino acid sequence set forth in SEQ ID NO: 2;

(ii) a polypeptide which is a functional homolog of (i); and (iii) a fragment of (i) or (ii).

The polypeptides of the invention are also referred to herein as Bot1 polypeptides. Generally, the Bot1 polypeptides of the present invention comprise boron transporter polypeptides.

The isolated polypeptides and fragments thereof of the present invention may also be useful, for example, in the generation of antibodies that bind to Bot1 polypeptides. Accordingly, in a sixth aspect, the present invention provides an antibody or an epitope binding fragment thereof, raised against either a Bot1 polypeptide or a polypeptide comprising a Bot1 epitope.

In a seventh aspect, the present invention provides a method for modulating the rate, level and/or pattern of boron efflux from a cell, the method comprising modulating the activity and/or expression of a Bot1 polypeptide in said cell.

In one embodiment, the level and/or activity of the Bot1 polypeptide is modulated by modulating the expression of a Bot1 nucleic acid in the cell.

In an eighth aspect, the present invention provides a cell with a modulated rate, level and/or pattern of boron efflux.

In one embodiment, the cell of the eighth aspect of the invention is produced according to the method of the seventh aspect of the invention.

In a ninth aspect, the present invention also provides a multicellular structure wherein the multicellular structure comprises one or more cells of the eighth aspect of the invention.

In a tenth aspect, the present invention provides a method for ascertaining the boron sensitivity or tolerance of an organism, the method comprising determining the expression level of a Bot1 nucleic acid sequence and/or a Bot1 polypeptide in one or more cells of the organism, wherein a relatively high level of Bot1 nucleic acid sequence and/or a Bot1 polypeptide expression is associated with boron tolerance in the organism and a relatively low level of Bot1 nucleic acid sequence and/or Bot1 polypeptide expression is associated with boron sensitivity in the organism.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers <400>1 (SEQ ID NO:1), <400>2 (SEQ ID NO: 2), etc. A summary of the sequence identifiers is provided in Table 2. A sequence listing is provided at the end of the specification.

TABLE 2

Summary of Sequence Identifiers

| Sequence Identifier | Sequence |
| --- | --- |
| SEQ ID NO: 1 | HvBot1 (Sahara) open reading frame nucleotide sequence |

TABLE 2-continued

Summary of Sequence Identifiers

| Sequence Identifier | Sequence |
|---|---|
| SEQ ID NO: 2 | HvBot1 (Sahara) amino acid sequence |
| SEQ ID NO: 3 | HvBot1 (Sahara) genomic nucleotide sequence |
| SEQ ID NO: 4 | HvBot1 (Sahara) mRNA nucleotide sequence |
| SEQ ID NO: 5 | cDNA QPCR forward primer |
| SEQ ID NO: 6 | cDNA QPCR forward primer |
| SEQ ID NO: 7 | Genomic QPCR forward primer |
| SEQ ID NO: 8 | Genomic QPCR forward primer |
| SEQ ID NO: 9 | In situ hybridization forward primer |
| SEQ ID NO: 10 | In situ hybridization reverse primer |
| SEQ ID NO: 11 | Genomic Southern hybridization forward primer |
| SEQ ID NO: 12 | Genomic Southern hybridization reverse primer |
| SEQ ID NO: 13 | xBM181 forward primer |
| SEQ ID NO: 14 | xBM181 reverse primer |
| SEQ ID NO: 15 | xBM178 forward primer |
| SEQ ID NO: 16 | xBM178 reverse primer |
| SEQ ID NO: 17 | xBM160 forward primer |
| SEQ ID NO: 18 | xBM160 reverse primer |
| SEQ ID NO: 19 | xBot1 forward primer |
| SEQ ID NO: 20 | xBot1 reverse primer |
| SEQ ID NO: 21 | xBM162 forward primer |
| SEQ ID NO: 22 | xBM162 reverse primer |
| SEQ ID NO: 23 | xBM165 forward primer |
| SEQ ID NO: 24 | xBM165 reverse primer |
| SEQ ID NO: 25 | HvBot1 (Clipper) open reading frame nucleotide sequence |
| SEQ ID NO: 26 | HvBot1 (Clipper) amino acid sequence |
| SEQ ID NO: 27 | UAS$_G$ sequence |
| SEQ ID NO: 28 | OsBOR1 (Os12g37840.1) amino acid sequence |
| SEQ ID NO: 29 | OsBOR2 (Os01g08040) amino acid sequence |
| SEQ ID NO: 30 | OsBOR3 (Os01g08020) amino acid sequence |
| SEQ ID NO: 31 | OsBOR4 (Os05g08430) amino acid sequence |
| SEQ ID NO: 32 | AtBOR1 (At2g47160.1) amino acid sequence |
| SEQ ID NO: 33 | AtBOR2 (At3g62270.1) amino acid sequence |
| SEQ ID NO: 34 | AtBOR3 (At3g06450.1) amino acid sequence |
| SEQ ID NO: 35 | AtB0R4 (At1g15460.l) amino acid sequence |
| SEQ ID NO: 36 | AtB0R5 (At1g74810.1) amino acid sequence |
| SEQ ID NO: 37 | AtB0R6 (At5g25430.1) amino acid sequence |
| SEQ ID NO: 38 | AtB0R7 (At4g32510.1) amino acid sequence |

DESCRIPTION OF EXEMPLARY EMBODIMENTS

It is to be understood that the following description is for the purpose of describing particular embodiments only and is not intended to be limiting with respect to the above description.

The present invention is predicated, in part, on the identification of polypeptides, and their corresponding nucleic acids, that encode boron transporter proteins.

In an exemplary embodiment of the invention, a polypeptide has been isolated from barley (*Hordeum vulgare*) which encodes a boron transporter and which is associated with increased boron tolerance in at least the barley cultivar Sahara 3771. This polypeptide has been designated HvBot1, and comprises the amino acid sequence set forth in SEQ ID NO: 2. The open reading frame nucleic acid sequence which encodes the HvBot1 polypeptide has also been determined. This nucleotide sequence is designated as HvBot1 and comprises the nucleotide sequence set forth in SEQ ID NO: 1.

The present invention is also predicated, in part, on the discovery that the boron tolerant barley cultivar, Sahara 3771, expresses HvBot1 at a higher level than boron sensitive barley cultivars. In addition, it has also been recognised that barley cv. Sahara 3771 has an increased copy number of HvBot1 nucleic acid sequences in its genome in comparison with the boron sensitive barley cultivars.

Accordingly, in a first aspect, the present invention provides an isolated nucleic acid comprising a nucleotide sequence selected from the list consisting of:
 (i) a nucleotide sequence which encodes a polypeptide comprising the amino acid sequence set forth in SEQ ID NO: 2;
 (ii) a nucleotide sequence which encodes a functional homolog of the polypeptide comprising the amino acid sequence set forth in SEQ ID NO: 2;
 (iii) a nucleotide sequence which is the complement or reverse complement of the nucleotide sequence referred to at (i) or (ii); and
 (iv) a fragment of the nucleotide sequence referred to at any of (i), (ii) or (iii).

The nucleotide sequences of the first aspect of the invention are also referred to herein as "Bot1 nucleic acids" or "Bot1 nucleic acid sequences".

Generally, the Bot1 nucleic acids of the present invention encode boron-transporter polypeptides. As referred to herein, a "boron transporter" refers to any polypeptide which, alone or in conjunction with another molecule, is involved in the efflux, translocation or uptake of boron in a cell, tissue, organ, whole organism or part thereof. In one embodiment, the term "boron-transporter" refers to a polypeptide which is involved in the efflux of boron from a cell and, in some embodiments, a plant cell.

In some embodiments, the boron transporter polypeptides contemplated by the present invention include one or more transmembrane helices. In further embodiments of the invention, the boron transporter polypeptides comprise at least 2, at least 3, at least 4, at least 5, at least 6, at least 7, at least 8, at least 9 or at least 10 transmembrane helices. In one specific embodiment, the boron transporter contemplated by the present invention comprises 10, 11 or 12 transmembrane helices.

In the present invention, "isolated" refers to material removed from its original environment (e.g., the natural environment if it is naturally occurring), and thus is altered "by the hand of man" from its natural state. For example, an isolated nucleic acid could be part of a vector or a composition of matter, or could be contained within a cell, and still be "isolated" because that vector, composition of matter, or particular cell is not the original environment of the nucleic acid. An "isolated" nucleic acid molecule should also be understood to include a synthetic nucleic acid molecule, including those produced by chemical synthesis using known methods in the art or by in-vitro amplification (eg. polymerase chain reaction and the like).

The isolated nucleic acid molecules of the present invention may be composed of any polyribonucleotide or polydeoxribonucleotide, which may be unmodified RNA or DNA or modified RNA or DNA. For example, the isolated nucleic acid molecules can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, the isolated nucleic acid molecules can be composed of triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus, "nucleic acid" embraces chemically, enzymatically, or metabolically modified forms.

As set out above, the present invention contemplates a nucleic acid that comprises a nucleotide sequence which encodes a polypeptide comprising the amino acid sequence set forth in SEQ ID NO: 2, or a nucleic acid that comprises a nucleotide sequence which encodes a functional homolog of a polypeptide comprising the amino acid sequence set forth in SEQ ID NO: 2.

In one embodiment a "functional homolog" of a polypeptide comprising the amino acid sequence set forth in SEQ ID NO: 2 includes any polypeptide, wherein the polypeptide is able to transport boron across a cell membrane. In another embodiment, the functional homolog is able to transport boron across a plant cell membrane. In a yet further embodiment, the functional homolog is able to effect boron efflux from a cell, including a plant cell.

Notwithstanding the above, the functional homolog may comprise, for example, a polypeptide which has one or more amino acid insertions, deletions or substitutions relative to the polypeptide comprising the amino acid sequence set forth in SEQ ID NO: 2; a mutant form or allelic variant of the polypeptide comprising the amino acid sequence set forth in SEQ ID NO: 2; an ortholog of the polypeptide comprising the amino acid sequence set forth in SEQ ID NO: 2; an analog of the polypeptide comprising the amino acid sequence set forth in SEQ ID NO: 2; and the like.

In one embodiment, a "functional homolog" of a polypeptide comprising the amino acid sequence set forth in SEQ ID NO: 2 also comprises at least 84% amino acid sequence identity, at least 88% amino acid sequence identity, at least 92% amino acid sequence identity or at least 95%, 96%, 97%, 98%, 99% or 100% amino add sequence identity to SEQ ID NO: 2.

When comparing amino acid sequences, the compared sequences should be compared over a comparison window of at least 50 amino acid residues, at least 100 amino acid residues, at least 200 amino acid residues, at least 300 amino acid residues or over the full length of SEQ ID NO: 2. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

In one specific embodiment, the functional homolog of SEQ ID NO: 2 may be the Bot1 polypeptide from *Hordeum vulgare* cv. Clipper, which comprises the amino acid sequence set forth in SEQ ID NO: 26.

In another specific embodiment, the functional homolog of SEQ ID NO: 2 comprises a Bot1 polypeptide comprising:
 (i) a hydrophobic amino acid at amino acid residue number 305 of the Bot1 polypeptide; and/or
 (ii) a polar amino add at amino acid residue number 592 of the Bot1 polypeptide.

In some embodiments, the hydrophobic amino acid is leucine and/or the polar amino acid is aspartic acid.

In specific embodiments, the isolated Bot1 nucleic acid comprises a nucleic acid selected from the list consisting of:
 (i) a nucleic acid comprising the nucleotide sequence set forth in SEQ ID NO: 1;
 (ii) a nucleic acid comprising a nucleotide sequence which is at least 81% identical to the nucleotide sequence set forth in SEQ ID NO: 1;
 (iii) a nucleic acid which hybridizes to a nucleic acid comprising the nucleotide sequence set forth in SEQ ID NO: 1 under stringent conditions;
 (iv) a nucleic acid comprising a nucleotide sequence which is the complement or reverse complement of any one of (i) to (iii); and
 (v) a fragment of any of (i), (ii), (iii) or (iv).

As set out above, the nucleic acid referred to at (ii) comprises a nucleotide sequence having at least 81% nucleotide sequence identity to SEQ ID NO: 1. In other embodiments, the nucleic acid referred to at (ii) comprises at least 85% nucleotide sequence identity, at least 89% nucleotide sequence identity, at least 92% nucleotide sequence identity or at least 95%, 96%, 97%, 98%, 99% or 100% nucleotide sequence identity to SEQ ID NO: 1.

When comparing nucleic acid sequences to SEQ ID NO: 1 to calculate a percentage identity, the compared nucleotide sequences should be compared over a comparison window of at least 100 nucleotide residues, at least 200 nucleotide residues, at least 500 nucleotide residues, at least 1000 nucleotide residues or the full length of SEQ ID NO: 1. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

As set out above, the invention also contemplates a nucleic acid which hybridises to a nucleic acid comprising the nucleotide sequence set forth in SEQ ID NO: 1 under stringent conditions. As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilizing agents such as formamide. Stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity of hybridisation is also affected by post-hybridization wash conditions, the critical factors being the ionic strength and temperature of the final wash solution. For DNA-DNA hybrids, the $T_m$ can be approximated from the equation of Meinkoth and Wahl (*Anal. Biochem.* 138: 267-284, 1984), ie. $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilize a hybridization and/or wash at, for example, 1, 2, 3, or 4° C. lower than the thermal melting point ($T_m$); medium stringency conditions can utilize a hybridization and/or wash at, for example, 6, 7, 8, 9, or 10° C. lower than the thermal melting point ($T_m$); low stringency conditions can utilize a hybridization and/or wash at, for example, 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (*Laboratory Techniques in Biochemistry and Molecular Biology-Hybridization with Nucleic Acid Probes*, Pt I, Chapter 2, Elsevier, New York, 1993), Ausubel et al., eds. (*Current Protocols in Molecular Biology*, Chapter 2, Greene Publishing and Wiley-Interscience, N.Y., 1995) and Sambrook et al. (*Molecular Cloning: A Laboratory Manual*, $2^{nd}$ ed., Cold Spring Harbor Laboratory Press, Plainview, N.Y., 1989).

The Bot1 nucleic acids of the present invention may be derived from any source. For example, the Bot1 nucleic acids may be derived from an organism, such as a plant. Suitable plants include, for example, monocotyledonous angiosperms (monocots), dicotyledonous angiosperms (dicots), gymnosperms and the like.

In one embodiment, the Bot1 nucleic acid is derived from a monocot. In another embodiment the Bot1 nucleic acid is derived from a cereal crop plant. As used herein, the term "cereal crop plant" includes members of the Poaceae (grass family) that produce edible grain for human or animal food. Examples of Poaceae cereal crop plants which in no way limit the present invention include barley, wheat, rice, maize, millets, sorghum, rye, triticale, oats, teff, wild rice, spelt and the like. However, the term cereal crop plant should also be understood to include a number of non-Poaceae species that also produce edible grain and are known as the pseudocereals, such as amaranth, buckwheat and quinoa.

In one specific embodiment, the Bot1 nucleic acid is derived from a barley plant. In another embodiment, the Bot1 nucleic acid includes an HvBot1 nucleic acid as described herein.

In further embodiments, Bot1 nucleic acids may also be derived from dicots. Exemplary dicots include, for example, *Arabidopsis* spp., *Nicotiana* spp., *Medicago* spp., soyabean, canola, oil seed rape, sugar beet, mustard, sunflower, potato, safflower, cassava, yams, sweet potato, other Brassicaceae such as *Thellungiella halophila*, among others.

In yet further embodiments, the Bot1 nucleic acids of the present invention may be derived from a boron tolerant plant species or cultivar.

Alternatively, the Bot1 nucleic acid may be a synthetic nucleic acid.

Specific examples of additional Bot1 nucleic acids contemplated by the present invention include Bot1 nucleic acid orthologs of SEQ ID NO: 1, such as nucleic acids comprising the nucleotide sequence set forth in SEQ ID NO: 25. SEQ ID NO: 25 is derived from *Hordeum vulgare* cultivar Clipper. However, as would be appreciated by those of skill in the art, further orthologs may be derived from other cultivars of *Hordeum vulgare*, other species within the genus *Hordeum*, other plants in the Poaceae family or Poales order, other monocot plants, other dicot plants, other members of the plant kingdom or other non-plant eukaryotic or prokaryotic organisms.

The Bot1 nucleic acids contemplated by the present invention may also comprise one or more non-translated regions such as 3' and 5' untranslated regions and/or introns. For example, the Bot1 nucleic acids contemplated by the present invention may comprise, for example, mRNA sequences, cDNA sequences or genomic nucleotide sequences. For example, exemplary nucleotide sequences which comprise a Bot1 nucleic acid include the genomic nucleotide sequence set forth in SEQ ID NO: 3 or the mRNA sequence set forth in SEQ ID NO: 4.

As set out above, the present invention also contemplates fragments of the isolated Bot1 nucleic acids of the first aspect of the invention.

"Fragments" of a nucleotide sequence may be at least 10 nucleotides (nt), at least 20 nt, at least 50 nt, or at least 100, 150, 200, 250, 300, 350, 400, 450, 500, 550, or 600 nt in length. These fragments have numerous uses that would be evident to one of skill in the art and include, but are not limited to, diagnostic probes and primers. Of course, larger fragments may also be useful, as are fragments corresponding to most, if not all, of the nucleotide sequences SEQ ID NO: 1. By a fragment at least 10 nt in length, for example, is intended fragments which include 10 or more contiguous bases from, for example, the nucleotide sequence of SEQ ID NO: 1.

The nucleic acid of the first aspect of the invention may also comprise a plurality of Bot1 nucleic acid sequences. For example, in some embodiments of the invention, the nucleic acid of the first aspect of the invention may include multiple copies of a boron-transporter encoding nucleic acid. Accordingly, in some embodiments, the nucleic acid of the first aspect of the invention may include at least 1, at least 2, at least 3, at least 4, at least 5, at least 6, at least 7, at least 8, at least 9, or at least 10 copies of a Bot1 nucleic acid sequence.

In further embodiments, a nucleic acid encoding multiple copies of a Bot1 nucleic acid sequence may include an isolated genomic nucleotide sequence defining a cluster of Bot1 nucleic acids. Such nucleic acids may be derived from, for example, alleles from boron tolerant plants that include multiple copies of a Bot1 nucleic acid. In one specific embodiment, the nucleic acid of the first aspect of the invention may include an isolated genomic nucleotide sequence defining a cluster of Bot1 nucleic acids from *Hordeum vulgare* cv. Sahara 3771.

In a second aspect, the present invention provides a nucleic acid construct or vector comprising the nucleic acid of the first aspect of the invention.

The vector or construct of the invention may further comprise one or more of: an origin of replication for one or more hosts; a selectable marker gene which is active in one or more hosts; and/or one or more transcriptional control sequences.

As used herein, the term "selectable marker gene" includes any gene that confers a phenotype on a cell in which it is expressed, to facilitate the identification and/or selection of cells which are transfected or transformed with a genetic construct of the invention.

"Selectable marker genes" include any nucleotide sequences which, when expressed by a cell, confer a phenotype on the cell that facilitates the identification and/or selection of these transformed cells. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (eg. nptI and nptII) and hygromycin phosphotransferase genes (eg. hpt); herbicide resistance genes including glufosinate, phosphinothricin or bialaphos resistance genes such as phosphinothricin acetyl transferase encoding genes (eg. bar), glyphosate resistance genes including 3-enoyl pyruvyl shikimate 5-phosphate synthase encoding genes (eg. aroA), bromyxnil resistance genes including bromyxnil nitrilase encoding genes, sulfonamide resistance genes including dihydropterate synthase encoding genes (eg. sul) and sulfonylurea resistance genes including acetolactate synthase encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

Furthermore, it should be noted that the selectable marker gene may be a distinct open reading frame in the construct or may be expressed as a fusion protein with another polypeptide (eg. a Bot1 polypeptide).

As set out above, the nucleic acid construct or vector may also comprise one or more transcriptional control sequences. The term "transcriptional control sequence" should be understood to include any nucleic acid sequence which effects the transcription of an operably connected nucleic acid. A transcriptional control sequence may include, for example, a leader, polyadenylation sequence, promoter, enhancer or upstream activating sequence, and transcription terminator. Typically, a transcriptional control sequence at least includes a promoter. The term "promoter" as used herein, describes any nucleic acid which confers, activates or enhances expression of a nucleic acid molecule in a cell.

In one embodiment, at least one transcriptional control sequence is operably connected to the nucleic acid sequence of the first aspect of the invention. For the purposes of the present specification, a transcriptional control sequence is regarded as "operably connected" to a given gene or other nucleotide sequence when the transcriptional control sequence is able to promote, inhibit or otherwise modulate the transcription of the gene or other nucleotide sequence.

A promoter may regulate the expression of an operably connected nucleotide sequence constitutively, or differentially, with respect to the cell, tissue, organ or developmental stage at which expression occurs, in response to external stimuli such as physiological stresses, pathogens, or metal ions, amongst others, or in response to one or more transcriptional activators. As such, the promoter used in accordance with the methods of the present invention may include, for example, a constitutive promoter, an inducible promoter, a tissue-specific promoter or an activatable promoter.

The present invention contemplates the use of any promoter which is active in a cell of interest. As such, a wide array of promoters which are active in any of bacteria, fungi, animal cells or plant cells would be readily ascertained by one of ordinary skill in the art. However, in some embodiments of the invention, plant cells are used. Therefore, in these embodiments, plant-active constitutive, inducible, tissue-specific or activatable promoters may be used.

In one specific embodiment, the present invention contemplates the use of a native Bot1 promoter to drive the expression of a Bot1 nucleic acid.

Plant constitutive promoters typically direct expression in nearly all tissues of a plant and are largely independent of environmental and developmental factors. Examples of constitutive promoters that may be used in accordance with the present invention include plant viral derived promoters such as the Cauliflower Mosaic Virus 35S and 19S (CaMV 35S and CaMV 19S) promoters; bacterial plant pathogen derived promoters such as opine promoters derived from Agrobacterium spp., eg. the Agrobacterium-derived nopaline synthase (nos) promoter; and plant-derived promoters such as the rubisco small subunit gene (rbcS) promoter, the plant ubiquitin promoter (Pubi) and the rice actin promoter (Pact).

"Inducible" promoters include, but are not limited to, chemically inducible promoters and physically inducible promoters. Chemically inducible promoters include promoters which have activity that is regulated by chemical compounds such as alcohols, antibiotics, steroids, metal ions or other compounds. Examples of chemically inducible promoters include: alcohol regulated promoters (eg. see European Patent 637 339); tetracycline regulated promoters (eg. see U.S. Pat. No. 5,851,796 and U.S. Pat. No. 5,464,758); steroid responsive promoters such as glucocorticoid receptor promoters (eg. see U.S. Pat. No. 5,512,483), estrogen receptor promoters (eg. see European Patent Application 1 232 273), ecdysone receptor promoters (eg. see U.S. Pat. No. 6,379,945) and the like; metal-responsive promoters such as metallothionein promoters (eg. see U.S. Pat. No. 4,940,661, U.S. Pat. No. 4,579,821 and U.S. Pat. No. 4,601,978); and pathogenesis related promoters such as chitinase or lysozyme promoters (eg. see U.S. Pat. No. 5,654,414) or PR protein promoters (eg. see U.S. Pat. No. 5,689,044, U.S. Pat. No. 5,789,214, Australian Patent 708850, U.S. Pat. No. 6,429,362).

In another embodiment, the inducible promoter may be a boron-responsive promoter. As referred to herein, the term "boron-responsive" should be understood to mean that the level and/or rate of transcription effected by the transcriptional control sequence is modulatable in response to boron concentration and/or the concentration of a boron-containing compound. In one embodiment, the boron responsive transcriptional control sequence is boron-inducible, that is the level and/or rate of transcription effected by the transcriptional control sequence increases in response to increasing boron concentration.

The inducible promoter may also be a physically regulated promoter which is regulated by non-chemical environmental factors such as temperature (both heat and cold), light and the like. Examples of physically regulated promoters include heat shock promoters (eg. see U.S. Pat. No. 5,447,858, Australian Patent 732872, Canadian Patent Application 1324097); cold inducible promoters (eg. see U.S. Pat. No. 6,479,260, U.S. Pat. No. 6,184,443 and U.S. Pat. No. 5,847,102); light inducible promoters (eg. see U.S. Pat. No. 5,750,385 and Canadian Patent 132 1563); light repressible promoters (eg. see New Zealand Patent 508103 and U.S. Pat. No. 5,639,952).

"Tissue specific promoters" include promoters which are preferentially or specifically expressed in one or more specific cells, tissues or organs in an organism and/or one or more developmental stages of the organism. It should be understood that a tissue specific promoter may be either constitutive or inducible.

Examples of plant tissue specific promoters include: root specific promoters such as those described in US Patent Application 2001047525; fruit specific promoters including ovary specific and receptacle tissue specific promoters such as those described in European Patent 316 441, U.S. Pat. No. 5,753,475 and European Patent Application 973 922; and seed specific promoters such as those described in Australian Patent 612326 and European Patent application 0 781 849 and Australian Patent 746032.

The promoter may also be a promoter that is activatable by one or more transcriptional activators, referred to herein as an "activatable promoter". For example, the activatable promoter may comprise a minimal promoter operably connected to an Upstream Activating Sequence (UAS), which comprises, inter alia, a DNA binding site for one or more transcriptional activators.

As referred to herein the term "minimal promoter" should be understood to include any promoter that incorporates at least an RNA polymerase binding site and, optionally a TATA box and transcription initiation site and/or one or more CAAT boxes. In one embodiment wherein the cell is a plant cell, the minimal promoter may be derived from the Cauliflower Mosaic Virus 35S (CaMV 35S) promoter. The CaMV 35S derived minimal promoter may comprise, for example, a sequence that substantially corresponds to positions −90 to +1 (the transcription initiation site) of the CaMV 35S promoter (also referred to as a −90 CaMV 35S minimal promoter), −60 to +1 of the CaMV 35S promoter (also referred to as a −60 CaMV 35S minimal promoter) or −45 to +1 of the CaMV 35S promoter (also referred to as a −45 CaMV 35S minimal promoter).

As set out above, the activatable promoter may comprise a minimal promoter fused to an Upstream Activating Sequence (UAS). The UAS may be any sequence that can bind a transcriptional activator to activate the minimal promoter. Exemplary transcriptional activators include, for example: yeast derived transcription activators such as Gal4, Pdr1, Gcn4 and Ace1; the viral derived transcription activator, VP16; Hap1 (Hach et al., *J Biol Chem* 278: 248-254, 2000); Gaf1 (Hoe et al., *Gene* 215(2): 319-328, 1998); E2F (Albani et al., *J Biol Chem* 275: 19258-19267, 2000); HAND2 (Dai and Cserjesi, *J Biol Chem* 277: 12604-12612, 2002); NRF-1 and EWG (Herzig et al., *J Cell Sci* 113: 4263-4273, 2000); P/CAF (Itoh et al., *Nucl Acids Res* 28: 4291-4298, 2000); MafA (Kataoka et al., *J Biol Chem* 277: 49903-49910, 2002); human activating transcription factor 4 Pang and Hai, *J Biol Chem* 272: 24088-24095, 1997); Bcl10 (Liu et al., *Biochem Biophys Res Comm* 320(1): 1-6, 2004); CREB-H (Omori et al., *Nucl Acids Res* 29: 2154-2162, 2001); ARR1 and ARR2 (Sakai et al., *Plant J* 24(6): 703-711, 2000); Fos (Szuts and Bienz, *Proc Natl Acad Sci USA* 97: 5351-5356, 2000); HSF4 (Tanabe et al., *J Biol Chem* 274: 27845-27856, 1999); MAML1 (Wu et al., *Nat Genet* 26: 484-489, 2000).

In one embodiment, the UAS comprises a nucleotide sequence that is able to bind to at least the DNA-binding domain of the GAL4 transcriptional activator. UAS sequences, which can bind transcriptional activators that comprise at least the GAL4 DNA binding domain, are referred to herein as $UAS_G$. In another embodiment, the $UAS_G$ comprises the sequence 5'-CGGAGTACTGTCCTCCGAG-3' (SEQ ID NO: 27) or a functional homolog thereof.

As referred to herein, a "functional homolog" of the $UAS_G$ sequence should be understood to refer to any nucleotide sequence which can bind at least the GAL4 DNA binding domain and which may comprise a nucleotide sequence having at least 50% identity, at least 65% identity, at least 80% identity or at least 90% identity with the $UAS_G$ nucleotide sequence.

The UAS sequence in the activatable promoter may comprise a plurality of tandem repeats of a DNA binding domain target sequence. For example, in its native state, $UAS_G$ comprises four tandem repeats of the DNA binding domain target sequence. As such, the term "plurality" as used herein with regard to the number of tandem repeats of a DNA binding domain target sequence should be understood to include, for example, at least 2 tandem repeats, at least 3 tandem repeats or at least 4 tandem repeats.

As mentioned above, the control sequences may also include a terminator. The term "terminator" refers to a DNA sequence at the end of a transcriptional unit which signals termination of transcription. Terminators are 3'-non-translated DNA sequences generally containing a polyadenylation signal, which facilitate the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

The present invention extends to all genetic constructs essentially as described herein. These constructs may further include nucleotide sequences intended for the maintenance and/or replication of the genetic construct in prokaryotes or eukaryotes and/or the integration of the genetic construct or a part thereof into the genome of a eukaryotic or prokaryotic cell.

In one embodiment, the vector or construct is adapted to be at least partially transferred into a plant cell via *Agrobacterium*-mediated transformation. Accordingly, in another embodiment, the construct may comprise left and/or right T-DNA border sequences.

Suitable T-DNA border sequences would be readily ascertained by one of skill in the art. However, the term "T-DNA border sequences" should be understood to include, for example, any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (*Microbiology and Molecular Biology Reviews*, 67(1): 16-37, 2003).

In one embodiment, the vector or construct is adapted to be transferred into a plant via *Agrobacterium*-mediated transformation, however, the present invention also contemplates any suitable modifications to the genetic construct that facilitate bacterial mediated insertion into a plant cell via bacteria other than *Agrobacterium* sp., for example as described in Broothaerts et al. (*Nature* 433: 629-633, 2005).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an E. coli cell or a plant cell or an animal cell. Exemplary methods for cloning nucleic acid molecules are described in Sambrook et al. (2000, supra)

In a third aspect, the present invention provides a genetically modified cell comprising an introduced nucleic acid selected from the list consisting of:
(i) an isolated nucleic acid of the first aspect of the invention; and
(ii) a nucleic acid construct or vector of the second aspect of the invention.

As referred to herein, a "genetically modified cell" comprises a cell that is genetically modified with respect to the wild type of the cell. As such, a genetically modified cell may be a cell which has itself been genetically modified and/or the progeny of such a cell.

The nucleic acid may be introduced using any method known in the art which is suitable for the cell type being used, for example, those described in Sambrook and Russell (*Molecular Cloning—A Laboratory Manual*, $3^{rd}$ Ed., Cold Spring Harbor Laboratory Press, 2000).

In embodiments of the invention where the cell is a plant cell, suitable methods for introduction of a nucleic acid molecule may include, for example: *Agrobacterium*-mediated transformation, other bacterially-mediated transformation (see Broothaerts et al., 2005, supra) microprojectile bombardment based transformation methods and direct DNA uptake based methods. Roa-Rodriguez et al. (*Agrobacterium-mediated transformation of plants*, $3^{rd}$ Ed. CAMBIA Intellectual Property Resource, Canberra, Australia, 2003) review a wide array of suitable *Agrobacterium*-mediated plant transformation methods for a wide range of plant species. Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art.

The introduced nucleic acid may be single stranded or double stranded. The nucleic acid may be transcribed into mRNA and translated into a protein; may encode a non-translated RNA such as an RNAi construct, a cosuppression construct, antisense RNA, tRNA, miRNA, siRNA, ntRNA and the like; or may act directly in the cell. The introduced nucleic acid may be an unmodified DNA or RNA or a modified DNA or RNA which may include modifications to the nucleotide bases, sugar or phosphate backbones but which retain functional equivalency to a nucleic acid. The introduced nucleic acid may optionally be replicated in the cell; integrated into a chromosome or any extrachromosomal elements of the cell; and/or transcribed by the cell. Also, the introduced nucleic acid may be either homologous or heterologous with respect to the host cell. That is, the introduced nucleic acid may be derived from a cell of the same species as the genetically modified cell (ie. homologous) or the introduced nucleic may be derived from a different species (ie. heterologous). The transgene may also be a synthetic transgene.

The introduced nucleic acid referred to above may be maintained in the cell as a DNA molecule, as part of an episome (eg. a plasmid, cosmid, artificial chromosome or the like) or it may be integrated into the genomic DNA of a cell.

As used herein, the term "genomic DNA" should be understood in its broadest context to include any and all DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

The isolated nucleic acid molecule may be operably connected to a promoter such that a cell may express a Bot1 nucleic acid sequence.

The term "cell", as used herein, should be understood to include any cell type, including bacteria, archaea and eukaryotic cells including, for example, animal, plant and fungal cells. The cell may include, for example, a plant cell, a monocot plant cell, a cereal crop plant cell or a barley cell.

Furthermore, in a fourth aspect, the present invention provides a multicellular structure comprising one or more cells of the third aspect of the invention.

As referred to herein, a "multicellular structure" includes any aggregation of one or more cells. As such, a multicellular structure specifically encompasses tissues, organs, whole organisms and parts thereof. Furthermore, a multicellular structure should also be understood to encompass multicellular aggregations of cultured cells such as colonies, plant calli, suspension cultures and the like.

As mentioned above, in one embodiment of the invention, the cell is a plant cell and as such, the present invention includes a whole plant, plant tissue, plant organ, plant part, plant reproductive material or cultured plant tissue (eg. callus or suspension culture), comprising one or more plant cells according to the third aspect of the invention. In further embodiments, the cell is a monocot cell, a cereal crop cell or a barley cell and, thus, the present invention also specifically includes a whole plant, plant tissue, plant organ, plant part, plant reproductive material or cultured plant tissue (eg. callus or suspension culture), comprising one or more monocot, cereal crop plant or barley cells.

In a fifth aspect, the present invention provides an isolated polypeptide selected from the list consisting of:

(i) a polypeptide comprising the amino acid sequence set forth in SEQ ID NO: 2;

(ii) a polypeptide which is a functional homolog of (i), as hereinbefore defined; and (iii) a fragment of (i) or (ii).

The polypeptides of the invention are also referred to herein as Bot1 polypeptides. Generally, the Bot1 polypeptides of the present invention comprise boron transporter polypeptides, as hereinbefore defined.

As used herein, the term "polypeptide" should be understood to include any length polymer of amino acids. As such the term "polypeptide" should be understood to encompass, for example, peptides, polypeptides and proteins.

The Bot1 polypeptides of the present invention may be derived from any source. For example, the Bot1 polypeptides may be derived from an organism, such as a plant. Suitable plants include, for example, monocotyledonous angiosperms (monocots), dicotyledonous angiosperms (dicots), gymnosperms and the like.

In one embodiment, the Bot1 polypeptide is derived from a monocot. In another embodiment the Bot1 polypeptide is derived from a cereal crop plant. In one specific embodiment, the Bot1 polypeptide is derived from a barley plant. In another embodiment, the Bot1 polypeptide includes an HvBot1 polypeptide as described herein.

In further embodiments, Bot1 polypeptide may also be derived from dicots. Exemplary dicots include, for example, *Arabidopsis* spp., *Nicotiana* spp., *Medicago* spp., soyabean, canola, oil seed rape, sugar beet, mustard, sunflower, potato, safflower, cassava, yams, sweet potato, other Brassicaceae such as *Thellungiella halophila*, among others.

In yet further embodiments, the Bot1 polypeptide of the present invention may be derived from a boron tolerant plant species or cultivar.

The Bot1 polypeptide may also be produced in a recombinant expression system. For example, a Bot1 polypeptide may be recombinantly produced by introducing a Bot1 nucleic acid under the control of a promoter, into a cell, wherein the cell subsequently expresses the Bot1 nucleic acid and produced a Bot1 polypeptide.

A vast array of recombinant expression systems that may be used to express a Bot1 nucleic acid are known in the art. Exemplary recombinant expression systems include: bacterial expression systems such as *E. coli* expression systems (reviewed in Baneyx, *Curr. Opin. Biotechnol.* 10: 411-421, 1999; eg. see also *Gene expression in recombinant microorganisms*, Smith (Ed.), Marcel Dekker, Inc. New York, 1994; and *Protein Expression Technologies: Current Status and Future Trends*, Baneyx (Ed.), Chapters 2 and 3, Horizon Bioscience, Norwich, UK, 2004), *Bacillus* spp. expression systems (eg. see *Protein Expression Technologies: Current Status and Future Trends*, supra, chapter 4) and *Streptomyces* spp. expression systems (eg. see *Practical Streptomyces Genetics*, Kieser et al., (Eds.), Chapter 17, John Innes Foundation, Norwich, UK, 2000); fungal expression systems including yeast expression systems such as *Saccharomyces* spp., *Schizosaccharomyces pombe, Hansenula polymorpha* and *Pichia* spp. expression systems and filamentous fungi expression systems (eg. see *Protein Expression Technologies: Current Status and Future Trends*, supra, chapters 5, 6 and 7; Buckholz and Gleeson, *Bio/Technology* 9(11): 1067-1072, 1991; Cregg et al., *Mol. Biotechnol.* 16(1): 23-52, 2000; Cereghino and Cregg, *FEMS Microbiology Reviews* 24: 45-66, 2000; Cregg et al., *Bio/Technology* 11: 905-910, 1993); mammalian cell expression systems including Chinese Hamster Ovary (CHO) cell based expression systems (eg. see *Protein Expression Technologies: Current Status and Future Trends*, supra, chapter 9); insect cell cultures including baculovirus expression systems (eg. see *Protein Expression Technologies: Current Status and Future Trends*, supra, chapter 8; Kost and Condreay, *Curr. Opin. Biotechnol.* 10: 428-433, 1999; *Baculovirus Expression Vectors: A Laboratory Manual* WH Freeman & Co., New York, 1992; and *The Baculovirus Expression System: A Laboratory Manual*, Chapman & Hall, London, 1992); Plant cell expression systems such as tobacco, soybean, rice and tomato cell expression systems (eg. see review of Hellwig et al., *Nat Biotechnol* 22: 1415-1422, 2004); and the like.

Alternatively, the Bot1 polypeptide may be a synthetic nucleic acid.

The Bot1 polypeptides of the present invention may be composed of amino acids joined to each other by peptide bonds or modified peptide bonds, ie., peptide isosteres, and may contain amino acids other than the 20 gene-encoded amino acids. The isolated polypeptides of the present invention may be modified by either natural processes, such as post-translational processing, or by chemical modification techniques which as are known in the art.

Modifications can occur anywhere in the polypeptide, including the peptide backbone, the amino acid side-chains and/or the termini. It will be appreciated that the same type of modification may be present in the same or varying degrees at several sites in a given isolated polypeptide. Also, an isolated polypeptide of the present invention may contain more than one type of modification.

The polypeptides of the invention may be branched, for example, as a result of ubiquitination, and/or they may be cyclic, with or without branching. Cyclic, branched, and branched cyclic polypeptides may result from post-translation natural processes or may be made by synthetic methods.

Exemplary polypeptide modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties* $2^{nd}$ Ed., Creighton (ed.), W. H. Freeman and Company, New York, 1993); *Posttranslational Covalent Modification Of Proteins*, Johnson (Ed.), Academic Press, New York, 1983; Seifter et al., *Meth Enzymol* 182: 626-646, 1990); Rattan et al., *Ann NY Acad Sci* 663: 48-62, 1992).

The "functional homologs" contemplated by the fifth aspect of the invention may comprise a functional homolog of SEQ ID NO: 2 as hereinbefore described.

As set out above, the present invention also provides polypeptide fragments. Polypeptide fragments may be "free-standing" or comprised within a larger polypeptide of which the fragment forms a part or region.

The polypeptide fragments may be at least 3, 4, 5, 6, 8, 9, 10, 11, 12, 13, 15, 20, 25, 30, 35, 40, 45, 50, 60, 70, 80, 90, 100, 110, 120, 130, 140, 150, 200, 250 or 300 amino acids in length. In one embodiment, the fragment comprises an amino acid sequence which is a fragment of the sequence set forth in SEQ ID NO: 2.

In another embodiment, the fragment comprises the functional activity of a boron transporter. However, even if the fragment does not retain one or more biological functions of a boron transporter polypeptide, other functional activities may still be retained. For example, fragments may retain the ability to induce the production of, and/or bind to, antibodies which recognize a complete or mature form of a Bot1 polypeptide. A peptide, polypeptide or protein fragment which has the ability to induce and/or bind to antibodies which recognize the complete or mature forms of an isolated Bot1 polypeptide is referred to herein as a "Bot1 epitope".

A Bot1 epitope may comprise as few as three or four amino acid residues, but may also include, for example, at least 5 amino acid residues, at least 10 amino acid residues, at least 20 amino acid residues, at least 50 amino acid residues or at least 100 amino acid residues. Whether a particular Bot1 polypeptide fragment retains such immunologic activities can readily be determined by methods known in the art. As such, in some embodiments, a Bot1 polypeptide fragment may be, for example, a polypeptide comprising one or more Bot1 epitopes.

A polypeptide comprising one or more Bot1 epitopes may be produced by any conventional means for making polypeptides including, for example, synthetic and recombinant methods known in the art. In one embodiment, Bot1 epitope containing polypeptide may be synthesized using known methods of chemical synthesis. For instance, Houghten has described a method for the synthesis of large numbers of peptides (Houghten, *Proc. Natl. Acad. Sci. USA* 82: 5131-5135, 1985).

The isolated polypeptides and fragments thereof of the present invention may also be useful, for example, in the generation of antibodies that bind to Bot1 polypeptides.

Such antibodies are useful, for example, in the detection and localization of Bot1 polypeptides and in affinity purification of Bot1 polypeptides. The antibodies may also routinely be used in a variety of qualitative or quantitative immunoassays using methods known in the art. For example see Harlow et al., *Antibodies: A Laboratory Manual*, (Cold Spring Harbor Laboratory Press $2^{nd}$ Ed., 1988).

Accordingly, in a sixth aspect, the present invention provides an antibody or an epitope binding fragment thereof, raised against either a Bot1 polypeptide or a polypeptide comprising a Bot1 epitope.

The antibodies of the present invention include, but are not limited to, polyclonal, monoclonal, multispecific, chimeric antibodies, single chain antibodies, Fab fragments, F(ab') fragments, fragments produced by a Fab expression library and epitope-binding fragments of any of the above.

The term "antibody", as used herein, refers to immunoglobulin molecules and immunologically active portions of immunoglobulin molecules, i.e., molecules that contain an antigen-binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be mono specific, bispecific, trispecific, or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. For example, see PCT publications WO 93/17715; WO 92/08802; WO 91/00360; WO 92/05793; Tutt et al., *J. Immunol.* 147: 60-69, 1991; U.S. Pat. Nos. 4,474,893; 4,714,681; 4,925,648; 5,573,920; 5,601,819; and Kostelny et al. *J. Immunol.* 148: 1547-1553, 1992).

In one embodiment, the antibodies of the present invention may act as agonists or antagonists of a Bot1 polypeptide. In further embodiments, the antibodies of the present invention may be used, for example, to purify, detect, and target the polypeptides of the present invention, including both in vitro and in vivo diagnostic and therapeutic methods. For example, the antibodies have use in immunoassays for qualitatively and quantitatively measuring levels of Bot1 polypeptide in biological samples. See, e.g., Harlow et al., *Antibodies: A Laboratory Manual* (Cold Spring Harbor Laboratory Press, 2nd ed. 1988).

The term "antibody", as used herein, should also be understood to encompass derivatives that are modified, eg. by the covalent attachment of any type of molecule to the antibody such that covalent attachment does not prevent the antibody from binding to a Bot1 polypeptide or an epitope thereof. For example, the antibody derivatives include antibodies that have been modified, eg., by glycosylation, acetylation, pegylation, phosphorylation, amidation, derivatization by known protecting/blocking groups, proteolytic cleavage, linkage to a cellular ligand or other protein, etc. Furthermore, any of numerous chemical modifications may also be made using known techniques. These include specific chemical cleavage, acetylation, formylation, etc. Additionally, the derivative may contain one or more non-classical amino acids.

Antibodies may be generated using methods known in the art, such as in vivo immunization, in vitro immunization, and phage display methods. For example, see Bittle et al. (*J. Gen. Virol.* 66: 2347-2354, 1985).

If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For example, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

For example, polyclonal antibodies to a Bot1 polypeptide or a polypeptide comprising one or more Bot1 epitopes can be produced using methods known in the art. For example, animals such as rabbits, rats or mice may be immunized with either free or carrier-coupled peptides. For instance, intraperitoneal and/or intradermal injection of emulsions containing about 100 micrograms of peptide or carrier protein may be used to induce the production of sera containing polyclonal antibodies specific for the antigen. Various adjuvants may also be used to increase the immunological response, depending on the host species, for example, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Several booster injections may be needed, for example, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods known in the art.

As another example, monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed., 1988) and Hammerling et al., in: *Monoclonal Antibodies and T-Cell Hybridomas* (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are known in the art. For example, mice can be immunized with a polypeptide of the invention or a cell expressing such peptide. Once an immune response is detected, eg., antibodies specific for the antigen are detected in the mouse serum, the mouse spleen is harvested and splenocytes isolated. The splenocytes are then fused to any suitable myeloma cells, for example cells from cell line SP20, which is available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Antibody fragments which recognize one or more Bot1 epitopes may also be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized, for example, to display antigen-binding domains expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phages used in these methods are typically filamentous phage including fd and M13 binding domains expressed from phage with Fab, Fv or disulfide stabilized Fv antibody domains recombinantly fused to either the phage gene III or gene VIII protein.

Examples of phage display methods that can be used to make the antibodies of the present invention include those disclosed by Brinkman et al. (*J. Immunol. Methods* 182: 41-50, 1995), Ames et al. (*J. Immunol. Methods* 184: 177-186, 1995), Kettleborough et al. (*Eur. J. Immunol.* 24: 952-958, 1994), Persic et al. (*Gene* 187: 9-18, 1997), Burton et al. (*Advances in Immunology* 57: 191-280, 1994); PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the antibody coding regions from the phage can be isolated and used to generate whole antibodies or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al. (*BioTechniques* 12(6): 864-869, 1992); and Sawai et al. (*AJRI* 34:26-34, 1995); and Better et al. (*Science* 240: 1041-1043, 1988).

Examples of techniques which can be used to produce single-chain Fvs and antibodies include those described in U.S. Pat. Nos. 4,946,778 and 5,258,498; Huston et al. (*Methods in Enzymology* 203: 46-88, 1991); Shu et al. (*Proc. Natl. Acad. Sci. USA* 90: 7995-7999, 1993); and Skerra et al. (*Science* 240: 1038-1040, 1988).

In a seventh aspect, the present invention provides a method for modulating the rate, level and/or pattern of boron efflux from a cell, the method comprising modulating the activity and/or expression of a Bot1 polypeptide in said cell.

As set out above, the "cell" may be any suitable eukaryotic or prokaryotic cell. As such, a "cell" as referred to herein may be a eukaryotic cell including a fungal cell such as a yeast cell or mycelial fungus cell; an animal cell such as a mammalian cell or an insect cell; or a plant cell. Alternatively, the cell may also be a prokaryotic cell such as a bacterial cell (eg. an *E. coli* cell), or an archaea cell.

In some embodiments, the cell may be, for example, a plant cell, a vascular plant cell, including a monocotyledonous or dicotyledonous angiosperm plant cell or a gymnosperm plant cell. In a further embodiment, the plant cell is a monocotyledonous plant cell. In specific embodiments, the monocotyledonous plant cell may be a cereal crop plant cell or a barley cell.

As set out above, the present invention is predicated, in part, on modulating the level and/or activity of a Bot1 polypeptide in a cell.

As referred to herein, modulation of the "level" of a Bot1 polypeptide should be understood to include an increase or decrease in the level or amount of a Bot1 polypeptide in the cell. Similarly, modulation of the "activity" of a Bot1 polypeptide should be understood to include an increase or decrease in, for example, the total activity, specific activity, half-life and/or stability of a Bot1 polypeptide in the cell.

By "increasing" is intended, for example, a 1%, 5%, 10%, 20%, 30%, 40%, 50%, 60%, 70%, 80%, 90%, 100%, 2-fold, 5-fold, 10-fold, 20 fold, 50-fold, 100-fold increase in the level of activity of a Bot1 polypeptide in the cell. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the level or activity of a Bot1 polypeptide in the cell.

"Modulating" should also be understood to include introducing a Bot1 polypeptide into a cell which does not normally express the introduced enzyme, or the substantially complete inhibition of Bot1 polypeptide activity in a cell that normally has such activity.

The present invention contemplates any means by which the level and/or activity of a Bot1 polypeptide in a cell may be modulated. This includes, for example, methods such as the application of agents which modulate Bot1 polypeptide activity in a cell, including the application of a Bot1 polypeptide agonist or antagonist; the application of agents which mimic Bot1 polypeptide activity in a cell; modulating the expression of a Bot1 nucleic acid which encodes a Bot1 polypeptide in the cell; or effecting the expression of an altered or mutated Bot1 nucleic acid in a cell such that a Bot1 polypeptide with increased or decreased specific activity, half-life and/or stability is expressed by the cell.

In one embodiment, the level and/or activity of the Bot1 polypeptide is modulated by modulating the expression of a Bot1 nucleic acid in the cell.

The term "modulating" with regard to the expression of a Bot1 nucleic acid may include increasing or decreasing the transcription and/or translation of a Bot1 nucleic acid. By "increasing" is intended, for example a 1%, 5%, 10%, 20%, 30%, 40%, 50%, 60%, 70%, 80%, 90%, 100%, 2-fold, 5-fold, 10-fold, 20-fold, 50-fold, 100-fold or greater increase in the transcription and/or translation of a Bot1 nucleic acid. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the transcription and/or translation of a Bot1 nucleic acid. Modulating also comprises introducing expression of a Bot1 nucleic acid not normally found in a particular cell; or the substantially complete inhibition (eg. knockout) of expression of a Bot1 nucleic acid in a cell that normally has such activity.

The present invention contemplates any means by which the expression of a Bot1 nucleic acid may be modulated. For example, exemplary methods for modulating the expression of a Bot1 nucleic acid include, for example: genetic modification of the cell to upregulate or downregulate endogenous Bot1 nucleic acid expression; genetic modification by transformation with a Bot1 nucleic acid; genetic modification to increase the copy number of a Bot1 nucleic acid sequence in the cell; administration of a nucleic acid molecule to the cell which modulates expression of an endogenous Bot1 nucleic acid in the cell; and the like.

In one embodiment, the expression of a Bot1 nucleic acid is modulated by genetic modification of the cell. The term "genetically modified", as used herein, should be understood to include any genetic modification that effects an alteration in the expression of a Bot1 nucleic acid in the genetically modified cell relative to a non-genetically modified form of the cell. Exemplary types of genetic modification include: random mutagenesis such as transposon, chemical, UV and phage mutagenesis together with selection of mutants which overexpress or underexpress an endogenous Bot1 nucleic acid; transient or stable introduction of one or more nucleic acid molecules into a cell which direct the expression and/or overexpression of Bot1 nucleic acid in the cell; inhibition of an endogenous Bot1 polypeptide by site-directed mutagenesis of an endogenous Bot1 nucleic acid; introduction of one or more nucleic acid molecules which inhibit the expression of an endogenous Bot1 nucleic acid in the cell, eg. a cosuppression construct or an RNAi construct; and the like.

In one specific embodiment, the present invention contemplates increasing the level of Bot1 polypeptide in a cell, by introducing the expression of a Bot1 nucleic acid into the cell, upregulating the expression of a Bot1 nucleic acid in the cell and/or increasing the copy number of a Bot1 nucleic acid in the cell. In one embodiment, the introduced Bot1 nucleic acid may be placed under the control of a transcriptional control sequence such as a native Bot1 promoter or a heterologous promoter.

In a further specific embodiment, the method of the seventh aspect of the invention contemplates increasing the expression of a Bot1 nucleic acid in a cell by introducing an isolated genomic nucleotide sequence defining a cluster of Bot1 nucleic acids from a boron tolerant organism (eg. barley cv. Sahara 3771) into the subject cell.

Methods for plant transformation and expression of an introduced nucleotide sequence are well known in the art, and the present invention contemplates the use of any suitable method. However, by way of example, reference is made to Zhao et al. (*Mol Breeding* DOI 10.1007/s11032-006-9005-6, 2006), Katsuhara et al. (*Plant Cell Physiol* 44(12): 1378-1383, 2003), Ohta et al. (*FEBS Letters* 532: 279-282, 2002) and Wu et al. (*Plant Science* 169: 65-73, 2005).

In further embodiments the present invention also provides methods for down-regulating expression of a Bot1 nucleic acid in a cell. For example, with the identification of Bot1 nucleic acid sequences, the present invention also facilitates methods such as knockout or knockdown of a Bot1 nucleic acid in a cell using methods including, for example:

(i) insertional mutagenesis of a Bot1 nucleic acid in a cell including knockout or knockdown of a Bot1 nucleic acid in a cell by homologous recombination with a knockout construct (for an example of targeted gene disruption in plants see Terada et al., *Nat. Biotechnol.* 20: 1030-1034, 2002);

(ii) post-transcriptional gene silencing (PTGS) or RNAi of a Bot1 nucleic acid in a cell (for review of PTGS and RNAi see Sharp, *Genes Dev.* 15(5): 485-490, 2001; and Hannon, *Nature* 418: 244-51, 2002);

(iii) transformation of a cell with an antisense construct directed against a Bot1 nucleic acid (for examples of antisense suppression in plants see van der Krol et al., *Nature* 333: 866-869; van der Krol et al., *BioTechniques* 6: 958-967; and van der Krol et al., *Gen. Genet.* 220: 204-212);

(iv) transformation of a cell with a co-suppression construct directed against a Bot1 nucleic acid (for an example of co-suppression in plants see van der Krol et al., *Plant Cell* 2(4): 291-299);

(v) transformation of a cell with a construct encoding a double stranded RNA directed against a Bot1 nucleic acid (for an example of dsRNA mediated gene silencing see Waterhouse et al., *Proc. Natl. Acad. Sci. USA* 95: 13959-13964, 1998); and (vi) transformation of a cell with a construct encoding an siRNA or hairpin RNA directed against a Bot1 nucleic acid (for an example of siRNA or hairpin RNA mediated gene silencing in plants see Lu et al., *Nucl. Acids Res.* 32(21): e171; doi:10.1093/nar/gnh170, 2004).

The present invention also facilitates the downregulation of a Bot1 nucleic acid in a cell via the use of synthetic oligonucleotides, for example, siRNAs or microRNAs directed against a Bot1 nucleic acid (for examples of synthetic siRNA mediated silencing see Caplen et al., *Proc. Natl. Acad. Sci. USA* 98: 9742-9747, 2001; Elbashir et al., *Genes Dev.* 15: 188-200, 2001; Elbashir et al., *Nature* 411: 494-498, 2001; Elbashir et al., *EMBO J.* 20: 6877-6888, 2001; and Elbashir et al., *Methods* 26: 199-213, 2002).

In one embodiment, downregulation, knock-out or knock-down of a Bot1 nucleic acid in a cell or organism may effect a reduction in the Boron tolerance of the cell or organism. In a further embodiment, downregulation, knock-out or knock-down of a Bot1 nucleic acid in a cell or organism may effect a an increase in the Boron sensitivity or Boron use efficiency of a cell or organism. For example, downregulation, knock-out or knock-down of a Bot1 nucleic acid in a plant or one or more cells thereof may increase the boron use efficiency of the plant for growth in a boron deficient environment.

In addition to the examples above, the introduced nucleic acid may also comprise a nucleotide sequence which is not directly related to a Bot1 nucleic acid but, nonetheless, may directly or indirectly modulate the expression of a Bot1 nucleic acid in a cell. Examples include nucleic acid molecules that encode transcription factors or other proteins which promote or suppress the expression of an endogenous Bot1 nucleic acid molecule in a cell; and other non-translated RNAs which directly or indirectly promote or suppress endogenous Bot1 polypeptide expression and the like.

In order to effect expression of an introduced nucleic acid in a genetically modified cell, where appropriate, the introduced nucleic add may be operably connected to one or more transcriptional control sequences and/or promoters, as previously described.

In an eighth aspect, the present invention provides a cell with a modulated rate, level and/or pattern of boron efflux.

As referred to herein, a cell having a "modulated" rate, level and/or pattern of boron efflux should be understood to include any cell in which the rate, level and/or pattern of boron efflux is different to that of the wild type (or unmodulated) form of the cell. In one embodiment, the cell has an increased rate and/or level of boron efflux relative to a wild type form of the cell.

In one embodiment, the cell of the eighth aspect of the invention is produced according to the method of the seventh aspect of the invention.

In a ninth aspect, the present invention also provides a multicellular structure, wherein the multicellular structure comprises one or more cells of the eighth aspect of the invention.

In a tenth aspect, the present invention provides a method for ascertaining the boron sensitivity or tolerance of an organism, the method comprising determining the expression level of a Bot1 nucleic acid sequence and/or a Bot1 polypeptide in one or more cells of the organism, wherein a relatively high level of Bot1 nucleic acid sequence and/or a Bot1 polypeptide expression is associated with boron tolerance in the organism and a relatively low level of Bot1 nucleic acid sequence and/or Bot1 polypeptide expression is associated with boron sensitivity in the organism.

Methods for determining the level and/or pattern of expression of a nucleic acid or polypeptide are known in the art. Exemplary methods of the detection of RNA expression include methods such as quantitative or semi-quantitative reverse-transcriptase PCR (eg. see Burton et al., *Plant Physiology* 134: 224-236, 2004), in-situ hybridization (eg. see Linnestad et al., *Plant Physiology* 118: 1169-1180, 1998); northern blotting (eg. see Mizuno et al., Plant Physiology 132: 1989-1997, 2003); and the like. Exemplary methods for the expression of a polypeptide include Western blotting (eg. see Fido et al., *Methods Mol Biol.* 49: 423-37, 1995); ELISA (eg. see Gendloff et al., *Plant Molecular Biology* 14: 575-583); immunomicroscopy (eg. see Asghar et al., *Protoplasma* 177: 87-94, 1994) and the like.

In another embodiment, the expression level of a Bot1 nucleic acid sequence and/or a Bot1 polypeptide may be determined by determining the number of Bot1 nucleic acids present in the genomic DNA of one or more cells of the organism. In this embodiment, multiple copies of a Bot1 nucleic acid in the genome are predictive of a relatively high expression level of a Bot1 nucleic acid sequence and/or a Bot1 polypeptide in the cell. In further specific embodiments, a relatively high level of Bot1 nucleic acid sequence and/or a Bot1 polypeptide expression is indicated by the presence of at least 2, at least 3, at least 4, at least 5, at least 6, at least 7, at least 8, at least 9, or at least 10 copies of a Bot1 nucleic acid in the genome of one or more cells of the organism.

In one embodiment, the method of the tenth aspect of the invention is adapted to ascertaining the boron sensitivity or tolerance of a plant. In further embodiments, the method of the tenth aspect of the invention is adapted to ascertaining the boron sensitivity or tolerance of, for example, a monocot plant, a cereal crop plant or a barley plant.

In further embodiments, the method of the tenth aspect of the invention may be used to ascertain the boron sensitivity or tolerance of an organism and then select individual organisms on the basis of the ascertained level of boron sensitivity or tolerance. For example, in the case of plants, plants having increased boron tolerance may be selected for planting in high boron soils or may be selected for breeding programs to produce boron tolerant cultivars of the plant.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

BRIEF DESCRIPTION OF THE FIGURES

FIG. 1. Genetic variation for boron tolerance in barley. (A) Boron toxicity symptoms in leaf blades of boron intolerant (Clipper) and boron tolerant (Sahara) barley plants. Approximately eight of the oldest leaf blades from single plants are shown 14 days after boron treatment. (B) Sahara accumulates less boron in leaf blades after growing for 14 days in a range of solution concentrations. Data are means±s.e.m. (n=3).

FIG. 2. Bot1 mapping and phylogenetic analysis. (A) Barley-rice comparative mapping of the boron toxicity tolerance locus on chromosome 4H. Numbers indicate recombinants identified for each marker interval. The related rice chromosome three (AP008209) interval spans the position 1,861,805-1,873,065 bp. Arrows I-VIII denote position and orientation of predicted rice genes Os03g0133300 (hypothetical protein), Os03g0133400 (Peptidoglycan-binding LysM domain containing protein), Os03g0133500 (AMP binding protein 1 AMPBP1), Os03g0133600 (AMP-dependent synthetase and ligase domain containing protein), Os03g0133800 (AMP binding protein 1 AMPBP1), Os03g0133900 (Serine acetyltransferase), Os03g0134000 (MuDR transposase domain containing protein) and Os03g0134300 (ATP phosphoribosyl transferase), respectively. Accession numbers are: xBot1, BV723959; xBM160, BV723960; xBM165, BV723961; xBM178, BV723962; xBM181, BV723963; xBM162, BV723964. (B) Phylogenetic tree including Bot1 and BOR1-like proteins from rice (Os05g08430, Os01g08040, Os01g08020, and Os12g37840.1) and *Arabidopsis* (At1g15460.1, At1g74810.1, At4g32510.1, At5g25430.1, At3g62270.1, At2g47160.1, and At3g06450.1), constructed using PHYLIP. Numbers separating junctions are bootstrap values. The closest rice orthologue of Bot1 is Os01g08020. Locus accessions are according to Gramene.

FIG. 3. Bot1 provides boron tolerance in yeast. Growth of *Saccharomyces cerevisiae* on solid medium containing 0 or 20 mM supplemental $H_3BO_3$. Each plate shows two independent yeast clones containing either empty vector, Sahara Bot1 or Clipper Bot1 (from left to right). Plating was a 10 μl aliquot of 10-fold serial dilutions down the plate (from top to bottom).

FIG. 4. Localization of Bot1 mRNA in barley. In situ localization of Bot1 mRNA in transverse (A to H) and longitudinal (I, J) sections of Sahara (A, C, E, G, I) and Clipper (B, D, F, H, J) barley tissues grown at 1 mM $H_3BO_3$, probed with antisense Bot1. Bot1 mRNA staining is strong at the tips of leaf blades (A, B) in mesophyll surrounding the enlarged vessels (arrowheads in B). Relative to the leaf blade tip, staining is reduced 2 cm back from the tip (C, D) but remains specific to mesophyll surrounding the enlarged vessels in Sahara (arrowhead in C). At the middle of the youngest fully emerged leaf blade (E, F) this pattern was not evident. Bot1 mRNA staining is also strong in the youngest tissue of the cylindrical sheath (G, H) and root tip (I, J). In roots, staining extended into the mature stele (arrowheads in I, J). A quantitative difference in staining between Sahara and Clipper leaf tissue sections is evident. (A to H) TEM fixative. (I, J) FAA fixative. Sense hybridizations were performed for all tissue sections and produced no detectable signal. The plant at centre is a 10 day old Clipper seedling. Scale bars: 100 μm (A to F), 500 μm (G to J). (K) Bot1 mRNA levels in 10 mm root segments taken along the root were analyzed by QPCR. Different letters above each bar represent statistically significant differences (ANOVA, $P<0.05$, post hoc Tukey test). Data are means±s.e.m. (n=3).

FIG. 5, Determination of boron tolerance locus genotypes. Molecular marker and boron tolerance genotypes of F3 recombinants are illustrated with reference to the genetic map from FIG. 2A at the top. Shaded and open bars represent Sahara and Clipper derived chromosome segments, respectively. For each F3 recombinant, an F4 progeny family was grown for 21 days in 2 mM $H_3BO_3$ and F4 individuals scored for leaf boron concentration and a linked molecular marker to follow the inheritance of recombinant and non-recombinant chromosomes. Boron concentration of individuals homozygous for recombinant or non-recombinant chromosomes (mean±s.e.m, n=6) are shown, together with the boron tolerance allele carried by these individuals as determined by boron accumulation, where T is tolerance allele and IT is intolerance allele. The homozygous non-recombinants served as internal controls to take account of genetic background segregation and allowed the QTL locus to be scored confidently. Two of the four recombinants for the xBM178-xBM160 interval were not progeny tested.

Figure 6:
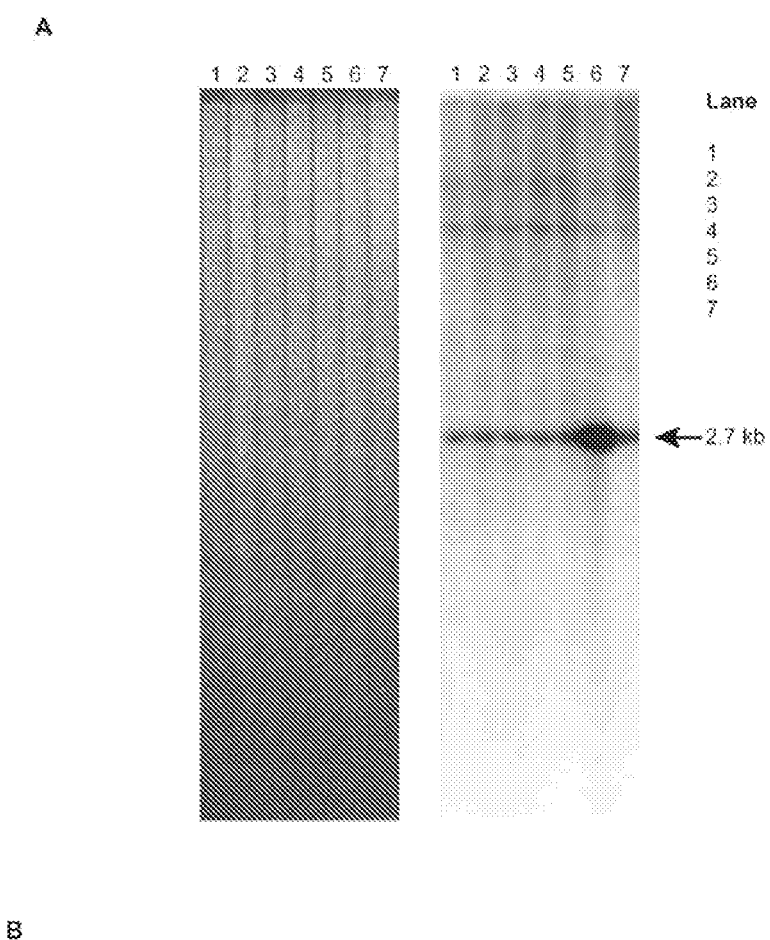
Figure 6:
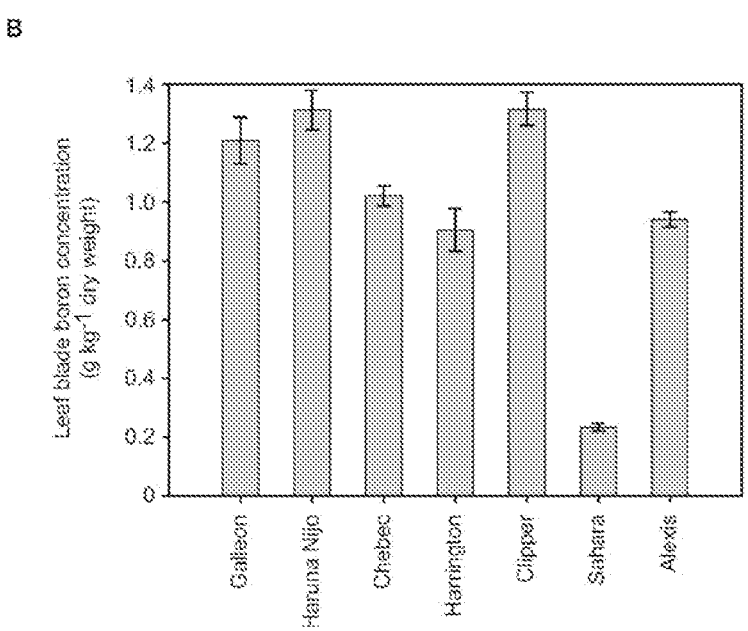

FIG. 6. Bot1 genomic Southern and boron accumulation analysis in boron tolerant and intolerant barley genotypes. (A) Genomic DNA from boron tolerant barley landrace Sahara (lane 6) and boron intolerant barley genotypes (lanes 1-5, 7) digested with Xba I (on left) was probed with a Clipper derived 559 bp [$^{32}$P]-labelled fragment from the Bot1 gene (on right). (B) Leaf blade boron concentration of the same barley genotypes grown in base hydroponics solution supplemented with $H_3BO_3$ to 2 mM for 21 days. Sahara leaf blades contain significantly less boron than those of intolerant genotypes (ANOVA, P<0.001; post-hoc Tukey test).

Figure 7:
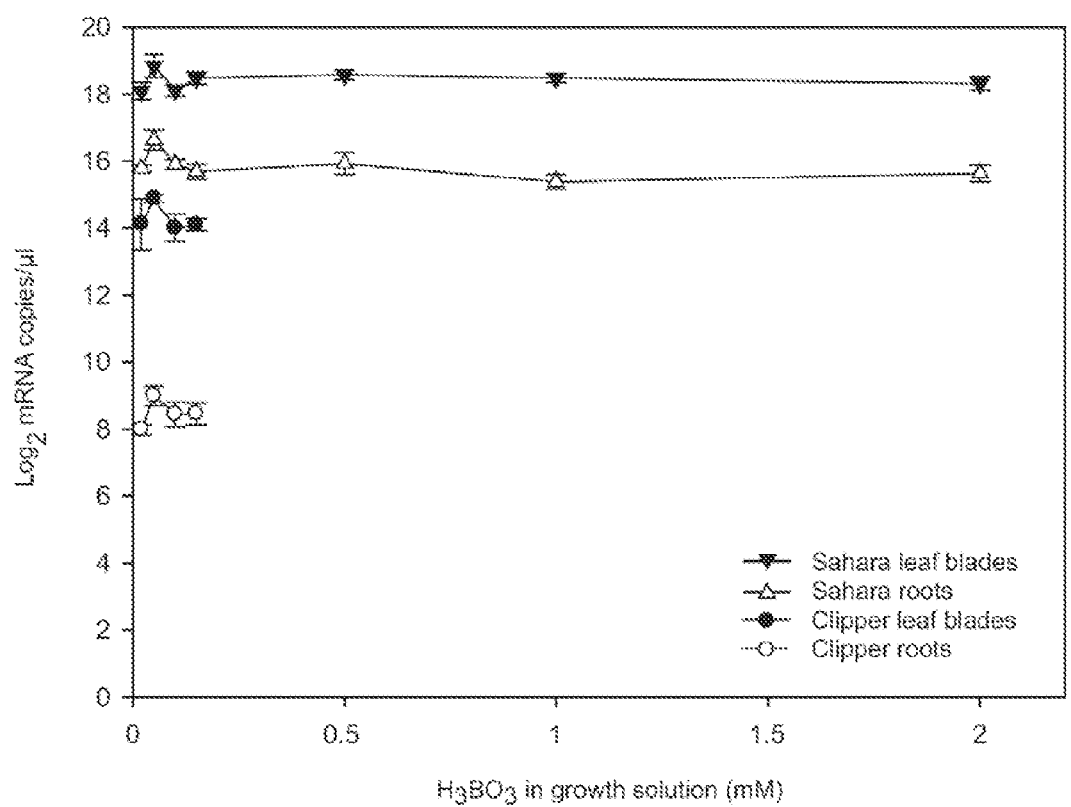

FIG. 7. Bot1 transcript levels are higher in boron tolerant barley. Bot1 transcript levels were analyzed by QPCR in leaf blades and roots of Clipper and Sahara barley grown over a range of $H_3BO_3$ concentrations. Data are means±s.e.m. (n=3).

Figure 8:
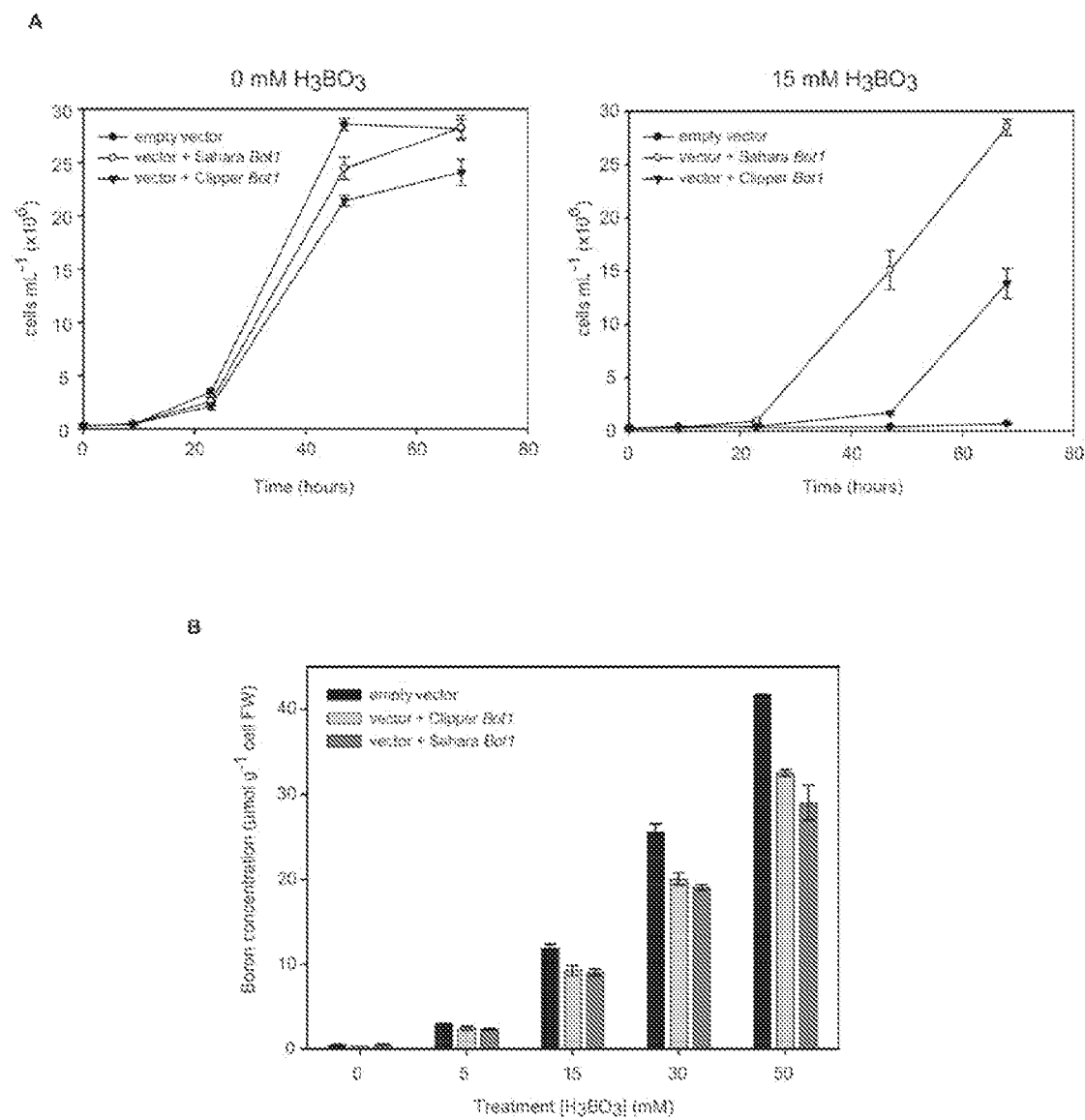

FIG. 8. Bot1 provides boron tolerance and boron efflux in yeast. (A) *Saccharomyces cerevisiae* expressing Sahara Bot1 grow faster compared to cells expressing Clipper Bot1 at high boron concentration in liquid culture, ANOVA, P<0.001. (B) *Saccharomyces cerevisiae* expressing Sahara or Clipper Bot1 maintain a lower internal cellular boron concentration than those expressing empty vector (ANOVA, P<0.05; post-hoc Tukey test). The difference between vector+clipper Bot1 and vector+Sahara Bot1 is not significant. Data are means±s.e.m. (n=3).

Figure 9:
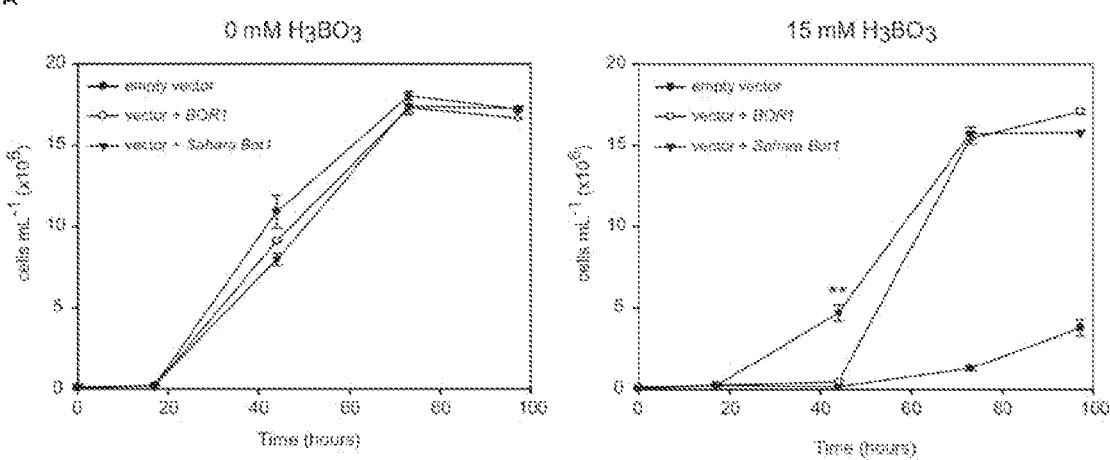
Figure 9:
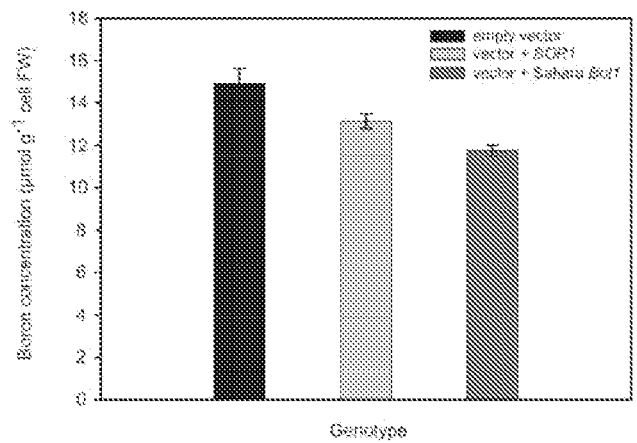

FIG. 9. Comparison of growth and boron content of yeast mutant ynl275w cells expressing BOR1 or Sahara Bot1. (A) *Saccharomyces cerevisiae* mutant ynl275w cells expressing BOR1 or Sahara Bot1 maintain growth at high boron concentration in liquid culture. Growth of cells expressing Bot1 is significantly different from cells expressing BOR1 at 44 hours. (**P<0.01, Student's t test). (B) The boron concentration of cells expressing Sahara Bot1 is significantly different from cells expressing BOR1 (P<0.05 Student's t test), Data are means±s.e.m. (n=3)

Figure 10:

FIG. 10. Bot1 sequence. (A) Sahara (boron tolerant) Bot1 cDNA and predicted protein. Boxed nucleotides and amino acids indicate positions of nucleotide and amino acid substitutions relative to the Clipper allele. Underlined amino acids indicate transmembrane helices predicted using TMHMM Server v. 2.0. (B) Structure of the Bot1 gene. Filled and open boxes indicate translated and non-translated exon sequences, respectively, while introns are shown as adjoining lines. The nucleotide sequence of Bot1 depicted in the Figure is set forth in SEQ ID NO: 4, and the amino acid sequence of Bot1 depicted in the Figure is set forth in SEQ ID NO: 2.

FIGS. 11A-11D. Bot1 sequence alignment. Alignment of Sahara Bot1 with *Arabidopsis* BOR1 (At2g47160.1) and other *Arabidopsis* and rice boron transporter-like sequences. Residues identical in all or at least six of the 12 sequences are shaded in black and grey, respectively. Bot (SEQ ID NO: 2), Os12g37840.1 (SEQ ID NO: 28), Os01g08040 (SEQ ID NO: 29), Os01g08020 (SEQ ID NO: 30), Os05g08430 (SEQ ID NO: 31), At2g47160.1 (SEQ ID NO: 32), At3g62270.1 (SEQ ID NO: 33), At3g06450.1 (SEQ ID NO: 34), At1g15460.1 (SEQ ID NO: 35), At1g74810.1 (SEQ ID NO: 36), At5g25430.1 (SEQ ID NO: 37), and At4g32510.1 (SEQ ID NO: 38).

EXAMPLE 1

Introduction

Both limiting and toxic soil concentrations of the essential micronutrient boron represent major limitations to crop production worldwide. Here we identify Bot1, a BOR1 orthologue, as the gene responsible for the superior boron toxicity tolerance of the Algerian barley landrace Sahara 3771 ('Sahara'). Bot1 was located at the tolerance locus by high-resolution mapping. Compared to intolerant genotypes, Sahara contains approximately four times as many Bot1 gene copies, produces dramatically more Bot1 transcript and encodes a Bot1 protein with a higher capacity to provide tolerance in yeast. Bot1 transcript levels identified in barley tissues are consistent with a role limiting net entry of boron into the root and in disposal of boron from leaves via hydathode guttation.

Of all plant nutrient elements, boron has the narrowest range between deficient and toxic soil solution concentration, and both boron deficiency and toxicity severely limit crop production worldwide. Toxicity is more difficult to manage agronomically and is best dealt with by using boron tolerant varieties. Genetic variation for boron toxicity tolerance is known for a number of crop plant species. Tolerance is most commonly associated with the ability to maintain low boron concentrations in the shoot. In barley (*Hordeum vulgare*), the non-agronomic but highly boron tolerant Algerian landrace Sahara was identified as a potential source of tolerance for variety improvement. In a cross between Sahara and the boron intolerant Australian malting variety Clipper, several QTL controlling tolerance were identified. The major locus on chromosome 4H affects leaf symptom expression (FIG. 1A), boron accumulation (FIG. 1B), root length response and dry matter production under boron toxic conditions. The ability of Sahara to maintain lower shoot boron accumulation is at least partially due to a mechanism of active boron efflux from the root.

EXAMPLE 2

Bot1 Mapping

Figure 2:
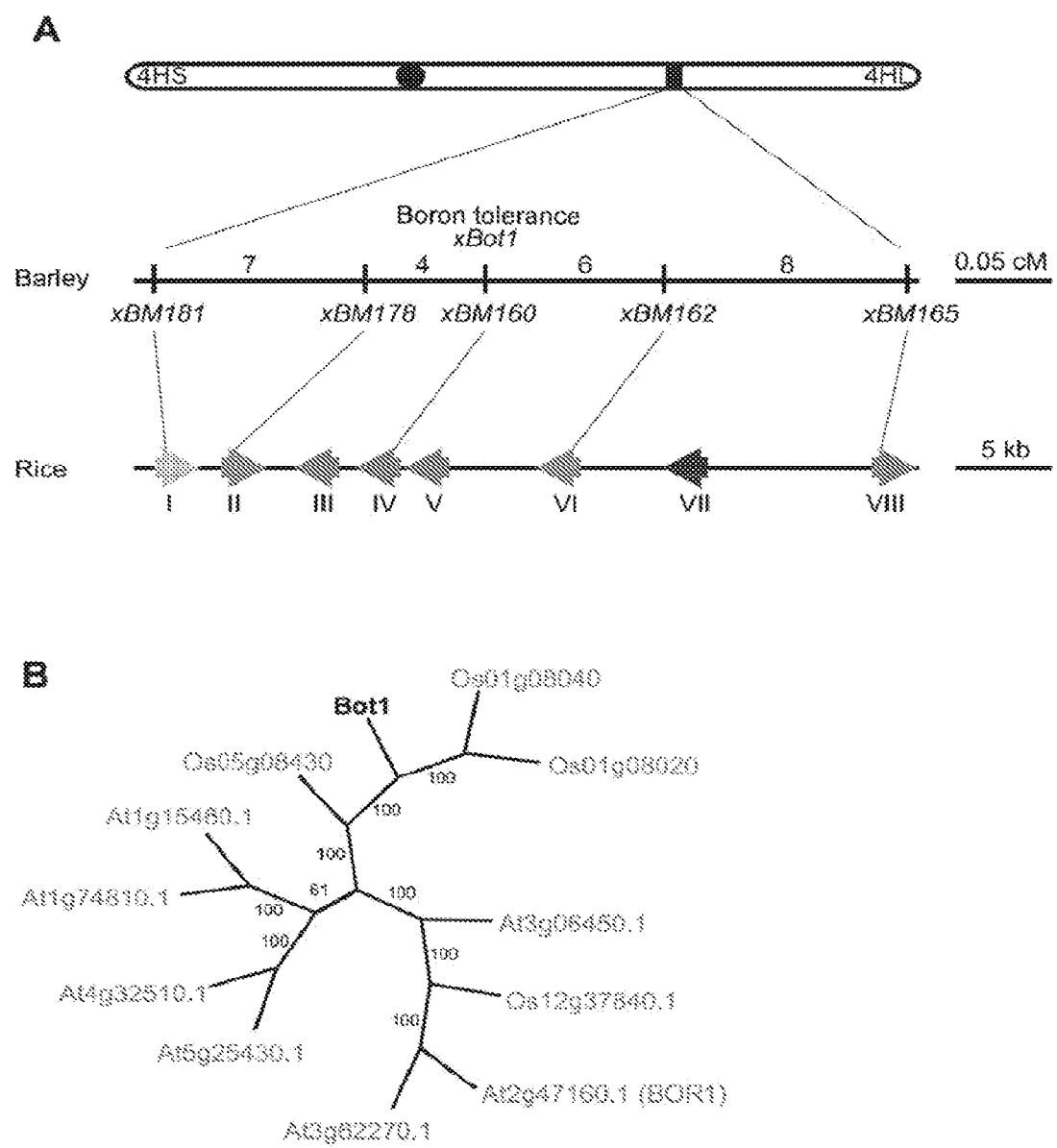
Figure 5:
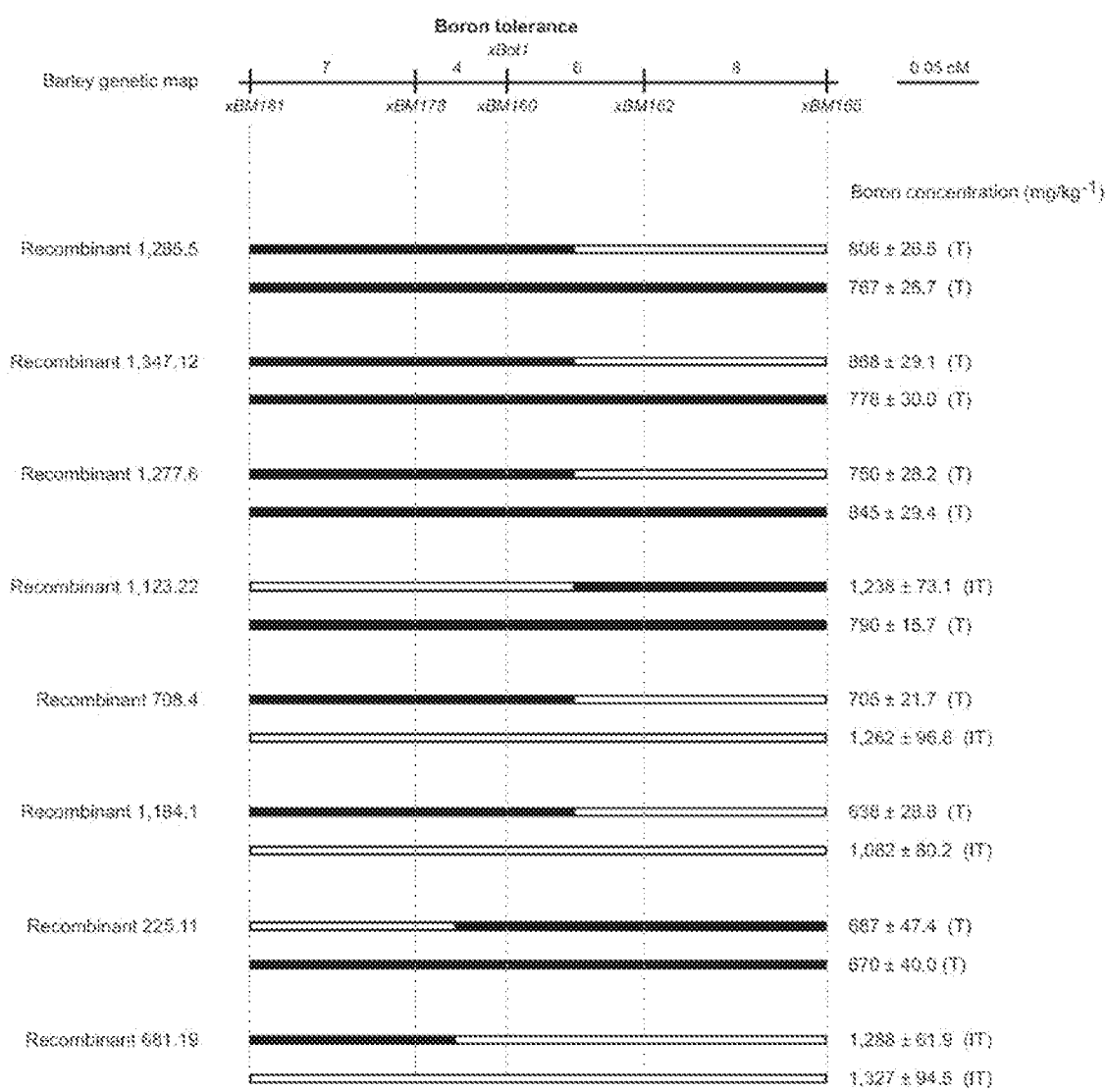

A map-based approach was used to isolate the 4H boron tolerance gene. Using a population representing 6,720 meioses, and gene colinearity with the syntenic region on rice chromosome three to generate markers, the tolerance locus was delimited to a 0.15 cM interval between markers xBM178 and xBM162 (FIGS. 2A and 5). The corresponding 11.2 kb interval in rice contains two intact copies and one 3'-truncated version of a gene showing similarity to a family of AMP-dependent synthetases and ligases, and no other predicted gene. Barley ESTs most closely matching one of the intact copies were used to derive the marker xBM160 which co-segregated with the tolerance locus.

In a parallel approach several candidate genes in barley were also mapped. These were barley genes showing similarity to the *Arabidopsis* NIP5; 1 major intrinsic protein and the *Arabidopsis* BOR1 efflux transporter related to bicarbonate transporters in animals. Both *Arabidopsis* genes are required for healthy growth under conditions of low boron supply.

However, in plants the genes involved in boron toxicity tolerance may be related to those shown to function in boron efficiency. Comparisons of barley expressed sequence tags (ESTs) revealed four BOR1 (At2g47160.1) related genes. Mapping localized one of the barley genes (Bot1) to the region of the boron tolerance QTL on 4H. Subsequently, a marker developed from the 3' end of Bot1 was found to co-segregate perfectly with the tolerance locus in the high-resolution mapping population (FIG. 2A), strongly suggesting that Bot1 encodes the boron tolerance from the 4H locus. Although barley-rice gene colinearity was found to be high in the region (FIG. 2A), the corresponding interval on rice chromosome three lacks a BOR1 orthologue and the rice gene most closely resembling Bot1 (Os01g08040; FIG. 2B) resides on chromosome one.

EXAMPLE 3

Bot1 Copy Number in Barley

Southern hybridization using a Clipper derived Bot1 probe gave a stronger signal in Sahara than in Clipper and other boron intolerant genotypes, indicating the occurrence of additional Bot1 copies in Sahara (FIG. 6). A number of restriction enzyme digests revealed hybridizing Sahara fragments of mostly a single size (e.g. Xba I, FIG. 6), suggesting that the Bot1 copies in Sahara are highly similar. With Dra I, which distinguishes the Bot1 Clipper copy from Sahara copies, all Bot1 genes could be mapped and were found to co-segregate with boron tolerance in the Clipper×Sahara F1-derived doubled-haploid population, indicating that these genes occur in a cluster. Quantitative real-time PCR (QPCR) analysis using genomic DNA as the template indicated that Sahara contains approximately four (3.8±0.17) times more copies of the gene than Clipper.

EXAMPLE 4

Bot1 Transcript Levels in Barley

QPCR performed using complementary DNA (cDNA) as template revealed that Bot1 transcript levels in Sahara were approximately 160- and 18-fold higher in roots and leaf blades, respectively, compared to Clipper (FIG. 7). Interestingly, this increase in Bot1 transcript levels exceeds the approximate four-fold increase in Bot1 copy number in Sahara, suggesting that factors additional to gene duplication may contribute to increased Bot1 transcript levels in Sahara. We performed a comparative promoter analysis between the Clipper and Sahara Bot1 alleles to search for differences that could account for the observed genotypic variation in transcript levels. Over a 1.3 kb region 5' of the mRNA transcription start site, the Clipper and Sahara Bot1 promoter regions are 96% identical. Based on database searches no significant differences were detected in known regulatory elements. More work will be required to determine the actual effect of these changes on Bot1 transcription in barley. In any case, the greater transcript levels in Sahara relative to Clipper offers an explanation for the functional difference between boron tolerance and intolerance alleles and provides additional evidence supporting Bot1 as the gene controlling boron tolerance at the 4H locus. In both roots and leaf blades, transcript levels were unaltered by exposure to a range of boron concentrations (FIG. 7). Lack of transcriptional activation of a boron tolerance mechanism is consistent with rapid boron efflux from Sahara roots observed following addition of either non-toxic or toxic quantities of boron and the similar rank order of shoot boron accumulation in different genotypes grown over a range of boron concentrations.

EXAMPLE 5

Bot1 Activity in Yeast

Figure 3:
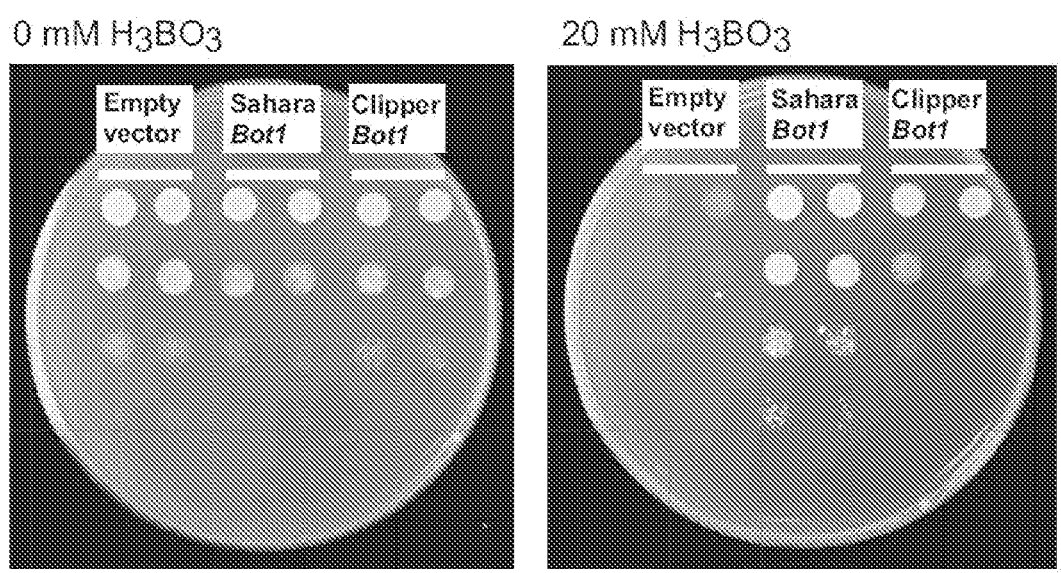

The ability of Bot1 to function as a boron transporter was confirmed in yeast (Saccharomyces cerevisiae). Initially, approximately 2 million clones from a Sahara root cDNA expression library were screened for their ability to confer boron tolerance to yeast. Three clones corresponding to Bot1 were obtained that allowed yeast to grow on high boron media. The Bot1 clones contained complete open reading frames (ORFs) and were identical in sequence. In yeast, we then compared the ability of Sahara Bot1 with that of Clipper Bot1 or Arabidopsis BOR1 to confer boron tolerance. Yeast expressing Sahara Bot1 grew better than yeast expressing Clipper Bot1 in the presence of high boron on both solid medium (FIG. 3) or in liquid culture (FIG. 8). Cells expressing either Sahara Bot1 or Clipper Bot1 also maintained approximately 24% or 20% less cellular boron, respectively, than cells expressing the empty vector control (FIG. 8). This is in spite of the fact that at physiological pH boron exists principally as undissociated boric acid (pKa1-pKa3=9.2-13.8) to which membranes are relatively permeable. Additionally, compared to BOR1 of Arabidopsis, we could show that Sahara Bot1 has higher boron efflux transport activity and capacity to provide tolerance (FIG. 9). These results confirmed that Bot1, like BOR1 of Arabidopsis, encodes a functional boron efflux transporter and that Sahara Bot1 has a higher capacity to provide boron tolerance in yeast than Clipper Bot1 or BOR1. None of the clones identified by the library screen corresponded to the tolerance co-segregating gene BM160, further supporting the notion that Bot1 and not BM160 is the tolerance gene.

EXAMPLE 6

Bot1 Sequence Analysis

The Sahara Bot1 open reading frame (SEQ ID NO: 1) is predicted to encode a 666 amino acid protein with 10-12 putative transmembrane helices (FIG. 10). Within the ORF, Clipper Bot1 (SEQ ID NO: 25) differs by 11 nucleotides, two of which result in differences to the translated protein: L305S and D592G. Residue change 305 (L; hydrophobic to S; polar) in transmembrane helix eight may impart a conformation change and residue change 592 (D; polar to G; no side chain) is likely to be located within the intracellular carboxyl terminus. Both could affect boron transport. Bot1 showed greater sequence similarity to several other Arabidopsis BOR1-related proteins than to BOR1 itself (FIGS. 2B and 11), consistent with Bot1 serving a different role to BOR1, which is required for boron efficiency. Over-expression of one of these BOR1-related genes in Arabidopsis improved boron tolerance, further supporting our hypothesis. The genomic sequence of a Bot1 gene (SEQ ID NO: 3) was obtained from a clone (accession EU176161) of a bacterial artificial chromosome (BAC) library we constructed from a barley doubled-haploid line containing the Sahara 4H boron tolerance allele. It was identical to the cDNA in the coding sequence and contained 13 exons and 12 introns, including a 941 bp intron in the 5' untranslated region (FIG. 10).

EXAMPLE 7

In Situ Hybridization

Figure 4:
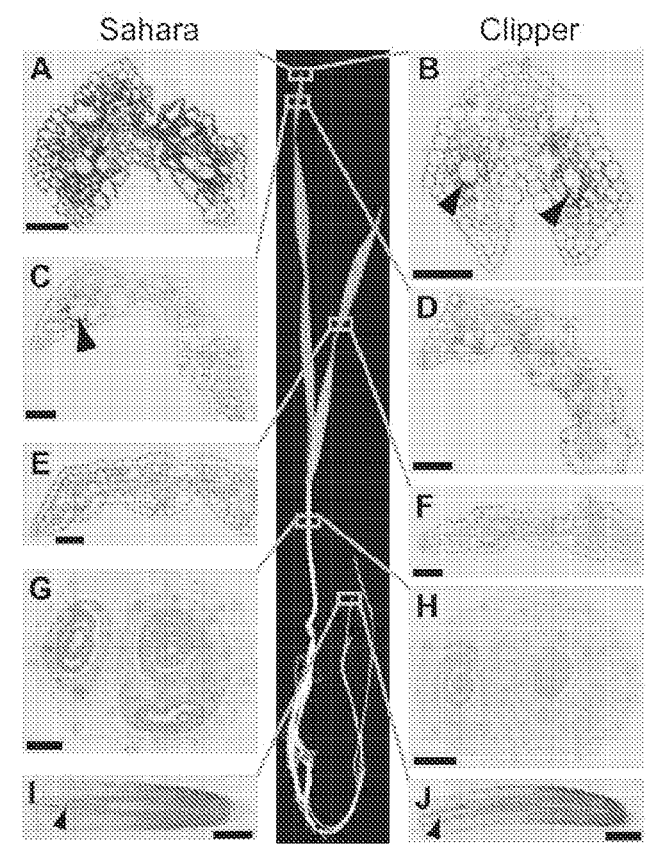
Figure 4:
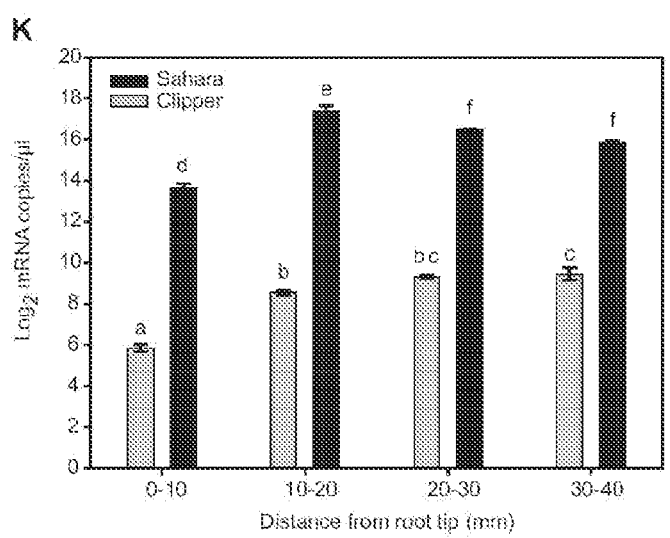

Bot1 mRNA was localized by in situ hybridization to barley root and leaf blade tissue sections (FIG. 4, A to J). In roots, staining was strongest in all cell types of the meristematic and elongation zone at the tip (FIGS. 4, I and J). Within cylindrical sheath tissues (FIGS. 4, G and H) staining was strong in all cells of the youngest leaf blades. QPCR from 10 mm segments taken along the root revealed that Bot1 mRNA level, expressed as a proportion of total RNA content, was slightly greater in more mature root segments than in end segments containing root tips (FIG. 4K). The lower levels of staining in mature root may reflect the proportionally lower volume of cytoplasm in these cells, but the significant transcript levels nevertheless observed by QPCR in mature root indicate a role for the transporter in both growing and mature sections of the root. The Bot1 mRNA detected in young cells could potentially serve the dual role of limiting symplastic boron concentration and hence toxicity, and helping to maintain a high boron supply to newly forming primary cell walls where boron forms an essential component of the pectic polysaccharide rhamnogalacturonan II. It is probable that Bot1 mRNA localization in mature roots helps efflux boron from the roots. In older leaf blades, Bot1 mRNA staining was strong in mesophyll adjacent to enlarged vessels near the margins and was strongest at the tips (FIGS. 4, A and B). In barley, leaf blade tips are the site of guttation by hydathodes. Bot1 mRNA localization here suggests an additional role of Bot1 in facilitating boron removal from the leaf blade via guttation fluid and hence in reducing boron toxicity in the leaves. Guttation has previously been shown to be a route by which substantial amounts of boron can be removed from leaves. In field conditions rainfall decreases boron concentrations in shoots of barley and wheat.

EXAMPLE 8

Materials and Methods (i) Plant Materials, Growth and Boron Analysis

Seeds of Clipper, Sahara, and F3 mapping population lines were germinated on filter paper and grown hydroponically in a base solution changed every seven days containing 5 mM $NH_4NO_3$, 5 mM $KNO_3$, 2 mM $Ca(NO_3)_2.4H_2$, 2 mM $MgSO_4.7H_2O$, 0.1 mM $KH_2PO_4$, 0.05 mM NaFe(III)EDTA, 50 µM $H_3BO_3$, 5 µM $MnCl_2.4H_2O$, 10 µM $ZnSO_4.7H_2O$, 0.5 µM $CuSO_4.5H_2O$, 0.1 µM $Na_2MoO_3$ at pH 5.0. For progeny testing, seedlings were grown in base hydroponics solution supplemented with $H_3BO_3$ to 2 mM in a glasshouse at 15° C. (night) to 23° C. (day) with a 14 hour photoperiod. All leaf blades were harvested after 21 days. Plants for QPCR, boron accumulation analysis and in situ hybridization were grown in base hydroponics solution in a controlled environment growth room at 22° C. (day) to 16° C. (night) with a 12 hour photoperiod. For QPCR and boron accumulation analysis in leaf blades, the four oldest leaf blades (excluding the first leaf blade) and the roots were harvested from 21 day old plants grown in solution containing variable amounts of supplemental $H_3BO_3$ for 14 days. For in situ hybridization and root section QPCR, leaf blades, stem and roots of plants were harvested from ten day old plants grown in base hydroponics solution supplemented with $H_3BO_3$ to a final concentration of 1 mM for seven days. Samples were analyzed for boron content by inductively coupled plasma atomic emission spectrometry or using an azomethine-H assay (Wolf, *Comm. Soil Sci. Plant Anal.* 5: 39, 1974).

(ii) Fine Mapping of Bot1

The F3 mapping population was derived from a cross between two Clipper×Sahara F1-derived doubled-haploids which differed for alleles at the boron tolerance locus on 4H but not for alleles at other known boron tolerance loci. F2 plants selected as heterozygous for the tolerance locus region were used to generate F3 seed for recombinant screening. Cleaved amplified polymorphic sequence (CAPS) markers were made for Bot1 and by using barley ESTs related to genes from the corresponding interval on rice chromosome three. Primers and restriction enzymes for CAPS markers are listed in Table 3. F3 recombinants for the region were marker selected and their tolerance genotype determined by measuring leaf blade boron accumulation in F4 progeny individuals. To enable precise scoring of the QTL locus, the same progeny plants were scored for a PCR marker to follow the inheritance of recombinant and non-recombinant 4H chromosomes, so as to confirm when the observed variation in boron accumulation was controlled by segregation at the 4H locus (see also FIG. 5).

(iii) BAC Clone Analysis

We constructed a BAC library from a Clipper×Sahara F1-derived doubled-haploid line carrying Sahara boron tolerance alleles for loci previously described, including the one on 4H (Jefferies et al., *Theor. Appl. Genet.* 98: 1293, 1999). Size-fractionated Hind III partially digested genomic DNA was ligated to pIndigoBAC-5 (Invitrogen) and transformed into *E. coli* strain DH10B. The library represents 5.3× genome equivalents, comprises 221,184 clones and has an average insert size of 120 kb. A partially sequenced BAC clone positive for a Bot1 probe also contained the xBM160 and xBM162 markers that co-segregate with and flank the 4H boron tolerance locus, respectively.

(iv) Nucleic Acid Extraction, cDNA Synthesis and Quantitative Real-Time PCR

For QPCR on cDNA to analyze Bot1 transcript levels we extracted total RNA from leaf blades and roots of hydroponically grown plants using TRIzol (Invitrogen) followed by RNeasy spin column purification incorporating DNase I treatment (Qiagen). We synthesised first-strand cDNA using Superscript III reverse transcriptase (Invitrogen) and used it as the template to amplify Bot1 transcripts. QPCR was also used to estimate Bot1 copy number in Sahara and Clipper. For each genotype, three independent PCR reactions were performed on each of five independent DNA extractions. Data were analyzed by comparing amplification of a Bot1 fragment to that of a known single copy control gene that served as an internal standard (alpha-amylase/trypsin inhibitor, accession number X13443). Primers used for cDNA and genomic DNA QPCR contained no mismatches to the Sahara or Clipper Bot1 sequences. QPCR assays were performed using methods described previously (Burton et al., *Plant Physiol.* 134: 224, 2004).

(v) Primers

Primers used for amplification of CAPS markers, QPCR products, genomic Southern probes and in situ hybridization probes are listed in Table 3.

TABLE 3

| Primers | | |
|---|---|---|
| QPCR Primers | | |
| Product | Bot1 fragment used for QPCR on cDNA | |
| Forward Primer | CAACATGAACACACATTGGAGGAAG | SEQ ID NO: 5 |
| Reverse Primer | AAGAACGACTGCCTGAGGATTTCCC | SEQ ID NO: 6 |
| Product | Bot1 fragment used for QPCR on genomic DNA | |
| Forward Primer | AGGATTGACGCTGAGATATTGGATG | SEQ ID NO: 7 |
| Reverse Primer | GTACCGTGCATATTATCACGGAAAG | SEQ ID NO: 8 |
| In situ hybridization primers | | |
| Product | Bot1 fragment used for in situ hybridization | |
| Forward Primer | GATAGAACAATGGCCCAGGACCGAC | SEQ ID NO: 9 |
| Reverse Primer | TCAAACAGAACAAAGCCAGGCACAC | SEQ ID NO: 10 |
| Genomic Southern hybridization primers | | |
| Product | Bot1 fragment used for genomic Southern hybridization | |
| Forward Primer | GATCCTTTTCCCGCTACCTTTCTTC | SEQ ID NO: 11 |
| Reverse Primer | GTACCGTGCATATTATCACGGAAAG | SEQ ID NO: 12 |
| CAPS marker primers | | |
| Product | xBM181 (restriction endonuclease: Hinf I) | |
| Forward Primer | GACCACACCGCACCTCTACAAACAG | SEQ ID NO: 13 |
| Reverse Primer | AGGAGACATACTACGAGGCGGACCC | SEQ ID NO: 14 |
| Product | xBM178 (restriction endonuclease: Hinf I) | |
| Forward Primer | TCGTCATCCCCTTCACCTGCCTCTG | SEQ ID NO: 15 |
| Reverse Primer | AGCTGGAAGGTGTTTGAACTGCAGC | SEQ ID NO: 16 |
| Product | xBM160 (restriction endonuclease: Bcg I) | |
| Forward Primer | CGGGTTCGTGGTGTACCACATCTAC | SEQ ID NO: 17 |
| Reverse Primer | GGCTGAAGATCACCGACTCCACCTC | SEQ ID NO: 18 |
| Product | xBot1 (restriction endonuclease: Pvu I) | |
| Forward Primer | GATCCTTTTCCCGCTACCTTTCTTC | SEQ ID NO: 19 |
| Reverse Primer | GTACCGTGCATATTATCACGGAAAG | SEQ ID NO: 20 |
| Product | xBM162 (restriction endonuclease: Bsp1286 I) | |
| Forward Primer | ATGCGAGCGTATTATCTCACGACTG | SEQ ID NO: 21 |
| Reverse Primer | AGTACCTCCAAGCGTAACACCCTGC | SEQ ID NO: 22 |
| Product | xBM165 (restriction endonuclease: Afl II) | |
| Forward Primer | ATGCCTCAGTGGACTGAAGAAAGAC | SEQ ID NO: 23 |
| Reverse Primer | ATCCACATAATGATGTTTGGCTGAG | SEQ ID NO: 24 |

(vi) Yeast Expression

Strains of *Saccharomyces cerevisiae* used were INVSc2 (Invitrogen) and 1169. Strain 1169 was constructed from BY4741 by insertional mutagenesis of the YNL275w ORF (Takano et al., *Nature* 420: 337, 2002; Winzeler et al., *Science* 285: 901, 1999). For the comparison of Clipper and Sahara Bot1, the strain used was in INVSc2 (Invitrogen) and the expression vector was pYES-DEST52 (Invitrogen). For the comparison of BOR1 and Sahara Bot1, the strain used was 1169 and the expression vector was pYES (Invitrogen). Yeast were propagated on synthetic dextrose minimal media or in liquid culture supplemented with amino acids. Expression was induced by the addition of 2% galactose. For boron concentration measurements, yeast cultures in the mid-log phase of growth were harvested by centrifugation and resuspended in media containing up to 50 mM $H_3BO_3$. The cells were incubated for 2 h at 30° C. with shaking, and then collected by vacuum filtration of the media through Millipore nitrocellulose membranes (0.45 μm). Intracellular boron was extracted by boiling cells in deionised water for 40 min, followed by centrifugation to remove cellular debris. Measures of yeast growth were made by determining the absorbance of aliquots of cell suspensions with a spectrophotometer at 600 nm.

(vii) mRNA In Situ Localization

DIG-labelled antisense and sense Bot1 probes were generated with a DIG RNA labelling kit (Roche Diagnostics), from a 300 bp 3' untranslated region amplified from Sahara cDNA, cloned into pSPT and sequenced to determine orientation. Tissue was fixed either in FAA (50% ethanol, 5% acetic add, 4% formaldehyde, 0.1% Tween 20) or TEM fixative (0.25% glutaraldehyde, 4% paraformaldehyde and 4% sucrose in 1× Phosphate Buffered Saline), for 4 hours at room temperature, dehydrated through an ethanol then xylene series, embedded in paraffin, and sectioned to 7 μm. After dewaxing in Histochoice (Sigma) and sequential rehydration, sections were treated with 20 μg/ml Proteinase K, post-fixed in 4% formaldehyde in 1× PBS, acetylated in 0.5% acetic anhydride in 0.1 M triethanolamine-HCl, and dehydrated through an ethanol series. In situ hybridization was performed overnight at 42° C. in hybridization buffer (50% formamide, 1× Nasalts, 10% dextran suphate, 1×Denhardt's solution, 1 μg/μl tRNA), followed by three washes in 2×SSC for 1 hour each at the same temperature. Antibody incubation and colour detection with BM Purple were carried out according to the manufacturer's instructions (Roche Diagnostics), and slides were made permanent with Crystal Mount (Sigma).

(viii) Sequence Analysis

Phylogenetic analysis was performed using the Phylogenetic Interference Package (PHYLIP) 3.63. Selecting the PMB model in PROTDIST, a protein distance matrix was calculated for putative boron transporter sequences. The tree was generated using the neighbour joining algorithm and TreeView. To estimate the confidence limits of nodes 100 bootstrap samples were generated with SEQBOOT and the majority rule consensus tree was generated by CONSENSE. The number of transmembrane helices in Bot1 (indicated in parentheses) were predicted using the following topology prediction packages; TOPPRED (10), PHD (10), HMMTOP (10), TMHMM (11), DAS (11), PolyPhobius (11-12) and MEMSTAT (12).

EXAMPLE 9

Bot1-Like Sequences in Other Plants

*Arabidopsis* (*Arabidopsis thaliana*) has seven Bot1-like genes, designated BOR1-7, while rice (*Oryza sativa*) has four predicted Bot1-like genes, named OsBOR1-4.

TABLE 4

Bot1-like genes in *Arabidopsis* and Rice.

*Arabidopsis* (*A. thaliana*)

| Gene name | AGI locus |
| --- | --- |
| BOR1 | At2g47160.1 |
| BOR2 | At3g62270.1 |
| BOR3 | At3g06450.1 |
| BOR4 | At1g15460.1 |
| BOR5 | At1g74810.1 |
| BOR6 | At5g25430.1 |
| BOR7 | At4g32510.1 |

Rice (*Oryza sativa*)

| Gene name | Locus identifier | Accession |
| --- | --- | --- |
| OsBOR1 | Os12g37840.1 | AK070617 |
| OsBOR2 | Os01g08040 | DQ421408 |
| OsBOR3 | Os01g08020 | AK072421 |
| OsBOR4 | Os05g08430 | DQ421409 |

The nucleotide and amino acid sequences of Barley Bot1, *Arabidopsis* BOR1-7 and rice OsBOR1-4 were compared. All alignments were performed using AlignX software (Vector NTI Suite 10: Informax, Bethesda, Md., USA). The determined nucleotide and amino acid sequence identities are presented below in Table 5.

TABLE 5

Sequence identities of *Bot1*-like and Bot1-like sequences

| | Nucleotide identity to Hv*Bot1*(%) | Amino Acid identity to HvBot1 (%) |
| --- | --- | --- |
| *Arabidopsis* (*A. thaliana*) | | |
| BOR1 | 58.1 | 52.5 |
| BOR2 | 58.2 | 51.3 |
| BOR3 | 55.4 | 47.4 |
| BOR4 | 63.6 | 63.8 |
| BOR5 | 62.7 | 61.8 |
| BOR6 | 59.3 | 57.5 |
| BOR7 | 60.6 | 57.8 |
| Rice (*Oryza sativa*) | | |
| OsBOR1 | 56.7 | 51.5 |
| OsBOR2 | 80.6 | 83 |
| OsBOR3 | 80.4 | 82.5 |
| OsBOR4 | 71.7 | 71.1 |

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a Bot1 nucleic acid sequence" includes a single Bot1 nucleic acid sequence as well as two or more Bot1 nucleic acid sequences; "a plant cell" includes a single cell as well as two or more cells; and so forth.

---

The claims defining the invention are as follows:

1. An isolated cDNA molecule comprising a nucleotide sequence selected from the list consisting of:
   (i) a nucleotide sequence which encodes a polypeptide comprising the amino acid sequence set forth in SEQ ID NO: 2; and
   (ii) the nucleotide sequence set forth in SEQ ID NO: 1.

2. A construct comprising the isolated cDNA molecule of claim 1.

3. The isolated cDNA molecule of claim 1 wherein the nucleotide sequence is derived from a plant.

4. A genetically modified plant cell comprising the isolated cDNA molecule according to claim 1, wherein the cDNA molecule is heterologous to the plant cell.

5. A multicellular structure comprising one or more genetically modified plant cells of claim 4.

6. The multicellular structure of claim 5 wherein the multicellular structure comprises a whole plant, plant tissue, plant organ, plant part, plant reproductive material or cultured plant tissue.

7. A method for increasing the rate and/or level of boron efflux from a cell, the method comprising increasing expression of the isolated nucleic acid molecule of claim 1 in the cell.

8. The method of claim 7, wherein the cell is a plant cell.

9. The method of claim 7 wherein increasing expression of the isolated nucleic acid molecule increases the level and/or activity of the polypeptide in the cell.

10. A method of determining if an organism is boron tolerant, the method comprising determining the expression level of the construct of claim 2 in one or more cells of the organism, wherein an increased level of expression is associated with boron tolerance in the organism, compared to a control organism that does not comprise the construct.

11. The method of claim 10 wherein the expression level is determined by determining the number of copies of the isolated nucleic acid molecule of claim 1 present in the genomic DNA of one or more cells of the organism.

12. The method of claim 10, wherein the method further comprises selecting for boron tolerant organisms.

13. The method of claim 10 wherein the organism is a plant.

14. The isolated cDNA molecule of claim 1, operably linked to a heterologous nucleic acid molecule.

15. The isolated cDNA molecule of claim 14, wherein the heterologous nucleic acid molecule is a promoter.

* * * * *

SEQUENCE LISTING

```
<160> NUMBER OF SEQ ID NOS: 38

<210> SEQ ID NO 1
<211> LENGTH: 2001
<212> TYPE: DNA
<213> ORGANISM: Hordeum vulgare

<400> SEQUENCE: 1
atggatctac tgaggaaccc cttcaaggga gtggtcgcag atgtcaaagg gagagcgcct        60
tggtacaagg acgactggct tgcagggctc cgagctggct tcgggatatt ggcacctacc       120
atgtacatat tctttgcctc cgcgctccct gtcatcgcct tcggagagca gctcagcaac       180
gaaacaaatg gtattctcag cacagttgaa accttggcat ctactgcaat atgcgggata       240
atacatgcga ttcttggagg gcagccgatg atgatcgttg gagtcgcgga acctactatt       300
ataatgtata cgtatctcta caacttcgcc aagaagcagc caggtctggg agaacggcta       360
tacttggctt gggctggatg ggtctgcatt tggactgcta tcatgttgtt tctcttggca       420
atgttcaatg cttccaatgt tataagcaga ttcacgaggg ttgcaggaga acttttggg        480 atgttgatca ccgttctctt cctgcaagaa gctatcaagg gaatcgtggg cgaattcagt       540
atgccgaaag atgctgagat atttgaccgc agttcgccga taccagtt ccaatggata        600
```

```
tatgtcaatg gcctacttgg ggttatcttc tcaattggcc tgctatacag tgcactcaag   660
actaggcggg caaggtcatg gctgtatggt ataggatggc ttaggagctt cattgccgat   720
tatggtgtcc cgcttatggt gatcgtgtgg acggcatttt cgtacgcgct accgagcggg   780
gtcccttcag gagtgcctag gagactcttc agtccacttc cttgggagtc aagttcattg   840
ggtcattgga ccgtagcaaa ggatttgttt tctgtccctc cggcatatat atttgcagcc   900
atcgtgccag ctttgatggt tgcgggactc tacttctttg atcatagtgt agcttcacag   960
ttggctcagc aacaggagtt caatctgaag aaaccttccg cctaccatta cgacattttg  1020
gtacttggat tcatggtcct actgtgtggt ttaattggca ttcctccagc aaatggagta  1080
cttcctcagt cccccatgca tacaagaagc cttgctgtcc tcaaggggca gctaatgcgc  1140
aaaaggatgc ttcgaactgc caagaaggc atgtcgaacc gtgcaagcag tttggaaatc  1200
tatggaaaga tgcatgaagt gttcatcgaa atggataata acaggatgc tgattctgtt  1260
gacaaggact tgaagagttt gaaggatgct gtgctgcgtg aaggcgacga ggatggaaaa  1320
ttggctggag aatttgatcc aagaaaacat attgaagcac atttgcctgt tcgtgtcaac  1380
gaacagagac taagcaacct gctacaatcc ttgctggttg gtggctgtgt tggagctatg  1440
ccggttatca agatgatacc gacttcagtc ctctggggtt actttgccta catggccatt  1500
gatagcctac ccgggaacca gttttgggaa aggatacaac ttttattcgt tggagcaagc  1560
cgacgctaca aggttttgga aggtccccat gcatctttg tggagtcggt gtcttcgaga  1620
acgatatatg tctttacgat ctttcagatt gtgtacttct tgatatgttt cggcacaaca  1680
tggataccga ttgccgggat ccttttcccg ctacctttct tcctcatgat tctcatcagg  1740
cagtacctgc tccccaagtt ttttgagccc aatgacttgc gggaactgga cgcggctgag  1800
tacgatgaac ttgaaggggt ccaacatgaa cacacattgg aggaagatgg ctccatttca  1860
ggaagctgcg acggcaggat tgacgctgag atattggatg aactcacaac acaccgtggg  1920
gagttgaaac acagggttgt gagccatcgt gaagaaagac ccttcaggt ccattcaaat  1980
gccgttcagc aagcgtgtg a                                              2001
```

<210> SEQ ID NO 2
<211> LENGTH: 666
<212> TYPE: PRT
<213> ORGANISM: Hordeum vulgare

<400> SEQUENCE: 2

```
Met Asp Leu Leu Arg Asn Pro Phe Lys Gly Val Val Ala Asp Val Lys
1               5                   10                  15

Gly Arg Ala Pro Trp Tyr Lys Asp Asp Trp Leu Ala Gly Leu Arg Ala
            20                  25                  30

Gly Phe Gly Ile Leu Ala Pro Thr Met Tyr Ile Phe Phe Ala Ser Ala
        35                  40                  45

Leu Pro Val Ile Ala Phe Gly Glu Gln Leu Ser Asn Glu Thr Asn Gly
    50                  55                  60

Ile Leu Ser Thr Val Glu Thr Leu Ala Ser Thr Ala Ile Cys Gly Ile
65                  70                  75                  80

Ile His Ala Ile Leu Gly Gly Gln Pro Met Met Ile Val Gly Val Ala
                85                  90                  95

Glu Pro Thr Ile Ile Met Tyr Thr Tyr Leu Tyr Asn Phe Ala Lys Lys
            100                 105                 110

Gln Pro Gly Leu Gly Glu Arg Leu Tyr Leu Ala Trp Ala Gly Trp Val
        115                 120                 125
```

-continued

```
Cys Ile Trp Thr Ala Ile Met Leu Phe Leu Leu Ala Met Phe Asn Ala
130                 135                 140

Ser Asn Val Ile Ser Arg Phe Thr Arg Val Ala Gly Glu Leu Phe Gly
145                 150                 155                 160

Met Leu Ile Thr Val Leu Phe Leu Gln Glu Ala Ile Lys Gly Ile Val
                165                 170                 175

Gly Glu Phe Ser Met Pro Lys Asp Ala Glu Ile Phe Asp Arg Ser Ser
            180                 185                 190

Pro Ile Tyr Gln Phe Gln Trp Ile Tyr Val Asn Gly Leu Leu Gly Val
        195                 200                 205

Ile Phe Ser Ile Gly Leu Leu Tyr Ser Ala Leu Lys Thr Arg Arg Ala
210                 215                 220

Arg Ser Trp Leu Tyr Gly Ile Gly Trp Leu Arg Ser Phe Ile Ala Asp
225                 230                 235                 240

Tyr Gly Val Pro Leu Met Val Ile Val Trp Thr Ala Phe Ser Tyr Ala
                245                 250                 255

Leu Pro Ser Gly Val Pro Ser Gly Val Pro Arg Arg Leu Phe Ser Pro
            260                 265                 270

Leu Pro Trp Glu Ser Ser Leu Gly His Trp Thr Val Ala Lys Asp
        275                 280                 285

Leu Phe Ser Val Pro Pro Ala Tyr Ile Phe Ala Ala Ile Val Pro Ala
290                 295                 300

Leu Met Val Ala Gly Leu Tyr Phe Phe Asp His Ser Val Ala Ser Gln
305                 310                 315                 320

Leu Ala Gln Gln Gln Glu Phe Asn Leu Lys Lys Pro Ser Ala Tyr His
                325                 330                 335

Tyr Asp Ile Leu Val Leu Gly Phe Met Val Leu Leu Cys Gly Leu Ile
            340                 345                 350

Gly Ile Pro Pro Ala Asn Gly Val Leu Pro Gln Ser Pro Met His Thr
        355                 360                 365

Arg Ser Leu Ala Val Leu Lys Gly Gln Leu Met Arg Lys Arg Met Leu
370                 375                 380

Arg Thr Ala Lys Glu Gly Met Ser Asn Arg Ala Ser Ser Leu Glu Ile
385                 390                 395                 400

Tyr Gly Lys Met His Glu Val Phe Ile Glu Met Asp Asn Lys Gln Asp
                405                 410                 415

Ala Asp Ser Val Asp Lys Asp Leu Lys Ser Leu Lys Asp Ala Val Leu
            420                 425                 430

Arg Glu Gly Asp Glu Asp Gly Lys Leu Ala Gly Glu Phe Asp Pro Arg
        435                 440                 445

Lys His Ile Glu Ala His Leu Pro Val Arg Val Asn Glu Gln Arg Leu
450                 455                 460

Ser Asn Leu Leu Gln Ser Leu Leu Val Gly Gly Cys Val Gly Ala Met
465                 470                 475                 480

Pro Val Ile Lys Met Ile Pro Thr Ser Val Leu Trp Gly Tyr Phe Ala
                485                 490                 495

Tyr Met Ala Ile Asp Ser Leu Pro Gly Asn Gln Phe Trp Glu Arg Ile
            500                 505                 510

Gln Leu Leu Phe Val Gly Ala Ser Arg Arg Tyr Lys Val Leu Glu Gly
        515                 520                 525

Pro His Ala Ser Phe Val Glu Ser Val Ser Arg Thr Ile Tyr Val
530                 535                 540

Phe Thr Ile Phe Gln Ile Val Tyr Phe Leu Ile Cys Phe Gly Thr Thr
545                 550                 555                 560
```

```
Trp Ile Pro Ile Ala Gly Ile Leu Phe Pro Leu Pro Phe Phe Leu Met
                565                 570                 575

Ile Leu Ile Arg Gln Tyr Leu Leu Pro Lys Phe Phe Glu Pro Asn Asp
            580                 585                 590

Leu Arg Glu Leu Asp Ala Ala Glu Tyr Asp Glu Leu Glu Gly Val Gln
        595                 600                 605

His Glu His Thr Leu Glu Glu Asp Gly Ser Ile Ser Gly Ser Cys Asp
    610                 615                 620

Gly Arg Ile Asp Ala Glu Ile Leu Asp Glu Leu Thr Thr His Arg Gly
625                 630                 635                 640

Glu Leu Lys His Arg Val Val Ser His Arg Glu Arg His Leu Gln
                645                 650                 655

Val His Ser Asn Ala Val Gln Pro Ser Val
                660                 665

<210> SEQ ID NO 3
<211> LENGTH: 6396
<212> TYPE: DNA
<213> ORGANISM: Hordeum vulgare

<400> SEQUENCE: 3
ttgggcacca caccacacca caacagctgc ttccaccgcc gcgccgagga gctacctacc      60
cggccgcgca ccgcttcctt cctcctcctt gccccgccgc ccgttcggat caccggtacg     120
tacgctggta cgcacgactc tctcccgtcc ccgtccgtcc gtccgcagct cggtttggtt     180
tctatggcta gctagctagt aggtccctgc tggtcgggca aggtcggcgg tgctccttcc     240
tcggcgccgc ccgcccagct cgtcatcaga tgcttcccga ccggccgccg gatggccgcc     300
attcttcgcg agaacaaaca aacgcggcga gcttttccgg cggttcctgt tccgttttca     360
cagtcttgca catgacggcc cagccccccg ccgcatgcc tcgcgtgatt gactccccac     420
gtccacgagc ggattcattc cctttccagt ttcttacggc tcgcaatatt attatgtcaa     480
ccggagtgtt gacgtctttg tgacaacaaa gttgaggcga tgagatgagc ttttcttcct     540
caagtcgtgt gcgtagagcg aaatagtttg ccccgtacga agtgccaagt tgctgtggac     600
gggcccatcc aagaacttaa tttttaatgc ttcaaaaaca atattttaaa gtttcaaaaa     660
gtagggggga aatctgtgaa aacttcacgc attcacgacg aatctatgaa atctcgttca     720
aaatattatg aattgcaagc tggacaaaaa tatcccggcc caacaaaaaa aaggcccatt     780
ttcatgcatg cattctcttg ttctacgcca cgtacgaaag tatagttatg aaaattttct     840
tgaactggtt gtaaattgta tattttgtgt gtacacattt ttcgatcttt tttgcaatgt     900
ggaaatatga tattttcccc atccccttac gtcgttctg ttggtaggta gtactactaa     960
tgctaccaac ttttttctgg tcatagtaaa actaagcaac tagatccgat gcctattgtg    1020
catataatag tacgttgagg ttgtttctct catcagctca tggatctact gaggaacccc    1080
ttcaagggag tggtcgcaga tgtcaaaggg agagcgcctt ggtacaagga cgactggctt    1140
gcagggctcc gagctggctt cgggttagtt ttccttgtat ttgcatgtat ataaacaaga    1200
aataattcct tatttaaccc tttcttaaaa aatccttccc tatttggtcc taaaaatatt    1260
tttcttccac atacgaccct taagtaaag ttgtttctta tgtgaaattt ctgtcaattt    1320
tagctattaa cggtgttaag cggaaccgaa aaagataatt ttacctttgg tggactattt    1380
gactaatttt ttcaattttg cacacaactg aagaacatat attactataa atcattaccg    1440
ttcaccaatc gaccgaagcc aatcaactct aaaagacatg cctaaataaa atgaaatacc    1500
```

```
acatctccac tacatgcatt caggagcaca cacgcggaga tcacacagtg tgtgctcgcc    1560
atgcaccacg cagctgtttt gggcgtgcta tggcccaaca tgatcgatcg ttgccctgcc    1620
acgatgccca tatatgctag ctgcaccgta gatgcctagg ccacacccac atcggctgtg    1680
ttctgctgtt ggttatgctg ccggcaacgt gccaccgtcg cgtccacagc agcacataga    1740
tggccgttgt gtatagctcg ccgagtctgc cgggtgcata cgtactggtc gtagctaccg    1800
cgcgagttgg ccggtaccac cgcaccatga ggcatgagcc tccgcgtacc gccgtcaaac    1860
cgtgcgtgtg cctattgacc tgaaccgcca tctcgtgtga cgcttacccg gcagccgtgc    1920
atggccgact ccccactgta gggaagtggg tctctcacat tcacttttgt cttctcagca    1980
tacaaaccca ggggtaaaaa cgacttttca tgtggggaac aaaataaagt ttgagtgtcg    2040
atcgaaaagg aaagaaaaac ctcttttggg ccaaaaagga atcagattt  gagaaatggt    2100 caaataagga attctctcta tgaacaaccc caaccatatc attttttagca tgtttgctga    2160 gggatttgct tatgtatgtt tcttccccttc cgatgtttgt ttgccaggat attggcacct    2220
accatgtaca tattctttgc ctccgcgctc cctgtcatcg ccttcggaga gcagctcagc    2280
aacgaaacaa gtaagagaaa atttagcatg gtcgtcttag ccgtctatat tttttttatca    2340 tgcatttgtt ttcaatcaaa tgtcagtttc ttcacaaaaa aagagaatcc attggcaaca    2400
gtcttattcc gcatgcaaaa ttaagtttga tttagtttgt ttggattttc ttaagccaca    2460
cacgatttgt ttgaatcatc catccatata ccatatttag tttatttttc aaatatgcca    2520
gaatctttcg aatatgtcag ctctttgtac tgcaggaagt acatgattct tataatgttt    2580
aatctccaaa gaatgtgtga agttcattaa ctgaatcccc cttttgcaaa aataatatta    2640
attaacttaa tccccttgat tttgtgaaca aagtgtctag tttgtttacg aaaaacgata    2700
atgtgcagta gtagttccct tttatgacac aatgcaataa tgggaggatc caatttaatc    2760
ttctgcacga taaaaaaaat caacaatcaa aggccaggat tcactacaac tcttaccact    2820
ctaggggtaa gaaggaccat tgtaaaacta cccaacatgt aaatgcttcc cctcttaatt    2880
accacactct actacacatg ggaaatttaa ttttttcgctc aatctctaaa actaagatgt    2940
gatctatttc agatggtatt ctcagcacag ttgaaaccct ggcatctact gcaatatgcg    3000
ggataataca tgcgattctt ggagggcagc cgatgatgat cgttggagtc gcggaaccta    3060
ctattataat gtatacgtat ctctacaact tcgccaagaa gcagccaggt ctgggagaac    3120
ggctatactt ggcttgggct ggatggtacg tagtatagtt taggtactaa aatagattcc    3180
accacatgat gcgatagct  ttgctattgc aaacgtaatt aaatgcatgc tctctcttga    3240
cgtgcagggt ctgcatttgg actgctatca tgttgtttct cttggcaatg ttcaatgctt    3300
ccaatgttat aagcagattc acgagggttg caggagaact ttttgggatg ttgatcaccg    3360
ttctcttcct gcaagaagct atcaaggtgt gctatcatgt ctagcaaatt aaccctagct    3420 atttttcactg tgcggaggat acttaatacg ggcactatcc atatattgca gggaatcgtg    3480
ggcgaattca gtatgccgaa agatgctgag atatttgacc gcagttcgcc gatataccag    3540
ttccaatgga tatatgtcaa tggcctactt ggggttatct tctcaattgg cctgctatac    3600
agtgcactca agactaggcg ggcaaggtca tggctgtatg gtataggttg gtcacacgtt    3660
tacttcattt atcttgttgg gtgcacttag tcggtcgatt acggtgccat tatatttgac    3720
ttgccatttg caggatggct taggagcttc attgccgatt atggtgtccc gcttatggtg    3780
atcgtgtgga cggcattttc gtacgcgcta ccgagcgggg tcccttcagg agtgcctagg    3840
agactcttca gtccacttcc ttgggagtca agttcattgg gtcattggac cgtagcaaag    3900
```

```
gtatcaattc aaattacttg tagttctaga tgtgtggata ctattcattg tcttgttagt    3960
ccaaatttag taaagcttat attacatgcc ggggttctga atgttttctt ctgggtttta    4020
ctctcaggat ttgttttctg tccctccggc atatatattt gcagccatcg tgccagcttt    4080
gatggttgcg ggactctact tctttgatca tagtgtagct tcacagttgg ctcagcaaca    4140
ggagttcaat ctgaagaaac cttccgccta ccattacgac attttggtac ttggattcat    4200
ggtacgtggt ttttacttca tttcatgtac agattctttt tctgtgagcc ttttacggt     4260 ttccttaaga acctataata accaaccttg tatgccaatg aaaagtagga taaccaattt    4320
ttattcctcg cgtctcgcgt ggtacataag aatggggatt agtgaagagt ggccataaga    4380
ggcctgcaca atacatttca cctgtgcatg gtagaaaaat tactcttacc agactgcatt    4440
ttaactccac attttaattt accatgtgat gtttcctttt ctcatagtat gtgaatggtg    4500
caggtcctac tgtgtggttt aattggcatt cctccagcaa atggagtact tcctcagtcc    4560
cccatgcata caagaagcct tgctgtcctc aaggggcagg ttagtgaaat tcagactgat    4620
ttgcgtcaca tgctaccgta gtcagaattg ctcaacccct ttctcttttt ctgtcaattt    4680
agctaatgcg caaaggatg cttcgaactg ccaaagaagg catgtcgaac cgtgcaagca     4740
gtttggaaat ctatggaaag atgcatgaag tgttcatcga aatggataat aaacaggatg    4800
tgagtttctc tatctttgtc atcttactgc ctaattttcc cttcattcat gcacaacacg    4860
tgaagtattt tgttagcaaa tgctattgca cgagttgcca aaatcacttt aaggtaaagt    4920
catgtagttg cttctgcatc cttcttttg gatagcatga tatgtgtcat attttcatgt    4980
attagttcca ttccataaag tttgtgcatt aacatttcta ttatttttat aagaatatta    5040
gaaagtaatc ttcatatcgc taaaaaaaaa ctggcacgca ggctgattct gttgacaagg    5100
acttgaagag tttgaaggat gctgtgctgc gtgaaggcga cgaggatgga aaattggctg    5160
gagaatttga tccaagaaaa catattgaag cacatttgcc tgttcgtgtc aacgaacaga    5220
gactaagcaa cctgctacaa tccttgctgg ttggtggctg tgttggagct atgccggtta    5280
tcaagatgat accgacttca gtcctctggg gttactttgc ctacatggcc attgatagcc    5340
tacccgggaa ccagttttgg gaaaggatac aactttattt cgttggagca agccgacgct    5400
acaagtaatg tctatttctg cttctgttca tcccatttga tttattgaag attcaacgat    5460
tatataacag attgcactaa tcggctattg taaacattgc agggttttgg aaggtcccca    5520
tgcatctttt gtggagtcgg tgtcttcgag aacgatatat gtctttacga tctttcagat    5580
tgtgtacttc ttgatatgtt tcggcacaac atggataccg attgccggga tccttttccc    5640
gctacctttc ttcctcatga ttctcatcag gcagtacctg ctccccaagt ttttgagcc     5700 caatgacttg cgggaactgg acgcggctga gtacgatgaa cttgaagggg tccaacatga    5760
acacacattg gtatatataa cttcagcttg tcttctccta taaaaaaaaa tcttttgttt    5820
ttgtttcatt ctctgcaatg ccccaaggtg tcggtcatcc cttattaatc tgaaactttt    5880
tggttcctcg agcaggagga agatggctcc atttcaggaa gctgcgacgg caggattgac    5940
gctgagatat tggatgaact cacaacacac cgtgggagt tgaaacacag ggttgtgagc     6000
catcgtgaag aaagacacct tcaggtccat tcaaatgccg ttcagccaag cgtgtgaaga    6060
tagaacaatg gcccaggacc gaccgaggat ttcatcaatg attctatcgg aaatgaggag    6120
ggaaatcctc aggcagtcgt tctttgccga ctgcactatt atctttccgt gataatatgc    6180
acggtactgg tagtatagca ctttccataa gacaggtagc agtgagagca gcagactgaa    6240
ggaagtattg ccggaatagc aacggtgagg agtagaaaga ttagctgagt tggtattgga    6300
```

```
ggaaaactgt ccctctgtga tctgttgttg cttgtgtgcc tggctttgtt ctgtttgagt      6360
gtaccatgtt aaaagtattg cttgataagc aacggc                                6396

<210> SEQ ID NO 4
<211> LENGTH: 2480
<212> TYPE: DNA
<213> ORGANISM: Hordeum vulgare

<400> SEQUENCE: 4
gttggcacca caccacacca caacagctgc ttccaccgcc gcgccgagga gctacctacc        60
cggccgcgca ccgcttcctt cctcctcctt gccccgccgc ccgttcggat caccgctcat       120
ggatctactg aggaaccccT tcaagggagt ggtcgcagat gtcaaaggga gagcgccttg       180
gtacaaggac gactggcttg cagggctccg agctggcttc gggatattgg cacctaccat       240
gtacatattc tttgcctccg cgctccctgt catcgccttc ggagagcagc tcagcaacga       300
aacaaatggt attctcagca cagttgaaac cttggcatct actgcaatat gcgggataat       360
acatgcgatt cttggagggc agccgatgat gatcgttgga gtcgcggaac ctactattat       420
aatgtatacg tatctctaca acttcgccaa gaagcagcca ggtctgggag aacggctata       480
cttggcttgg gctggatggg tctgcatttg gactgctatc atgttgtttc tcttggcaat       540
gttcaatgct tccaatgtta taagcagatt cacgagggtt gcaggagaac ttttgggat       600 gttgatcacc gttctcttcc tgcaagaagc tatcaaggga atcgtgggcg aattcagtat       660
gccgaaagat gctgagatat ttgaccgcag ttcgccgata taccagttcc aatggatata       720
tgtcaatggc ctacttgggg ttatcttctc aattggcctg ctatacagtg cactcaagac       780
taggcgggca aggtcatggc tgtatggtat aggatggctt aggagcttca ttgccgatta       840
tggtgtcccg cttatggtga tcgtgtggac ggcattttcg tacgcgctac cgagcggggt       900
cccttcagga gtgcctagga gactcttcag tccacttcct tgggagtcaa gttcattggg       960
tcattggacc gtagcaaagg atttgttttc tgtccctccg gcatatatat ttgcagccat      1020
cgtgccagct ttgatggttg cgggactcta cttctttgat catagtgtag cttcacagtt      1080
ggctcagcaa caggagttca atctgaagaa accttccgcc taccattacg acattttggt      1140
acttggattc atggtcctac tgtgtggttt aattggcatt cctccagcaa atggagtact      1200
tcctcagtcc cccatgcata caagaagcct tgctgtcctc aagggggcagc taatgcgcaa      1260 aaggatgctt cgaactgcca agaaggcat gtcgaaccgt gcaagcagtt tggaaatcta      1320
tggaaagatg catgaagtgt tcatcgaaat ggataataaa caggatgctg attctgttga      1380
caaggacttg aagagtttga aggatgctgt gctgcgtgaa ggcgacgagg atggaaaatt      1440
ggctggagaa tttgatccaa gaaaacatat tgaagcacat ttgcctgttc gtgtcaacga      1500
acagagacta agcaacctgc tacaatcctt gctggttggt ggctgtgttg gagctatgcc      1560
ggttatcaag atgataccga cttcagtcct ctggggttac tttgcctaca tggccattga      1620
tagcctaccc gggaaccagt tttgggaaag gatacaactt ttattcgttg gagcaagccg      1680
acgctacaag gttttggaag gtccccatgc atcttttgtg gagtcggtgt cttcgagaac      1740
gatatatgtc tttacgatct ttcagattgt gtacttcttg atatgtttcg gcacaacatg      1800
gataccgatt gccgggatcc ttttccccgct acctttcttc ctcatgattc tcatcaggca      1860
gtacctgctc cccaagtttt ttgagcccaa tgacttgcgg gaactggacg cggctgagta      1920
cgatgaactt gaagggggtcc aacatgaaca cacattggag gaagatggct ccatttcagg      1980
aagctgcgac ggcaggattg acgctgagat attggatgaa ctcacaacac accgtgggga      2040
```

```
gttgaaacac agggttgtga gccatcgtga agaaagacac cttcaggtcc attcaaatgc    2100
cgttcagcca agcgtgtgaa gatagaacaa tgggcccagga ccgaccgagg atttcatcaa    2160
tgattctatc ggaaatgagg agggaaatcc tcaggcagtc gttctttgcc gactgcacta    2220
ttatctttcc gtgataatat gcacggtact ggtagtatag cactttccat aagacaggta    2280
gcagtgagag cagcagactg aaggaagtat tgccggaata gcaacggtga ggagtagaaa    2340
gattagctga gttggtattg gaggaaaact gtccctctgt gatctgttgt tgcttgtgtg    2400
cctggctttg ttctgtttga gtgtaccatg ttaaaagtat tgcttgataa gcaacggcaa    2460
aaaaaaaaaa aaaaaaaaaa                                                2480

<210> SEQ ID NO 5
<211> LENGTH: 25
<212> TYPE: DNA
<213> ORGANISM: Artificial
<220> FEATURE:
<223> OTHER INFORMATION: oligonucleotide primer

<400> SEQUENCE: 5
caacatgaac acacattgga ggaag                                            25

<210> SEQ ID NO 6
<211> LENGTH: 25
<212> TYPE: DNA
<213> ORGANISM: Artificial
<220> FEATURE:
<223> OTHER INFORMATION: oligonucleotide primer

<400> SEQUENCE: 6
aagaacgact gcctgaggat ttccc                                            25

<210> SEQ ID NO 7
<211> LENGTH: 25
<212> TYPE: DNA
<213> ORGANISM: Artificial
<220> FEATURE:
<223> OTHER INFORMATION: oligonucleotide primer

<400> SEQUENCE: 7
aggattgacg ctgagatatt ggatg                                            25

<210> SEQ ID NO 8
<211> LENGTH: 25
<212> TYPE: DNA
<213> ORGANISM: Artificial
<220> FEATURE:
<223> OTHER INFORMATION: oligonucleotide primer

<400> SEQUENCE: 8
gtaccgtgca tattatcacg gaaag                                            25

<210> SEQ ID NO 9
<211> LENGTH: 25
<212> TYPE: DNA
<213> ORGANISM: Artificial
<220> FEATURE:
<223> OTHER INFORMATION: oligonucleotide primer

<400> SEQUENCE: 9
gatagaacaa tggcccagga ccgac                                            25

<210> SEQ ID NO 10
<211> LENGTH: 25
<212> TYPE: DNA
```

-continued

```
<213> ORGANISM: Artificial
<220> FEATURE:
<223> OTHER INFORMATION: oligonucleotide primer

<400> SEQUENCE: 10
tcaaacagaa caaagccagg cacac                                          25

<210> SEQ ID NO 11
<211> LENGTH: 25
<212> TYPE: DNA
<213> ORGANISM: Artificial
<220> FEATURE:
<223> OTHER INFORMATION: oligonucleotide primer

<400> SEQUENCE: 11
gatccttttc ccgctacctt tcttc                                          25

<210> SEQ ID NO 12
<211> LENGTH: 25
<212> TYPE: DNA
<213> ORGANISM: Artificial
<220> FEATURE:
<223> OTHER INFORMATION: oligonucleotide primer

<400> SEQUENCE: 12
gtaccgtgca tattatcacg gaaag                                          25

<210> SEQ ID NO 13
<211> LENGTH: 25
<212> TYPE: DNA
<213> ORGANISM: Artificial
<220> FEATURE:
<223> OTHER INFORMATION: oligonucleotide primer

<400> SEQUENCE: 13
gaccacaccg cacctctaca aacag                                          25

<210> SEQ ID NO 14
<211> LENGTH: 25
<212> TYPE: DNA
<213> ORGANISM: Artificial
<220> FEATURE:
<223> OTHER INFORMATION: oligonucleotide primer

<400> SEQUENCE: 14
aggagacata ctacgaggcg gaccc                                          25

<210> SEQ ID NO 15
<211> LENGTH: 25
<212> TYPE: DNA
<213> ORGANISM: Artificial
<220> FEATURE:
<223> OTHER INFORMATION: oligonucleotide primer

<400> SEQUENCE: 15
tcgtcatccc cttcacctgc ctctg                                          25

<210> SEQ ID NO 16
<211> LENGTH: 25
<212> TYPE: DNA
<213> ORGANISM: Artificial
<220> FEATURE:
<223> OTHER INFORMATION: oligonucleotide primer

<400> SEQUENCE: 16
agctggaagg tgtttgaact gcagc                                          25
```

```
<210> SEQ ID NO 17
<211> LENGTH: 25
<212> TYPE: DNA
<213> ORGANISM: Artificial
<220> FEATURE:
<223> OTHER INFORMATION: oligonucleotide primer

<400> SEQUENCE: 17
cgggttcgtg gtgtaccaca tctac                                       25

<210> SEQ ID NO 18
<211> LENGTH: 25
<212> TYPE: DNA
<213> ORGANISM: Artificial
<220> FEATURE:
<223> OTHER INFORMATION: oligonucleotide primer

<400> SEQUENCE: 18
ggctgaagat caccgactcc acctc                                       25

<210> SEQ ID NO 19
<211> LENGTH: 25
<212> TYPE: DNA
<213> ORGANISM: Artificial
<220> FEATURE:
<223> OTHER INFORMATION: oligonucleotide primer

<400> SEQUENCE: 19
gatccttttc ccgctacctt tcttc                                       25

<210> SEQ ID NO 20
<211> LENGTH: 25
<212> TYPE: DNA
<213> ORGANISM: Artificial
<220> FEATURE:
<223> OTHER INFORMATION: oligonucleotide primer

<400> SEQUENCE: 20
gtaccgtgca tattatcacg gaaag                                       25

<210> SEQ ID NO 21
<211> LENGTH: 25
<212> TYPE: DNA
<213> ORGANISM: Artificial
<220> FEATURE:
<223> OTHER INFORMATION: oligonucleotide primer

<400> SEQUENCE: 21
atgcgagcgt attatctcac gactg                                       25

<210> SEQ ID NO 22
<211> LENGTH: 25
<212> TYPE: DNA
<213> ORGANISM: Artificial
<220> FEATURE:
<223> OTHER INFORMATION: oligonucleotide primer

<400> SEQUENCE: 22
agtacctcca agcgtaacac cctgc                                       25

<210> SEQ ID NO 23
<211> LENGTH: 25
<212> TYPE: DNA
<213> ORGANISM: Artificial
<220> FEATURE:
<223> OTHER INFORMATION: oligonucleotide primer
```

```
<400> SEQUENCE: 23
atgcctcagt ggactgaaga aagac                                           25

<210> SEQ ID NO 24
<211> LENGTH: 25
<212> TYPE: DNA
<213> ORGANISM: Artificial
<220> FEATURE:
<223> OTHER INFORMATION: oligonucleotide primer

<400> SEQUENCE: 24
atccacataa tgatgtttgg ctgag                                           25

<210> SEQ ID NO 25
<211> LENGTH: 2001
<212> TYPE: DNA
<213> ORGANISM: Hordeum vulgare

<400> SEQUENCE: 25
atggatctac tgaggaaccc cttcaaggga gtggtcgcag atgtcaaagg gagagcgcct     60
tggtacaagg acgactggct tgcagggctc cgagctggct tcgggatatt ggcacctacc    120
atgtacatat tctttgcctc cgcgctccct gtcatcgcct tcggagagca gctcagcaac    180
gaaacaaatg gtattctcag cacagttgaa actttggcat ctactgcaat atgcgggata    240
atacatgcga ttcttggagg gcagccgatg atgatcgttg agtcgcggga acctactatt    300
ataatgtata cgtatctcta caacttcgcc aagaagcagc caggtctggg agaacggcta    360
tacttggctt gggctggatg ggtctgcatt tggactgcta tcatgttgtt tctcttggca    420
atgttcaatg cttccaatgt tataagcaga ttcacgaggg ttgcaggaga acttttttggg   480 atgttgatca ccgttctctt cctgcaagaa gctatcaagg gaatcgtggg cgagttcagt    540
atgccgaaag atgctgagat atttgaccgc agttcgccga tataccagtt ccaatggata    600
tatgtcaatg gcctacttgg ggttatcttc tcaattggcc tgctatacag tgcactcaag    660
actaggcggg caaggtcatg gctgtatggt ataggatggc ttaggagctt cattgccgat    720
tatggtgtcc cgcttatggt gatcgtgtgg acggcatttt cgtacgcgct accgagcggg    780
gtcccttcag gagtgcctag gagactcttc agtccacttc cttgggagtc aagttcattg    840
ggtcattgga ccgtagcaaa ggatttgttt tctgtccctc cggcatatat atttgcagcc    900
attgtgcctg cttcgatggt tgcgggactg tacttctttg atcatagtgt agcttcacag    960
ttggctcagc aacaggagtt caatctgaag aaaccttccg cctaccatta cgacattttg   1020
gtacttggat tcatggtcct actgtgtggt ttaattggca ttcctccagc aaatggagta   1080
cttcctcagt cccccatgca tacaagaagc cttgctgtcc tcaaggggca gctaatgcgc   1140
aaaaggatgc ttcgaactgc caagaaggc atgtcgaacc gtgcaagcag tttggaaatc   1200
tatggaaaga tgcatgaagt gttcatcgaa atggataata acaggatgc tgattctgtt    1260 gacaaggact tgaagagctt gaaggatgct gtgctgcgtg aaggcgacga ggatggaaaa    1320
ttggctggag aatttgatcc aagaaaacat attgaagcac atttgcctgt tcgtgtcaac    1380
gaacagagac taagcaacct gctacaatcc ttgctggttg gtggctgtgt tggagctatg    1440
ccggttatca agatgatacc gacttcggtc tctgggggtt actttgccta catggccatt    1500
gatagcctac ccgggaacca gttttgggaa aggatacaac ttttattcgt cggagcaagc    1560
cgacgctaca aggttttgga aggtccccat gcatctttg tggagtcggt gtcttcgaga    1620
acgatatatg tctttacgat ctttcagatt gtgtacttct tgatatgctt cggcacaaca   1680
```

-continued

```
tggataccga ttgccgggat ccttttcccg ctacctttct tcctcatgat tctcatcagg    1740
cagtacctgc tccccaagtt tttgagccc aatggcttgc gggaactgga cgcggctgag     1800
tacgatgaac ttgaaggggt ccaacatgaa cacacattgg aggaagatgg ctccatttca    1860
ggaagctgcg acggcaggat tgacgctgag atattggatg aactcacaac acaccgtggg    1920
gagttgaaac acagggttgt gagccatcgt gaagaaagac accttcaggt ccattcaaat    1980
gccgttcagc caagcgtgtg a                                              2001
```

<210> SEQ ID NO 26
<211> LENGTH: 666
<212> TYPE: PRT
<213> ORGANISM: Hordeum vulgare

<400> SEQUENCE: 26

| Met | Asp | Leu | Leu | Arg | Asn | Pro | Phe | Lys | Gly | Val | Val | Ala | Asp | Val | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Arg Ala Pro Trp Tyr Lys Asp Asp Trp Leu Ala Gly Leu Arg Ala
            20                  25                  30

Gly Phe Gly Ile Leu Ala Pro Thr Met Tyr Ile Phe Phe Ala Ser Ala
        35                  40                  45

Leu Pro Val Ile Ala Phe Gly Glu Gln Leu Ser Asn Glu Thr Asn Gly
 50                  55                  60

Ile Leu Ser Thr Val Glu Thr Leu Ala Ser Thr Ala Ile Cys Gly Ile
65                  70                  75                  80

Ile His Ala Ile Leu Gly Gly Gln Pro Met Met Ile Val Gly Val Ala
                85                  90                  95

Glu Pro Thr Ile Ile Met Tyr Thr Tyr Leu Tyr Asn Phe Ala Lys Lys
            100                 105                 110

Gln Pro Gly Leu Gly Glu Arg Leu Tyr Leu Ala Trp Ala Gly Trp Val
        115                 120                 125

Cys Ile Trp Thr Ala Ile Met Leu Phe Leu Leu Ala Met Phe Asn Ala
130                 135                 140

Ser Asn Val Ile Ser Arg Phe Thr Arg Val Ala Gly Glu Leu Phe Gly
145                 150                 155                 160

Met Leu Ile Thr Val Leu Phe Leu Gln Glu Ala Ile Lys Gly Ile Val
                165                 170                 175

Gly Glu Phe Ser Met Pro Lys Asp Ala Glu Ile Phe Asp Arg Ser Ser
            180                 185                 190

Pro Ile Tyr Gln Phe Gln Trp Ile Tyr Val Asn Gly Leu Leu Gly Val
        195                 200                 205

Ile Phe Ser Ile Gly Leu Leu Tyr Ser Ala Leu Lys Thr Arg Arg Ala
210                 215                 220

Arg Ser Trp Leu Tyr Gly Ile Gly Trp Leu Arg Ser Phe Ile Ala Asp
225                 230                 235                 240

Tyr Gly Val Pro Leu Met Val Ile Val Trp Thr Ala Phe Ser Tyr Ala
                245                 250                 255

Leu Pro Ser Gly Val Pro Ser Gly Val Pro Arg Arg Leu Phe Ser Pro
            260                 265                 270

Leu Pro Trp Glu Ser Ser Leu Gly His Trp Thr Val Ala Lys Asp
        275                 280                 285

Leu Phe Ser Val Pro Pro Ala Tyr Ile Phe Ala Ala Ile Val Pro Ala
        290                 295                 300

Ser Met Val Ala Gly Leu Tyr Phe Phe Asp His Ser Val Ala Ser Gln
305                 310                 315                 320

```
Leu Ala Gln Gln Glu Phe Asn Leu Lys Lys Pro Ser Ala Tyr His
            325                 330                 335

Tyr Asp Ile Leu Val Leu Gly Phe Met Val Leu Cys Gly Leu Ile
        340                 345                 350

Gly Ile Pro Pro Ala Asn Gly Val Leu Pro Gln Ser Pro Met His Thr
    355                 360                 365

Arg Ser Leu Ala Val Leu Lys Gly Gln Leu Met Arg Lys Arg Met Leu
    370                 375                 380

Arg Thr Ala Lys Glu Gly Met Ser Asn Arg Ala Ser Ser Leu Glu Ile
385                 390                 395                 400

Tyr Gly Lys Met His Glu Val Phe Ile Glu Met Asp Asn Lys Gln Asp
                405                 410                 415

Ala Asp Ser Val Asp Lys Asp Leu Lys Ser Leu Lys Asp Ala Val Leu
            420                 425                 430

Arg Glu Gly Asp Glu Asp Gly Lys Leu Ala Gly Glu Phe Asp Pro Arg
        435                 440                 445

Lys His Ile Glu Ala His Leu Pro Val Arg Val Asn Glu Gln Arg Leu
    450                 455                 460

Ser Asn Leu Leu Gln Ser Leu Leu Val Gly Cys Val Gly Ala Met
465                 470                 475                 480

Pro Val Ile Lys Met Ile Pro Thr Ser Val Leu Trp Gly Tyr Phe Ala
                485                 490                 495

Tyr Met Ala Ile Asp Ser Leu Pro Gly Asn Gln Phe Trp Glu Arg Ile
            500                 505                 510

Gln Leu Leu Phe Val Gly Ala Ser Arg Arg Tyr Lys Val Leu Glu Gly
        515                 520                 525

Pro His Ala Ser Phe Val Glu Ser Val Ser Ser Arg Thr Ile Tyr Val
    530                 535                 540

Phe Thr Ile Phe Gln Ile Val Tyr Phe Leu Ile Cys Phe Gly Thr Thr
545                 550                 555                 560

Trp Ile Pro Ile Ala Gly Ile Leu Phe Pro Leu Pro Phe Phe Leu Met
                565                 570                 575

Ile Leu Ile Arg Gln Tyr Leu Leu Pro Lys Phe Phe Glu Pro Asn Gly
            580                 585                 590

Leu Arg Glu Leu Asp Ala Ala Glu Tyr Asp Glu Leu Glu Gly Val Gln
        595                 600                 605

His Glu His Thr Leu Glu Glu Asp Gly Ser Ile Ser Gly Ser Cys Asp
    610                 615                 620

Gly Arg Ile Asp Ala Glu Ile Leu Asp Glu Leu Thr Thr His Arg Gly
625                 630                 635                 640

Glu Leu Lys His Arg Val Val Ser His Arg Glu Glu Arg His Leu Gln
                645                 650                 655

Val His Ser Asn Ala Val Gln Pro Ser Val
            660                 665

<210> SEQ ID NO 27
<211> LENGTH: 19
<212> TYPE: DNA
<213> ORGANISM: Artificial Sequence
<220> FEATURE:
<223> OTHER INFORMATION: UAS sequence

<400> SEQUENCE: 27
cggagtactg tcctccgag                                               19

<210> SEQ ID NO 28
```

```
<211> LENGTH: 711
<212> TYPE: PRT
<213> ORGANISM: Oryza sativa

<400> SEQUENCE: 28
```

| Met<br>1 | Glu | Glu | Ser | Phe<br>5 | Val | Pro | Leu | Arg | Gly<br>10 | Ile | Lys | Asn | Asp | Leu<br>15 | His |
|---|---|---|---|---|---|---|---|---|---|---|---|---|---|---|---|
| Gly | Arg | Leu | Gln<br>20 | Cys | Tyr | Lys | Gln | Asp<br>25 | Trp | Thr | Gly | Gly | Phe<br>30 | Arg | Ala |
| Gly | Ile | Arg<br>35 | Ile | Leu | Ala | Pro | Thr<br>40 | Thr | Tyr | Ile | Phe | Phe<br>45 | Ala | Ser | Ala |
| Ile | Pro<br>50 | Val | Ile | Ser | Phe | Gly<br>55 | Glu | Gln | Leu | Glu | Arg<br>60 | Asn | Thr | Asp | Gly |
| Val<br>65 | Leu | Thr | Ala | Val | Gln<br>70 | Thr | Leu | Ala | Ser | Thr<br>75 | Ala | Leu | Cys | Gly | Ile<br>80 |
| Ile | His | Ser | Phe | Leu<br>85 | Gly | Gly | Gln | Pro | Leu<br>90 | Leu | Ile | Leu | Gly | Val<br>95 | Ala |
| Glu | Pro | Thr | Val<br>100 | Leu | Met | Tyr | Thr | Phe<br>105 | Met | Phe | Asn | Phe | Ala<br>110 | Lys | Asp |
| Arg | Pro | Asp<br>115 | Leu | Gly | Arg | Arg | Leu<br>120 | Phe | Leu | Ala | Trp | Thr<br>125 | Gly | Trp | Val |
| Cys | Val<br>130 | Trp | Thr | Ala | Ile | Leu<br>135 | Leu | Phe | Leu | Leu | Ala<br>140 | Ile | Leu | Gly | Ala |
| Cys<br>145 | Ser | Ile | Ile | Asn | Arg<br>150 | Phe | Thr | Arg | Ile | Ala<br>155 | Gly | Glu | Leu | Phe | Gly<br>160 |
| Leu | Leu | Ile | Ala | Met<br>165 | Leu | Phe | Met | Gln | Gln<br>170 | Ala | Ile | Lys | Gly | Leu<br>175 | Val |
| Asp | Glu | Phe | Arg<br>180 | Ile | Pro | Glu | Arg | Glu<br>185 | Asn | Arg | Lys | Ala | Leu<br>190 | Glu | Phe |
| Val | Ser | Ser<br>195 | Trp | Arg | Phe | Ala | Asn<br>200 | Gly | Met | Phe | Ala | Ile<br>205 | Val | Leu | Ser |
| Phe | Gly<br>210 | Leu | Leu | Leu | Thr | Ala<br>215 | Leu | Arg | Ser | Arg | Lys<br>220 | Ala | Arg | Ser | Trp |
| Arg<br>225 | Tyr | Gly | Thr | Gly | Trp<br>230 | Leu | Arg | Gly | Phe | Ile<br>235 | Ala | Asp | Tyr | Gly | Val<br>240 |
| Pro | Leu | Met | Val | Leu<br>245 | Val | Trp | Thr | Gly | Val<br>250 | Ser | Tyr | Ile | Pro | Tyr<br>255 | Gly |
| Ser | Val | Pro | Lys<br>260 | Gly | Ile | Pro | Arg | Arg<br>265 | Leu | Phe | Ser | Pro | Asn<br>270 | Pro | Trp |
| Ser | Pro | Gly<br>275 | Ala | Tyr | Asp | Asn | Trp<br>280 | Thr | Val | Ile | Arg | Asp<br>285 | Met | Pro | Asn |
| Val | Pro<br>290 | Leu | Leu | Tyr | Ile | Ile<br>295 | Gly | Ala | Phe | Ile | Pro<br>300 | Ala | Thr | Met | Ile |
| Ala<br>305 | Val | Leu | Tyr | Tyr | Phe<br>310 | Asp | His | Ser | Val | Ala<br>315 | Ser | Gln | Leu | Ala | Gln<br>320 |
| Gln | Lys | Glu | Phe | Asn<br>325 | Leu | Arg | Lys | Pro | Pro<br>330 | Ser | Phe | His | Tyr | Asp<br>335 | Leu |
| Leu | Leu | Leu | Gly<br>340 | Phe | Leu | Thr | Leu | Leu<br>345 | Cys | Gly | Leu | Ile | Gly<br>350 | Ile | Pro |
| Pro | Ala | Asn<br>355 | Gly | Val | Ile | Pro | Gln<br>360 | Ser | Pro | Met | His | Thr<br>365 | Lys | Ser | Leu |
| Ala | Thr<br>370 | Leu | Lys | His | Gln | Leu<br>375 | Leu | Arg | Asn | Arg | Leu<br>380 | Val | Ala | Thr | Ala |
| Arg<br>385 | Gln | Ser | Met | Ser | Gln<br>390 | Asn | Ala | Ser | Leu | Ser<br>395 | Gln | Leu | Tyr | Gly | Ser<br>400 |

Met Gln Glu Ala Tyr Gln Gln Met Gln Thr Pro Leu Ile Tyr Gln Gln
                    405                 410                 415

Pro Ser Val Lys Gly Leu Asn Glu Leu Lys Asp Ser Thr Val Gln Met
                420                 425                 430

Ala Ser Ser Met Gly Asn Ile Asp Ala Pro Val Asp Glu Thr Val Phe
            435                 440                 445

Asp Ile Glu Lys Glu Ile Asp Asp Leu Pro Ile Glu Val Lys Glu
        450                 455                 460

Gln Arg Leu Ser Asn Leu Leu Gln Ala Thr Met Val Gly Gly Cys Val
465                 470                 475                 480

Ala Ala Met Pro Leu Leu Lys Lys Ile Pro Thr Ser Val Leu Trp Gly
                485                 490                 495

Tyr Phe Ala Phe Met Ala Ile Glu Ser Leu Pro Gly Asn Gln Phe Trp
                500                 505                 510

Glu Arg Ile Leu Leu Leu Phe Thr Ala Pro Ser Arg Arg Tyr Lys Val
            515                 520                 525

Leu Glu Glu Tyr His Thr Thr Phe Val Glu Thr Val Pro Phe Lys Thr
        530                 535                 540

Ile Ala Met Phe Thr Leu Phe Gln Thr Met Tyr Leu Leu Val Cys Phe
545                 550                 555                 560

Gly Ile Thr Trp Ile Pro Ile Ala Gly Val Leu Phe Pro Leu Met Ile
                565                 570                 575

Met Leu Leu Val Pro Val Arg Gln Tyr Ile Leu Pro Lys Leu Phe Lys
            580                 585                 590

Gly Ala His Leu Thr Asp Leu Asp Ala Ala Glu Tyr Glu Glu Ser Pro
        595                 600                 605

Ala Ile Pro Phe Ile Ala Ala Gln Asp Ile Asp Val Ala Leu Ala Arg
610                 615                 620

Thr Gln Ser Ala Glu Ile Leu Asp Asp Ile Val Thr Arg Ser Arg Gly
625                 630                 635                 640

Glu Ile Lys Arg Leu Asn Ser Pro Lys Ile Thr Ser Ser Gly Gly Thr
                645                 650                 655

Pro Val Ala Glu Leu Lys Gly Ile Arg Ser Pro Cys Ile Ser Glu Arg
            660                 665                 670

Ala Tyr Ser Pro Cys Ile Thr Glu Leu Arg His Asp Arg Ser Pro Leu
        675                 680                 685

Gly Gly Arg Gly Ser Pro Arg Thr Gly Glu Thr Arg Ser Ser Lys Leu
690                 695                 700

Gly Glu Gly Ser Thr Pro Lys
705                 710

<210> SEQ ID NO 29
<211> LENGTH: 672
<212> TYPE: PRT
<213> ORGANISM: Oryza sativa

<400> SEQUENCE: 29

Met Asp Leu Leu Arg Thr Pro Phe Lys Gly Val Val Ala Asp Ile Glu
1               5                   10                  15

Gly Arg Val Ala Trp Tyr Lys His Asp Trp Val Ala Gly Phe Arg Ser
                20                  25                  30

Gly Phe Arg Ile Leu Ala Pro Thr Met Tyr Ile Phe Phe Ala Ser Ala
            35                  40                  45

Leu Pro Val Ile Ala Phe Gly Ala Gln Leu Ser Arg Glu Thr Asn Gly
        50                  55                  60

```
Ile Leu Thr Thr Val Glu Thr Leu Ala Ser Thr Ala Leu Cys Gly Ile
 65                  70                  75                  80

Ile His Ser Ile Leu Gly Gly Gln Pro Leu Leu Ile Val Gly Val Ala
                 85                  90                  95

Glu Pro Thr Ile Ile Met Tyr Thr Tyr Leu Tyr Asn Phe Ala Lys Asn
            100                 105                 110

Gln Gln Ala Leu Gly Glu Arg Leu Tyr Leu Ala Trp Ala Gly Trp Val
        115                 120                 125

Cys Ile Trp Thr Ala Leu Met Leu Phe Leu Leu Ala Met Phe Asn Ala
    130                 135                 140

Ser Asn Val Ile Ser Arg Phe Thr Arg Val Ala Gly Glu Leu Phe Gly
145                 150                 155                 160

Met Leu Ile Thr Val Leu Phe Leu Gln Gln Ala Ile Lys Gly Ile Ile
                165                 170                 175

Glu Glu Phe Lys Val Pro Arg Asp Ala Asp His Ser Ser Pro Ile Tyr
            180                 185                 190

Gln Phe Gln Trp Leu Tyr Val Asn Gly Leu Leu Gly Val Ile Phe Ser
        195                 200                 205

Ile Gly Leu Leu Tyr Thr Ala Leu Arg Ser Arg Ala Arg Ser Trp
    210                 215                 220

Val Tyr Gly Gln Gly Trp Leu Arg Gly Phe Ile Ala Asp Tyr Gly Val
225                 230                 235                 240

Pro Leu Met Val Ile Val Trp Thr Ala Phe Ser Tyr Thr Leu Pro Lys
                245                 250                 255

Asp Val Pro Ser Gly Val Pro Arg Arg Leu Phe Ser Pro Leu Pro Trp
            260                 265                 270

Glu Ser Ser Ser Leu Gln His Trp Thr Val Ala Lys Asp Leu Phe Ser
        275                 280                 285

Val Pro Pro Ala Tyr Ile Phe Ala Ala Ile Leu Pro Ala Leu Met Val
    290                 295                 300

Ala Gly Leu Tyr Phe Phe Asp His Ser Val Ala Ser Gln Leu Ala Gln
305                 310                 315                 320

Gln Lys Glu Phe Asn Leu Lys Lys Pro Ser Ala Tyr His Tyr Asp Ile
                325                 330                 335

Leu Val Leu Gly Phe Met Val Leu Leu Cys Gly Leu Ile Gly Ile Pro
            340                 345                 350

Pro Ser Asn Gly Val Leu Pro Gln Ser Pro Met His Thr Arg Ser Leu
        355                 360                 365

Ala Val Leu Lys Gly Gln Leu Leu Arg Lys Lys Met Val Gln Thr Ala
    370                 375                 380

Asn Glu Gly Leu Met Asn Arg Ala Ser Ser Leu Glu Ile Tyr Gly Lys
385                 390                 395                 400

Ile Gln Gly Val Phe Ile Glu Met Asp Cys Glu Lys Asn Thr Asp Ser
                405                 410                 415

Val Asp Lys Glu Leu Lys Ser Leu Lys Asp Ala Ile Leu Gln Glu Val
            420                 425                 430

Asp Lys Glu Gly Thr Leu Ala Glu Glu Phe Asp Pro Ile Lys His Ile
        435                 440                 445

Glu Ala His Leu Pro Val Arg Val Asn Glu Gln Arg Leu Ser Asn Leu
    450                 455                 460

Leu Gln Ser Leu Leu Val Gly Ala Cys Val Gly Ala Met Pro Val Ile
465                 470                 475                 480

Lys Met Ile Pro Thr Ser Val Leu Trp Gly Tyr Phe Ala Tyr Met Ala
```

-continued

```
                485                 490                 495
Ile Asp Ser Leu Pro Gly Asn Gln Phe Trp Glu Arg Leu Arg Leu Ile
            500                 505                 510

Phe Ile Pro Ser Ser Arg Arg Tyr Lys Val Leu Glu Gly Pro His Ala
            515                 520                 525

Ser Phe Met Glu Ser Val Pro Ser Lys Thr Ile Thr Val Phe Thr Ile
            530                 535                 540

Phe Gln Leu Val Tyr Leu Leu Ile Cys Phe Gly Ile Thr Trp Ile Pro
545                 550                 555                 560

Ile Ala Gly Ile Leu Phe Pro Leu Pro Phe Phe Leu Met Ile Leu Ile
                565                 570                 575

Arg Gln His Val Leu Pro Lys Phe Phe Glu Pro Asn Asp Leu Arg Glu
                580                 585                 590

Leu Asp Ala Ala Glu Tyr Glu Glu Leu Glu Gly Val His His Asp His
                595                 600                 605

Thr Leu Glu Asp Gly Glu Ser Asp Ser Gly Ser Cys Gly Ser Arg Asp
            610                 615                 620

Asp Ala Glu Ile Phe Asp Glu Leu Thr Thr Asn Arg Gly Glu Leu Lys
625                 630                 635                 640

His Arg Thr Ser Ser His Arg Glu Glu Arg His Leu Gln Val His Ser
                645                 650                 655

Asn Ala Ile Gln Pro Arg Cys Gly Asp Thr Glu Asn Leu Ser Glu Cys
                660                 665                 670

<210> SEQ ID NO 30
<211> LENGTH: 672
<212> TYPE: PRT
<213> ORGANISM: Oryza sativa

<400> SEQUENCE: 30

Met Glu Leu Leu Lys Ile Pro Phe Lys Gly Val Val Ala Asp Ile Glu
1               5                   10                  15

Gly Arg Ala Ala Trp Tyr Lys His Asp Trp Leu Glu Gly Phe His Ser
            20                  25                  30

Gly Phe Arg Ile Leu Ala Pro Thr Met Tyr Ile Phe Phe Ala Ser Ala
        35                  40                  45

Leu Pro Val Ile Ala Phe Gly Thr Gln Leu Ser Arg Glu Thr Asn Gly
    50                  55                  60

Ile Leu Thr Thr Val Glu Thr Leu Ala Ser Thr Ala Ile Cys Gly Ile
65                  70                  75                  80

Ile His Ser Ile Leu Gly Gly Gln Pro Leu Leu Ile Val Gly Val Ala
                85                  90                  95

Glu Pro Thr Ile Ile Met Tyr Thr Tyr Leu Tyr Asn Phe Ala Lys Asn
            100                 105                 110

Gln Gln Ala Leu Gly Glu Arg Leu Tyr Leu Ala Trp Ala Gly Trp Val
        115                 120                 125

Cys Ile Trp Thr Ala Ile Met Leu Phe Leu Leu Ala Met Phe Asn Ala
    130                 135                 140

Ser Asn Val Ile Ser Arg Phe Thr Arg Val Ala Gly Glu Leu Phe Gly
145                 150                 155                 160

Met Leu Ile Thr Val Leu Phe Leu Gln Gln Ala Ile Lys Gly Ile Ile
                165                 170                 175

Glu Glu Phe Lys Val Pro Gly Gly Val Asp His Ser Ser Pro Ile Tyr
            180                 185                 190

Arg Phe Gln Trp Leu Tyr Val Asn Gly Leu Leu Gly Val Ile Phe Ser
```

```
            195                 200                 205
Ile Gly Leu Leu Tyr Thr Ala Leu Arg Ser Arg Ala Arg Ser Trp
210                 215                 220

Val Tyr Gly Gln Gly Trp Leu Arg Gly Phe Ile Ser Asp Tyr Gly Val
225                 230                 235                 240

Pro Leu Met Val Ile Val Trp Thr Ala Leu Ser Tyr Ala Leu Pro Lys
                    245                 250                 255

Asp Val Pro Ser Gly Val Pro Arg Arg Leu Phe Ser Pro Leu Pro Trp
                260                 265                 270

Glu Ser Ser Ser Leu His His Trp Thr Ile Ala Lys Asp Leu Phe Ser
        275                 280                 285

Val Pro Pro Ala Tyr Ile Phe Ala Ala Ile Leu Pro Ala Leu Met Ile
290                 295                 300

Ala Gly Leu Tyr Phe Phe Asp His Ser Val Ala Ser Gln Leu Ala Gln
305                 310                 315                 320

Gln Lys Glu Phe Asn Leu Lys Lys Pro Ser Ala Tyr His Tyr Asp Ile
                325                 330                 335

Leu Val Leu Gly Phe Met Val Leu Leu Cys Gly Leu Ile Gly Ile Pro
                340                 345                 350

Pro Ser Asn Gly Val Leu Pro Gln Ser Pro Met His Thr Arg Ser Leu
        355                 360                 365

Ala Val Leu Lys Gly Gln Leu Leu Arg Lys Lys Met Val Gln Thr Ala
370                 375                 380

Asn Glu Gly Leu Met Asn Arg Ala Ser Ser Leu Glu Ile Tyr Gly Lys
385                 390                 395                 400

Met Gln Gly Val Phe Ile Glu Met Asp Cys Glu Lys Asn Thr Asp Ser
                405                 410                 415

Val Asp Lys Glu Leu Lys Ser Leu Lys Asp Ala Met Leu Gln Glu Gly
                420                 425                 430

Asp Lys Glu Gly Thr Leu Ala Glu Glu Phe Asp Pro Ile Lys His Ile
                435                 440                 445

Glu Ala His Leu Pro Val Arg Val Asn Glu Gln Arg Leu Ser Asn Leu
        450                 455                 460

Leu Gln Ser Leu Leu Val Gly Ala Cys Val Gly Ala Met Pro Val Ile
465                 470                 475                 480

Lys Met Ile Pro Thr Ser Val Leu Trp Gly Tyr Phe Ala Tyr Met Ala
                485                 490                 495

Ile Asp Ser Leu Pro Gly Asn Gln Phe Trp Glu Arg Ile Arg Leu Ile
                500                 505                 510

Phe Ile Pro Ser Ser Arg Arg Tyr Lys Val Leu Glu Gly Pro His Ala
                515                 520                 525

Ser Phe Met Glu Ser Val Pro Ser Lys Thr Ile Thr Val Phe Thr Ile
        530                 535                 540

Phe Gln Leu Val Tyr Leu Leu Ile Cys Phe Gly Ile Thr Trp Ile Pro
545                 550                 555                 560

Ile Ala Gly Ile Leu Phe Pro Leu Pro Phe Phe Leu Met Ile Leu Ile
                565                 570                 575

Arg Gln His Val Leu Pro Lys Phe Phe Glu Pro Asn Asp Leu Arg Glu
                580                 585                 590

Leu Asp Ala Ala Glu Tyr Glu Glu Leu Glu Gly Val His Asp His
        595                 600                 605

Thr Leu Glu Asp Gly Ala Ser Asp Ser Glu Ser Cys Gly Ser Arg Asp
        610                 615                 620
```

```
Asp Ala Glu Ile Leu Asp Glu Leu Thr Thr Asn Arg Gly Glu Leu Lys
625                 630                 635                 640

His Arg Thr Phe Asn His Arg Glu Glu Arg His Pro Gln Ala His Thr
                645                 650                 655

Lys Ala Val Gln Pro Arg Cys Gly Asp Thr Glu Asn Trp Ser Glu Cys
            660                 665                 670

<210> SEQ ID NO 31
<211> LENGTH: 677
<212> TYPE: PRT
<213> ORGANISM: Oryza sativa

<400> SEQUENCE: 31

Met Thr Gly Thr Val Lys Ala Pro Phe Glu Gly Val Val Asn Asp Phe
1               5                   10                  15

Lys Gly Arg Leu Ser Cys Tyr Lys Gln Asp Trp Ile Asp Gly Phe Arg
            20                  25                  30

Thr Gly Phe Arg Ile Leu Ala Pro Thr Leu Tyr Ile Phe Phe Ala Ser
        35                  40                  45

Ala Leu Pro Val Val Ala Phe Gly Glu Gln Leu Ser Asn Asp Thr Asp
50                  55                  60

Gly Ala Leu Thr Thr Val Glu Thr Leu Ala Ser Thr Ala Ile Cys Gly
65                  70                  75                  80

Ile Ile His Ser Ile Leu Gly Gly Gln Pro Leu Leu Ile Val Gly Val
                85                  90                  95

Ala Glu Pro Thr Ile Ile Met Tyr Thr Tyr Ile Tyr Asn Phe Ala Lys
            100                 105                 110

Asn His Pro Asn Leu Gly Glu Arg Leu Phe Leu Pro Trp Ala Gly Trp
        115                 120                 125

Val Cys Ile Trp Thr Ala Phe Met Leu Phe Leu Met Ala Met Phe Asn
130                 135                 140

Ala Ala Val Val Ile Asn Arg Phe Thr Arg Phe Ala Gly Glu Leu Phe
145                 150                 155                 160

Gly Met Leu Ile Thr Ile Leu Phe Met Gln Glu Ala Val Lys Gly Met
                165                 170                 175

Leu Gly Glu Phe Ser Val Pro Glu Gly Lys Asp His Ser Leu Pro Ile
            180                 185                 190

Tyr Gln Phe Gln Trp Ala Tyr Val Asn Gly Leu Leu Gly Ile Ile Phe
        195                 200                 205

Ser Met Gly Leu Leu Tyr Thr Ala Ile Arg Ser Arg Ser Ala Arg Ser
210                 215                 220

Ser Leu Tyr Gly Thr Gly Trp Gln Arg Ser Phe Ile Ala Asp Tyr Gly
225                 230                 235                 240

Val Pro Leu Met Val Val Trp Thr Ala Leu Ser Tyr Ser Leu Pro
                245                 250                 255

Ser Lys Ile Pro Ser Gly Val Pro Arg Arg Leu Phe Thr Pro Leu Pro
            260                 265                 270

Trp Glu Pro Lys Ser Leu Gln His Trp Thr Val Ala Lys Asp Leu Phe
        275                 280                 285

Ser Val Pro Pro Tyr Ile Phe Leu Ala Ile Val Pro Ala Val Met
290                 295                 300

Val Ala Gly Leu Tyr Phe Phe Asp His Ser Val Ala Ser Gln Leu Ala
305                 310                 315                 320

Gln Gln Lys Glu Phe Asn Leu Lys Asn Pro Ser Ala Tyr His Tyr Asp
            325                 330                 335
```

```
Ile Leu Val Leu Ser Phe Met Val Leu Ile Cys Gly Leu Ile Gly Ile
            340                 345                 350

Pro Pro Ser Asn Gly Val Leu Pro Gln Ser Pro Met His Thr Arg Ser
            355                 360                 365

Leu Ala Val Leu Lys Gly Gln Leu Leu Arg Lys Met Val Gln Thr
370                 375                 380

Ala Lys Glu Gly Met Met Asn Asn Ala Ser Ser Glu Val Tyr Gly
385                 390                 395                 400

Lys Met Gln Glu Val Phe Ile Lys Met Asp Asp Lys Ser Asn Ala Lys
                    405                 410                 415

Ser Val Arg Lys Glu Leu Lys Glu Leu Lys Asp Ala Val Ile Pro Glu
420                 425                 430

Gly Asn Gly Ala Gly Arg Val Ser Glu Val Phe Asp Pro Glu Lys His
            435                 440                 445

Ile Glu Ala Tyr Leu Pro Val Arg Val Asn Glu Gln Arg Val Ser Asn
            450                 455                 460

Leu Leu Gln Ser Leu Leu Ile Ala Gly Cys Val Gly Val Met Pro Ile
465                 470                 475                 480

Ile Gln Lys Ile Pro Thr Ser Val Leu Trp Gly Tyr Phe Ala Tyr Met
                    485                 490                 495

Ser Ile Asp Ser Val Pro Gly Asn Gln Phe Trp Glu Arg Thr Gln Leu
            500                 505                 510

Leu Phe Ile Ser Pro Gln Arg Arg Tyr Lys Leu Leu Glu Gly Ala His
            515                 520                 525

Ala Ser Phe Met Glu Ser Val Pro Ile Lys Lys Ile Ser Ala Phe Thr
            530                 535                 540

Ile Phe Gln Leu Val Tyr Leu Leu Ile Val Trp Gly Met Thr Trp Ile
545                 550                 555                 560

Pro Val Ala Gly Ile Leu Phe Pro Leu Phe Phe Leu Ile Val
            565                 570                 575

Ile Arg Gln Tyr Ile Leu Pro Lys Phe Phe Asp Pro Arg His Leu Trp
            580                 585                 590

Glu Leu Asp Ala Ala Glu Tyr Glu Glu Leu Glu Gly Val Arg Arg Asp
            595                 600                 605

Pro Ser Thr Asp Glu Asp Ala Ser Val Ser Arg Cys Ser Asp Ala Ser
            610                 615                 620

Pro Glu Tyr Ala Ser Glu Ile Leu Asp Glu Phe Thr Thr Asn Arg Gly
625                 630                 635                 640

Glu Leu Lys His Arg Thr Lys Ser Phe Arg Asp Glu Arg Leu Ile Gln
            645                 650                 655

Leu Asn Ser Val Lys Met Thr Arg Glu Leu Ser Arg Ile Pro Thr Phe
            660                 665                 670

Thr Pro Pro Arg Ser
        675

<210> SEQ ID NO 32
<211> LENGTH: 704
<212> TYPE: PRT
<213> ORGANISM: Arabidopsis thaliana

<400> SEQUENCE: 32

Met Glu Glu Thr Phe Val Pro Phe Glu Gly Ile Lys Asn Asp Leu Lys
1               5                   10                  15

Gly Arg Leu Met Cys Tyr Lys Gln Asp Trp Thr Gly Gly Phe Lys Ala
            20                  25                  30
```

```
Gly Phe Arg Ile Leu Ala Pro Thr Thr Tyr Ile Phe Ala Ser Ala
         35                  40                  45

Ile Pro Val Ile Ser Phe Gly Glu Gln Leu Glu Arg Ser Thr Asp Gly
 50                  55                  60

Val Leu Thr Ala Val Gln Thr Leu Ala Ser Thr Ala Ile Cys Gly Met
 65                  70                  75                  80

Ile His Ser Ile Ile Gly Gly Gln Pro Leu Leu Ile Leu Gly Val Ala
                 85                  90                  95

Glu Pro Thr Val Ile Met Tyr Thr Phe Met Phe Asn Phe Ala Lys Ala
            100                 105                 110

Arg Pro Glu Leu Gly Arg Asp Leu Phe Leu Ala Trp Ser Gly Trp Val
            115                 120                 125

Cys Val Trp Thr Ala Leu Met Leu Phe Val Leu Ala Ile Cys Gly Ala
            130                 135                 140

Cys Ser Ile Ile Asn Arg Phe Thr Arg Val Ala Gly Glu Leu Phe Gly
145                 150                 155                 160

Leu Leu Ile Ala Met Leu Phe Met Gln Gln Ala Ile Lys Gly Leu Val
                165                 170                 175

Asp Glu Phe Arg Ile Pro Glu Arg Glu Asn Gln Lys Leu Lys Glu Phe
            180                 185                 190

Leu Pro Ser Trp Arg Phe Ala Asn Gly Met Phe Ala Leu Val Leu Ser
            195                 200                 205

Phe Gly Leu Leu Leu Thr Gly Leu Arg Ser Arg Lys Ala Arg Ser Trp
210                 215                 220

Arg Tyr Gly Thr Gly Trp Leu Arg Ser Leu Ile Ala Asp Tyr Gly Val
225                 230                 235                 240

Pro Leu Met Val Leu Val Trp Thr Gly Val Ser Tyr Ile Pro Ala Gly
                245                 250                 255

Asp Val Pro Lys Gly Ile Pro Arg Arg Leu Phe Ser Pro Asn Pro Trp
            260                 265                 270

Ser Pro Gly Ala Tyr Gly Asn Trp Thr Val Val Lys Glu Met Leu Asp
            275                 280                 285

Val Pro Ile Val Tyr Ile Gly Ala Phe Ile Pro Ala Ser Met Ile
            290                 295                 300

Ala Val Leu Tyr Tyr Phe Asp His Ser Val Ala Ser Gln Leu Ala Gln
305                 310                 315                 320

Gln Lys Glu Phe Asn Leu Arg Lys Pro Ser Ser Tyr His Tyr Asp Leu
                325                 330                 335

Leu Leu Leu Gly Phe Leu Thr Leu Met Cys Gly Leu Leu Gly Val Pro
            340                 345                 350

Pro Ser Asn Gly Val Ile Pro Gln Ser Pro Met His Thr Lys Ser Leu
            355                 360                 365

Ala Thr Leu Lys Tyr Gln Leu Leu Arg Asn Arg Leu Val Ala Thr Ala
370                 375                 380

Arg Arg Ser Ile Lys Thr Asn Ala Ser Leu Gly Gln Leu Tyr Asp Asn
385                 390                 395                 400

Met Gln Glu Ala Tyr His His Met Gln Thr Pro Leu Val Tyr Gln Gln
                405                 410                 415

Pro Gln Gly Leu Lys Glu Leu Lys Glu Ser Thr Ile Gln Ala Thr Thr
            420                 425                 430

Phe Thr Gly Asn Leu Asn Ala Pro Val Asp Glu Thr Leu Phe Asp Ile
            435                 440                 445

Glu Lys Glu Ile Asp Asp Leu Leu Pro Val Glu Val Lys Glu Gln Arg
450                 455                 460
```

```
Val Ser Asn Leu Leu Gln Ser Thr Met Val Gly Gly Cys Val Ala Ala
465                 470                 475                 480

Met Pro Ile Leu Lys Met Ile Pro Thr Ser Val Leu Trp Gly Tyr Phe
            485                 490                 495

Ala Phe Met Ala Ile Glu Ser Leu Pro Gly Asn Gln Phe Trp Glu Arg
        500                 505                 510

Ile Leu Leu Leu Phe Thr Ala Pro Ser Arg Arg Phe Lys Val Leu Glu
            515                 520                 525

Asp Tyr His Ala Thr Phe Val Glu Thr Val Pro Phe Lys Thr Ile Ala
530                 535                 540

Met Phe Thr Leu Phe Gln Thr Thr Tyr Leu Leu Ile Cys Phe Gly Leu
545                 550                 555                 560

Thr Trp Ile Pro Ile Ala Gly Val Met Phe Pro Leu Met Ile Met Phe
                565                 570                 575

Leu Ile Pro Val Arg Gln Tyr Leu Leu Pro Arg Phe Phe Lys Gly Ala
            580                 585                 590

His Leu Gln Asp Leu Asp Ala Ala Glu Tyr Glu Glu Ala Pro Ala Leu
            595                 600                 605

Pro Phe Asn Leu Ala Ala Glu Thr Glu Ile Gly Ser Thr Thr Ser Tyr
        610                 615                 620

Pro Gly Asp Leu Glu Ile Leu Asp Glu Val Met Thr Arg Ser Arg Gly
625                 630                 635                 640

Glu Phe Arg His Thr Ser Ser Pro Lys Val Thr Ser Ser Ser Ser Thr
                645                 650                 655

Pro Val Asn Asn Arg Ser Leu Ser Gln Val Phe Ser Pro Arg Val Ser
            660                 665                 670

Gly Ile Arg Leu Gly Gln Met Ser Pro Arg Val Val Gly Asn Ser Pro
            675                 680                 685

Lys Pro Ala Ser Cys Gly Arg Ser Pro Leu Asn Gln Ser Ser Ser Asn
690                 695                 700

<210> SEQ ID NO 33
<211> LENGTH: 703
<212> TYPE: PRT
<213> ORGANISM: Arabidopsis thaliana

<400> SEQUENCE: 33

Met Glu Glu Thr Phe Val Pro Phe Glu Gly Ile Lys Asn Asp Leu Lys
1               5                   10                  15

Gly Arg Leu Met Cys Tyr Lys Gln Asp Trp Thr Gly Gly Ile Lys Ala
            20                  25                  30

Gly Phe Arg Ile Leu Ala Pro Thr Thr Tyr Ile Phe Phe Ala Ser Ala
        35                  40                  45

Ile Pro Val Ile Ser Phe Gly Glu Gln Leu Glu Arg Ser Thr Asp Gly
    50                  55                  60

Val Leu Thr Ala Val Gln Thr Leu Ala Ser Thr Ala Ile Cys Gly Ile
65                  70                  75                  80

Ile His Ser Ile Ile Gly Gly Gln Pro Leu Leu Ile Leu Gly Val Ala
                85                  90                  95

Glu Pro Thr Val Ile Met Tyr Thr Phe Met Phe Asn Phe Ala Lys Gly
            100                 105                 110

Arg Pro Glu Leu Gly Arg Asn Leu Phe Leu Ala Trp Ser Gly Trp Val
        115                 120                 125

Cys Val Trp Thr Ser Leu Ile Leu Phe Val Leu Ala Ile Cys Gly Ala
    130                 135                 140
```

```
Cys Ser Phe Ile Asn Arg Phe Thr Arg Val Ala Gly Glu Leu Phe Gly
145                 150                 155                 160
Leu Leu Ile Ala Met Leu Phe Met Gln Gln Ala Ile Lys Gly Leu Val
                165                 170                 175
Asp Glu Phe Arg Ala Pro Ala Arg Glu Asp Leu Lys Leu Val Glu Phe
            180                 185                 190
Leu Pro Ser Trp Arg Phe Ala Asn Gly Met Phe Ala Leu Val Leu Ser
        195                 200                 205
Phe Gly Leu Leu Ile Thr Ala Leu Arg Ser Arg Lys Ala Arg Ser Trp
    210                 215                 220
Arg Tyr Gly Thr Gly Trp Leu Arg Ser Leu Val Ala Asp Tyr Gly Val
225                 230                 235                 240
Pro Leu Met Val Leu Val Trp Thr Gly Val Ser Tyr Ile Pro Thr Gly
                245                 250                 255
Asp Val Pro Lys Gly Ile Pro Arg Arg Leu Phe Ser Pro Asn Pro Trp
            260                 265                 270
Ser Pro Gly Ala Tyr Glu Asn Trp Thr Val Val Lys Glu Met Leu Gln
        275                 280                 285
Val Pro Ile Val Tyr Ile Ile Gly Ala Phe Ile Pro Ala Thr Met Ile
    290                 295                 300
Ala Val Leu Tyr Tyr Phe Asp His Ser Val Ala Ser Gln Leu Ala Gln
305                 310                 315                 320
Gln Lys Glu Phe Asn Leu Arg Lys Pro Ser Ser Tyr His Tyr Asp Leu
                325                 330                 335
Leu Leu Leu Gly Phe Leu Thr Leu Met Cys Gly Leu Leu Gly Ile Pro
            340                 345                 350
Pro Ser Asn Gly Val Ile Pro Gln Ser Pro Met His Thr Lys Ser Leu
        355                 360                 365
Ala Thr Leu Lys Tyr Gln Leu Leu Arg Asn Arg Leu Val Ala Thr Ala
    370                 375                 380
Arg Lys Ser Ile Lys Gln Asn Ala Ser Leu Gly Gln Leu Tyr Gly Asn
385                 390                 395                 400
Met Gln Asp Val Tyr Asn Gln Met Gln Thr Pro Leu Val Tyr Gln Gln
                405                 410                 415
Pro Gln Gly Leu Lys Glu Leu Arg Glu Ser Thr Ile Gln Ala Thr Thr
            420                 425                 430
Phe Thr Gly Asn Leu Asp Ala Pro Val Asp Glu Thr Leu Phe Asp Ile
        435                 440                 445
Glu Lys Glu Ile Asp Asp Leu Leu Pro Ile Glu Val Lys Glu Gln Arg
    450                 455                 460
Val Ser Asn Leu Leu Gln Ala Val Met Val Gly Gly Cys Val Ala Ala
465                 470                 475                 480
Met Pro Leu Leu Lys Met Ile Pro Thr Ser Val Leu Trp Gly Tyr Phe
                485                 490                 495
Ala Phe Met Ala Ile Glu Ser Leu Pro Gly Asn Gln Phe Trp Glu Arg
            500                 505                 510
Ile Leu Leu Leu Phe Thr Ala Pro Ser Arg Arg Phe Lys Val Leu Glu
        515                 520                 525
Asp Asn His Ala Thr Phe Val Glu Thr Val Pro Phe Lys Thr Ile Ala
    530                 535                 540
Met Phe Thr Ile Phe Gln Thr Thr Tyr Leu Leu Thr Cys Phe Gly Leu
545                 550                 555                 560
Thr Trp Ile Pro Ile Ala Gly Val Met Phe Pro Leu Leu Ile Met Phe
```

```
                  565                 570                 575
Leu Ile Pro Val Arg Gln Tyr Ile Leu Pro Arg Phe Phe Lys Ser Ala
                580                 585                 590

His Leu Gln Asp Leu Asp Ala Ala Glu Tyr Glu Glu Ala Pro Ala Leu
                595                 600                 605

Pro Phe His Leu Ala Val Pro Glu Ala Glu Met Gly Ser Thr Ala Ser
                610                 615                 620

Tyr Pro Cys Asp Ser Glu Ile Leu Asp Glu Phe Ile Thr Arg Ser Arg
625                 630                 635                 640

Gly Glu Phe Arg His Thr Cys Ser Pro Lys Val Thr Ser Ser Thr Ser
                645                 650                 655

Thr Pro Val Tyr Asn Arg Asn Leu Ser Gln Val Phe Ser Pro Arg Val
                660                 665                 670

Ile Asp Leu Arg Gly Glu Met Ser Pro Arg Leu Ser Gly Lys Gly Gln
                675                 680                 685

Asn Ser Pro Lys Pro Ser Pro Leu Asn Pro Ser Ser Ser Lys
                690                 695                 700

<210> SEQ ID NO 34
<211> LENGTH: 732
<212> TYPE: PRT
<213> ORGANISM: Arabidopsis thaliana

<400> SEQUENCE: 34

Met Asp Glu Ala Glu Ser Phe Val Pro Phe Gln Gly Ile Lys Lys Asp
1               5                   10                  15

Val Lys Gly Arg Leu Asn Cys Tyr Lys Gln Asp Trp Ile Ser Gly Leu
                20                  25                  30

Arg Ala Gly Phe Arg Ile Leu Ala Pro Thr Thr Tyr Ile Phe Phe Ala
            35                  40                  45

Ser Ala Ile Pro Val Ile Thr Phe Gly Glu Gln Leu Glu Arg Asp Thr
        50                  55                  60

Asp Gly Lys Ile Thr Ala Val Gln Thr Leu Val Ser Thr Ala Leu Cys
65                  70                  75                  80

Gly Val Ile His Ser Ile Ile Gly Gly Gln Pro Leu Leu Ile Leu Gly
                85                  90                  95

Val Ala Glu Pro Thr Val Ile Met Tyr Thr Phe Met Phe Asn Phe Ala
                100                 105                 110

Lys Ser Arg Thr Asp Leu Gly Ser Asn Leu Phe Leu Ala Trp Thr Gly
            115                 120                 125

Trp Val Cys Leu Trp Thr Gly Leu Leu Leu Phe Leu Leu Ala Val Leu
        130                 135                 140

Gly Ala Cys Thr Phe Ile Asn Arg Phe Thr Arg Leu Ala Gly Glu Leu
145                 150                 155                 160

Phe Gly Ile Leu Ile Ala Met Leu Phe Met Gln Glu Ala Ile Arg Gly
                165                 170                 175

Ile Val Asp Glu Phe Gly Val Pro Gly Arg Thr Asn Pro Arg Ser Ala
            180                 185                 190

Glu Phe Gln Pro Ala Trp Val Phe Ala Asn Gly Met Phe Gly Leu Val
        195                 200                 205

Leu Ser Ser Gly Leu Leu Tyr Thr Gly Leu Lys Ser Arg Lys Ala Arg
        210                 215                 220

Ser Trp Arg Phe Gly Ala Glu Trp Leu Arg Gly Phe Ile Ala Asp Tyr
225                 230                 235                 240

Gly Val Pro Val Met Val Val Val Trp Thr Cys Ile Ser Tyr Ile Pro
```

-continued

```
            245                 250                 255
Trp Lys Ser Val Pro Gln Gly Ile Pro Arg Arg Leu Val Ser Pro Asn
                260                 265                 270

Pro Trp Ser Pro Gly Ala Tyr Gln Asn Trp Thr Val Ile Lys Glu Met
            275                 280                 285

Val Asp Val Pro Val Leu Tyr Ile Leu Leu Ala Val Pro Ala Ser
        290                 295                 300

Met Ile Ala Val Leu Tyr Tyr Phe Asp His Ser Val Ala Ser Gln Leu
305                 310                 315                 320

Ala Gln Gln Glu Asp Phe Asn Leu Arg Lys Pro Pro Ala Tyr His Tyr
                325                 330                 335

Asp Leu Phe Leu Leu Gly Phe Leu Thr Ile Leu Cys Gly Leu Ile Gly
            340                 345                 350

Ile Pro Pro Ser Asn Gly Val Ile Pro Gln Ser Pro Met His Thr Lys
            355                 360                 365

Ser Leu Ala Thr Leu Asn His Gln Leu Leu Arg Asn Lys Leu Val Ala
370                 375                 380

Ala Ala Arg Lys Cys Ile Arg Asn Asn Ala Thr Ile Gly Glu Val Tyr
385                 390                 395                 400

Gly Ser Met Glu Glu Ala Tyr Gln Gln Met Gln Ser Pro Leu Ile His
            405                 410                 415

Gln Glu Pro Ser Arg Ile Gln Gly Leu Lys Gln Ser His Ile Gln Lys
                420                 425                 430

Ala Ser Asn Ala Asp Ala Leu Val Asp Glu Thr Val Phe Asp Ile Glu
            435                 440                 445

Thr Glu Val Glu Asn Ile Leu Pro Val Glu Val Lys Glu Gln Arg Val
        450                 455                 460

Ser Asn Phe Leu Gln Ala Met Met Val Ala Gly Cys Val Ala Ala Met
465                 470                 475                 480

Pro Leu Ile Lys Arg Ile Pro Ser Ser Val Leu Trp Gly Tyr Phe Ala
                485                 490                 495

Tyr Met Ala Ile Glu Ser Leu Pro Gly Asn Gln Phe Trp Glu Arg Ile
            500                 505                 510

Val Leu Leu Phe Thr Ala Pro Ser Arg Arg Phe Lys Val Leu Glu Asp
        515                 520                 525

Asn His Ala Val Phe Ile Glu Thr Val Pro Phe Lys Thr Met Ala Met
        530                 535                 540

Phe Thr Leu Phe Gln Thr Ala Tyr Leu Leu Val Cys Phe Gly Ile Thr
545                 550                 555                 560

Trp Val Pro Val Ala Gly Val Leu Phe Pro Leu Met Ile Met Phe Leu
            565                 570                 575

Val Pro Val Arg Gln Tyr Val Leu Pro Asn Phe Phe Lys Gly Ala His
            580                 585                 590

Leu Gln Asp Leu Asp Ala Ala Glu Tyr Glu Glu Ala Pro Ala Ile Leu
                595                 600                 605

Ser Phe Asn Leu Lys Pro Glu Gly Glu Val Ser Arg Ala Thr Ser Phe
            610                 615                 620

Ala Asp Ser Gly Glu Val Met Asp Gly Met Phe Thr Arg Ser Arg Gly
625                 630                 635                 640

Glu Ile Arg Lys Val Ser Ser Leu Lys Leu Gly Gly Gly Gly Ser Gly
                645                 650                 655

Ser Thr Val Gly Ser Pro Ala Gly Gly Val Glu Leu Met Arg Arg
            660                 665                 670
```

```
Val Val Ser Phe Gln Asn Pro Arg Val Ser Glu Lys Val Tyr Ile Arg
            675                 680                 685

Ser Leu Ser Asp Phe Arg Gly Gly Glu Ile Ser Pro Arg Ser Ser
    690                 695                 700

Ala Gly Arg Ala Pro Phe Ser Pro Arg Ser Ala Thr Gly Gly Gly
705                 710                 715                 720

Gly Glu Gln Arg Leu Ser Asn Leu Gly Lys Ser Val
            725                 730

<210> SEQ ID NO 35
<211> LENGTH: 683
<212> TYPE: PRT
<213> ORGANISM: Arabidopsis thaliana

<400> SEQUENCE: 35

Met Glu Glu Glu Arg Val Asp Ser Ser Lys Arg Leu Phe Arg Gly Ile
1               5                   10                  15

Val Ala Asp Leu Arg Gly Arg Ala Leu Cys Tyr Lys Glu Asp Trp Val
                20                  25                  30

Ala Gly Leu Arg Ser Gly Phe Gly Ile Leu Ala Pro Thr Thr Tyr Ile
            35                  40                  45

Phe Phe Ala Ser Ala Leu Pro Val Ile Ala Phe Gly Glu Gln Leu Ser
    50                  55                  60

Arg Asp Thr Glu Gly Ala Leu Ser Thr Val Thr Leu Ala Ser Thr
65                  70                  75                  80

Ala Leu Cys Gly Val Ile His Ser Ile Leu Gly Gly Gln Pro Leu Leu
                85                  90                  95

Ile Leu Gly Val Ala Glu Pro Thr Val Leu Met Tyr Val Tyr Leu Tyr
            100                 105                 110

Asn Phe Ala Ile Gly Arg Pro Glu Leu Gly Lys Gln Leu Tyr Leu Ala
    115                 120                 125

Trp Ala Ala Trp Val Cys Val Trp Thr Ala Leu Leu Phe Val Met
130                 135                 140

Ala Ile Leu Asn Thr Ala Asp Ile Ile Asn Arg Phe Thr Arg Val Ala
145                 150                 155                 160

Gly Glu Leu Phe Gly Met Leu Ile Ser Val Leu Phe Ile Gln Gln Ala
                165                 170                 175

Ile Lys Gly Met Val Ser Glu Phe Gly Met Pro Lys Asp Glu Asp Ser
            180                 185                 190

Lys Leu Glu Lys Tyr Lys Phe Glu Trp Leu Tyr Thr Asn Gly Leu Leu
    195                 200                 205

Gly Leu Ile Phe Thr Phe Gly Leu Leu Tyr Thr Ala Leu Lys Ser Arg
210                 215                 220

Lys Ala Arg Ser Trp Arg Tyr Gly Thr Gly Trp Tyr Arg Ser Phe Ile
225                 230                 235                 240

Ala Asp Tyr Gly Val Pro Leu Met Val Val Trp Thr Ala Leu Ser
                245                 250                 255

Phe Ser Thr Pro Ser Lys Leu Pro Ser Gly Val Pro Arg Arg Leu Phe
            260                 265                 270

Ser Pro Leu Pro Trp Asp Ser Pro Ser Leu Ser His Trp Thr Val Ile
    275                 280                 285

Lys Asp Met Gly Lys Val Ser Pro Gly Tyr Ile Phe Ala Ala Phe Ile
290                 295                 300

Pro Ala Leu Met Ile Ala Gly Leu Tyr Phe Phe Asp His Ser Val Ala
305                 310                 315                 320
```

```
Ser Gln Leu Ala Gln Lys Glu Phe Asn Leu Lys Lys Pro Ser Ala
            325                 330                 335

Tyr His Tyr Asp Ile Leu Leu Gly Phe Met Thr Leu Ile Cys Gly
            340                 345                 350

Leu Leu Gly Leu Pro Pro Ser Asn Gly Val Leu Pro Gln Ser Pro Met
            355                 360                 365

His Thr Lys Ser Leu Ala Val Leu Lys Arg Gln Leu Ile Arg Arg Lys
    370                 375                 380

Met Val Lys Thr Ala Lys Glu Ser Ile Arg Lys Arg Glu Thr Ser Ser
385                 390                 395                 400

Gln Val Tyr Glu Asn Met Gln Glu Val Phe Ile Glu Met Asp Lys Ser
            405                 410                 415

Pro Leu Ala Gln Thr Asp Pro Ser Val Ile Ile Glu Leu Gln Asp Leu
            420                 425                 430

Lys Glu Ala Val Met Lys Ser Asn Asp Glu Arg Glu Gly Asp Glu
            435                 440                 445

Glu Ser Gly Phe Asp Pro Glu Lys His Leu Asp Ala Tyr Leu Pro Val
            450                 455                 460

Arg Val Asn Glu Gln Arg Val Ser Asn Leu Leu Gln Ser Leu Val
465                 470                 475                 480

Ala Gly Ala Val Leu Ala Met Pro Ala Ile Lys Leu Ile Pro Thr Ser
            485                 490                 495

Ile Leu Trp Gly Tyr Phe Ala Tyr Met Ala Ile Asp Ser Leu Pro Gly
            500                 505                 510

Asn Gln Phe Phe Glu Arg Leu Thr Leu Leu Phe Val Pro Thr Ser Arg
            515                 520                 525

Arg Phe Lys Val Leu Glu Gly Ala His Ala Ser Phe Val Glu Lys Val
            530                 535                 540

Pro Tyr Lys Ser Met Ala Ala Phe Thr Leu Leu Gln Ile Phe Tyr Phe
545                 550                 555                 560

Gly Leu Cys Tyr Gly Val Thr Trp Ile Pro Val Ala Gly Ile Met Phe
            565                 570                 575

Pro Val Pro Phe Phe Leu Leu Ile Ala Ile Arg Gln Tyr Ile Leu Pro
            580                 585                 590

Lys Leu Phe Asn Pro Ala His Leu Arg Glu Leu Asp Ala Ala Glu Tyr
            595                 600                 605

Glu Glu Ile Pro Gly Thr Pro Arg Asn Pro Leu Glu Leu Ser Phe Arg
            610                 615                 620

Ser Asn Asp Ser Lys Arg Gly Val Gln Glu Gly Asp Ala Glu Ile Leu
625                 630                 635                 640

Asp Glu Leu Thr Thr Ser Arg Gly Glu Leu Lys Val Arg Thr Leu Asn
            645                 650                 655

Leu Asn Glu Asp Lys Gly Asn Gln Ile Tyr Pro Lys Glu Lys Val Lys
            660                 665                 670

Ala Gly Asp Gly Asp Met Ser Thr Thr Arg Glu
            675                 680

<210> SEQ ID NO 36
<211> LENGTH: 683
<212> TYPE: PRT
<213> ORGANISM: Arabidopsis thaliana

<400> SEQUENCE: 36

Met Glu Glu Glu Arg Val Glu Gly Ser Lys Arg Pro Phe Gln Gly Ile
1               5                   10                  15
```

```
Ile Arg Asp Val Lys Gly Arg Ala Leu Cys Tyr Lys Gln Asp Trp Ile
            20                  25                  30

Ala Gly Leu Arg Ser Gly Phe Gly Ile Leu Ala Pro Thr Thr Tyr Val
        35                  40                  45

Phe Phe Ala Ser Ala Leu Pro Val Ile Ala Phe Gly Glu Gln Leu Ser
50                  55                  60

His Asp Thr Glu Arg Ser Leu Ser Thr Val Glu Thr Leu Ala Ser Thr
65                  70                  75                  80

Ala Leu Cys Gly Val Ile His Ser Leu Leu Gly Gly Gln Pro Leu Leu
                85                  90                  95

Ile Leu Gly Val Ala Glu Pro Thr Val Leu Met Tyr Lys Tyr Leu Tyr
            100                 105                 110

Asp Phe Ala Lys Gly Arg Pro Glu Leu Gly Lys Gln Leu Tyr Leu Ala
            115                 120                 125

Trp Val Ala Trp Val Cys Val Trp Thr Ala Leu Leu Phe Leu Met
            130                 135                 140

Ala Ile Phe Asn Met Ala Tyr Ile Ile Asn Arg Phe Thr Arg Ile Ala
145                 150                 155                 160

Gly Glu Leu Phe Gly Met Leu Ile Ala Val Leu Phe Leu Gln Gln Thr
                165                 170                 175

Ile Lys Gly Met Val Ser Glu Phe Arg Ile Pro Lys Gly Glu Asp Ser
            180                 185                 190

Lys Leu Glu Lys Tyr Gln Phe Glu Trp Leu Tyr Thr Asn Gly Leu Leu
            195                 200                 205

Gly Leu Ile Phe Thr Val Gly Leu Val Tyr Thr Ala Leu Lys Ser Arg
            210                 215                 220

Lys Ala Arg Ser Trp Pro Tyr Gly Thr Gly Cys Cys Arg Ser Phe Val
225                 230                 235                 240

Ala Asp Tyr Gly Val Pro Leu Met Val Val Trp Thr Ala Leu Ser
            245                 250                 255

Phe Ser Thr Pro Ser Lys Leu Pro Ser Gly Val Pro Arg Arg Leu Val
                260                 265                 270

Ser Pro Leu Pro Trp Asp Ser Val Ser Leu Thr His Trp Thr Val Ile
            275                 280                 285

Lys Asp Met Gly Lys Val Ser Pro Gly Tyr Ile Phe Ala Ala Phe Ile
290                 295                 300

Pro Ala Leu Met Ile Ala Gly Leu Tyr Phe Phe Asp His Ser Val Val
305                 310                 315                 320

Ser Gln Leu Ala Gln Gln Lys Glu Phe Asn Leu Lys Asn Pro Ser Ala
                325                 330                 335

Tyr His Tyr Asp Ile Leu Leu Leu Gly Phe Met Val Leu Ile Cys Gly
            340                 345                 350

Met Leu Gly Leu Pro Pro Ser Asn Gly Val Leu Pro Gln Ser Pro Met
            355                 360                 365

His Thr Lys Ser Leu Ala Val Phe Lys Arg Gln Leu Met Arg Arg Lys
            370                 375                 380

Met Val Met Thr Ala Lys Glu Ser Ile Arg Gln Lys Ala Thr Ser Ser
385                 390                 395                 400

Gln Val Tyr Glu Asp Met Glu Gln Val Phe Ile Glu Met Asp Lys Ser
                405                 410                 415

Pro Leu Ala Glu Thr His Thr Thr Leu Ile Asn Glu Leu Gln Asp Leu
            420                 425                 430

Lys Glu Ala Val Met Lys Lys Ser Asp Asp Gly Asp Thr Gly Glu
            435                 440                 445
```

```
Glu Ser Gly Phe Asp Pro Glu Lys His Val Asp Ala Tyr Leu Pro Val
        450                 455                 460

Arg Val Asn Glu Gln Arg Val Ser Asn Leu Leu Gln Ser Leu Leu Val
465                 470                 475                 480

Ile Gly Ala Val Phe Ala Leu Pro Val Ile Lys Leu Ile Pro Thr Ser
                485                 490                 495

Leu Leu Trp Gly Tyr Phe Ala Tyr Met Ala Ile Asp Ser Leu Pro Asp
                500                 505                 510

Asn Gln Phe Phe Glu Arg Thr Val Leu Leu Phe Val Pro Pro Thr Arg
                515                 520                 525

Arg Phe Lys Val Leu Glu Gly Ala His Ala Ser Phe Val Glu Lys Val
        530                 535                 540

Pro His Lys Ser Ile Ala Ala Phe Thr Leu Phe Gln Ile Leu Tyr Phe
545                 550                 555                 560

Gly Leu Cys Tyr Gly Val Thr Trp Ile Pro Val Ala Gly Ile Met Phe
                565                 570                 575

Pro Val Leu Phe Phe Leu Leu Val Ala Ile Arg Gln Tyr Leu Leu Pro
                580                 585                 590

Lys Leu Phe Lys Pro Ala Tyr Leu Arg Glu Leu Asp Ala Ala Glu Tyr
        595                 600                 605

Glu Glu Ile Pro Gly Thr Pro Arg Asn Pro Leu Glu Leu Ser Phe Arg
610                 615                 620

Ser Asn Asn Ser Ala Arg Gly Val Gln Glu Cys Asp Ala Glu Ile Leu
625                 630                 635                 640

Asp Glu Leu Thr Thr Ser Arg Gly Leu Lys Val Arg Thr Leu Gly
                645                 650                 655

His Asn Glu Asp Lys Gly His Gln Ile Tyr Pro Lys Gly Ile Val Glu
                660                 665                 670

Val Gly Asp Gly Asp Met Ser Ser Ser Arg Glu
        675                 680

<210> SEQ ID NO 37
<211> LENGTH: 671
<212> TYPE: PRT
<213> ORGANISM: Arabidopsis thaliana

<400> SEQUENCE: 37

Met Lys Ser Glu Gly Glu Ser Gly Pro Phe Gln Gly Ile Leu Arg Asp
1               5                   10                  15

Ile Glu Gly Arg Arg Lys Cys Tyr Lys Gln Asp Trp Ile Arg Gly Ile
                20                  25                  30

Lys Thr Gly Ile Arg Ile Leu Ala Pro Thr Cys Tyr Ile Phe Phe Ala
        35                  40                  45

Ser Ser Leu Pro Val Val Ala Phe Gly Glu Gln Leu Ser Lys His Thr
50                  55                  60

Gly Gly Ala Leu Ser Ala Val Glu Thr Leu Ala Ser Thr Ser Ile Cys
65                  70                  75                  80

Gly Ile Ile His Ala Ile Phe Gly Gly Gln Pro Leu Leu Ile Val Gly
                85                  90                  95

Val Ala Glu Pro Thr Ile Ile Met Tyr Thr Tyr Leu Tyr Ser Phe Cys
                100                 105                 110

Ile Ser Arg Pro Asp Ile Gly Arg Glu Leu Tyr Leu Ala Trp Val Ala
        115                 120                 125

Trp Val Cys Val Trp Thr Ser Val Leu Leu Ile Leu Leu Ser Ile Phe
130                 135                 140
```

-continued

```
Asn Ala Gly Thr Ile Ile Thr Arg Phe Thr Arg Ile Ala Gly Glu Leu
145                 150                 155                 160

Phe Gly Met Leu Ile Ala Val Leu Phe Leu Gln Glu Ala Ile Lys Gly
                165                 170                 175

Leu Ile Ser Glu Phe His Ala Pro Glu Ile Lys Asn Gln Glu Thr Gly
            180                 185                 190

Lys Ser His Phe Leu Leu Ile Tyr Ala Asn Gly Leu Leu Ala Val Ile
        195                 200                 205

Phe Ser Leu Gly Leu Leu Ile Thr Ala Leu Lys Ser Arg Arg Ala Lys
    210                 215                 220

Ser Trp Lys Tyr Gly Phe Gly Trp Leu Arg Ser Phe Ile Gly Asp Tyr
225                 230                 235                 240

Gly Val Pro Leu Met Val Leu Leu Trp Thr Ala Leu Ser Tyr Thr Val
                245                 250                 255

Pro Ser Glu Val Leu Pro Ser Val Pro Arg Arg Leu Phe Cys Pro Leu
            260                 265                 270

Pro Trp Glu Pro Ala Ser Leu Tyr His Trp Thr Val Lys Asp Met
        275                 280                 285

Gly Lys Val Pro Ile Met Tyr Ile Leu Ala Ala Phe Ile Pro Gly Val
    290                 295                 300

Met Ile Ala Gly Leu Tyr Phe Phe Asp His Ser Val Ala Ser Gln Met
305                 310                 315                 320

Ala Gln Gln Lys Glu Phe Asn Leu Lys Asn Pro Ser Ala Tyr His Tyr
                325                 330                 335

Asp Ile Phe Leu Leu Gly Ile Ile Thr Leu Ile Cys Gly Leu Leu Gly
            340                 345                 350

Leu Pro Pro Ser Asn Gly Val Leu Pro Gln Ala Pro Met His Thr Lys
        355                 360                 365

Ser Leu Ala Val Leu Asn Arg Gln Leu Ile Arg Lys Lys Met Val Lys
    370                 375                 380

Lys Ala Lys Glu Cys Met Lys Met Lys Ala Ser Lys Ser Glu Ile Tyr
385                 390                 395                 400

Gly Arg Met Gln Ser Val Phe Ile Glu Met Glu Thr Ser Pro Pro Gln
                405                 410                 415

Asp Asn Ser Val Ala Thr Asp Leu Lys Glu Leu Lys Glu Val Val Met
            420                 425                 430

Arg Pro Asp Glu Gly Asp Thr Lys Gly Lys Phe Asp Pro Asp Val
        435                 440                 445

His Ile Glu Ala Asn Leu Pro Val Arg Val Asn Gln Arg Val Ser
    450                 455                 460

Asn Leu Leu Gln Ser Val Leu Val Gly Leu Thr Leu Leu Ala Val Thr
465                 470                 475                 480

Val Ile Lys Met Ile Pro Ser Ser Val Leu Trp Gly Tyr Phe Ala Tyr
                485                 490                 495

Met Ala Ile Asp Ser Leu Pro Gly Asn Gln Phe Trp Glu Arg Leu Leu
            500                 505                 510

Leu Leu Phe Ile Pro Pro Ser Arg Leu Phe Lys Val Leu Glu Gly Val
        515                 520                 525

His Ala Ser Phe Val Glu Leu Val Pro Tyr Arg Val Ile Val Thr Phe
    530                 535                 540

Thr Leu Phe Gln Leu Val Tyr Phe Leu Leu Cys Tyr Gly Met Thr Trp
545                 550                 555                 560

Ile Pro Met Ala Gly Ile Phe Phe Pro Ala Leu Phe Phe Leu Leu Ile
```

```
                       565                 570                 575
Ser Ile Arg Glu His Leu Leu Pro Lys Leu Phe Asp Met Gln His Leu
                580                 585                 590

Gln Val Leu Asp Ala Ser Asp Tyr Glu Glu Ile Val Ala Ala Pro Ile
            595                 600                 605

Gln His Ser Ser Phe Ala Tyr Arg Lys Leu Gly Ser Ser His His Leu
        610                 615                 620

Ser Glu Gly Glu Asp Glu Phe Tyr Asp Ala Glu Ile Leu Asp Glu Met
625                 630                 635                 640

Thr Thr Ser Arg Gly Glu Ile Arg Ile Arg Thr Ile Ser Phe Lys Glu
                645                 650                 655

Val His Pro Glu Pro Glu Glu Lys His Val Thr Phe Glu Pro His
            660                 665                 670

<210> SEQ ID NO 38
<211> LENGTH: 673
<212> TYPE: PRT
<213> ORGANISM: Arabidopsis thaliana

<400> SEQUENCE: 38

Met Glu Gly Val Lys Phe Pro Phe Gly Gly Ile Ile Asn Asp Phe Asn
1               5                   10                  15

Gly Arg Arg Lys Cys Tyr Lys Gln Asp Trp Leu Ala Ala Phe Asn Ser
            20                  25                  30

Gly Val Arg Ile Leu Ala Pro Thr Leu Tyr Ile Phe Ile Ala Ser Ala
        35                  40                  45

Leu Pro Val Ile Ala Phe Gly Glu Gln Leu Ser Arg Glu Thr Asp Arg
    50                  55                  60

Ser Leu Gly Ile Ala Glu Ser Leu Ala Ser Thr Ala Leu Cys Gly Ile
65                  70                  75                  80

Ile His Ser Val Phe Gly Gly Gln Pro Leu Leu Ile Val Gly Val Ala
                85                  90                  95

Glu Pro Thr Ile Ile Met Tyr Thr Tyr Leu His Ser Phe Ser Lys Ser
            100                 105                 110

Arg Pro Glu Leu Gly Gln Lys Leu Tyr Leu Ala Trp Ala Gly Trp Val
        115                 120                 125

Cys Val Trp Thr Ala Val Leu Leu Met Leu Leu Ala Met Leu Asn Ala
    130                 135                 140

Cys Asn Ile Ile Ser Arg Phe Thr Arg Ile Ala Gly Glu Leu Phe Gly
145                 150                 155                 160

Met Leu Ile Thr Val Leu Phe Ile Gln Glu Ala Val Lys Gly Leu Ile
                165                 170                 175

Gly Glu Phe Leu Val Pro Lys Ser Asp Asp Pro Ser Leu Glu Val Tyr
            180                 185                 190

Gln Phe Gln Trp Arg Tyr Thr Asn Gly Leu Leu Ala Val Ile Phe Ser
        195                 200                 205

Phe Gly Leu Leu Tyr Thr Ala Leu Lys Ser Arg Arg Ala Arg Ser Trp
    210                 215                 220

Lys Tyr Gly Phe Arg Trp Met Arg Gly Phe Ile Gly Asp Tyr Gly Thr
225                 230                 235                 240

Leu Leu Met Leu Val Leu Trp Ser Ala Phe Ser Tyr Thr Val Pro Arg
                245                 250                 255

Asn Leu Pro Glu Gly Val Pro Arg Arg Leu Glu Leu Pro Leu Pro Trp
            260                 265                 270

Ala Ser Glu Ser Leu Tyr His Trp Thr Val Val Lys Asp Met Ala Lys
```

-continued

```
                275                 280                 285
Val Pro Pro Leu Tyr Ile Leu Ala Ala Phe Ile Pro Ala Ile Met Ile
290                 295                 300

Ala Gly Leu Tyr Phe Phe Asp His Cys Val Ser Ala Gln Met Ala Gln
305                 310                 315                 320

Gln Lys Glu Phe Asn Leu Lys Asn Pro Thr Ala Tyr His Tyr Asp Ile
                325                 330                 335

Phe Ile Leu Gly Ile Met Thr Leu Ile Cys Gly Leu Leu Gly Leu Pro
                340                 345                 350

Pro Ser Asn Gly Val Ile Pro Gln Ser Pro Met His Thr Lys Ser Leu
                355                 360                 365

Ala Val Leu Lys Lys Gln Gln Met Arg Lys Met Val Gln Lys Ala
370                 375                 380

Lys Glu Cys Met Arg Glu Lys Ala Ser Asn Ser Glu Ile Tyr Gly Arg
385                 390                 395                 400

Met Gln Asp Val Phe Ile Glu Met Glu Thr Ser Pro Lys Ala Thr Ser
                405                 410                 415

Val Val Lys Glu Leu Glu Asn Leu Lys Glu Ala Val Met Lys Ala Asp
                420                 425                 430

Asp Gly Gly Glu Thr Lys Gly Lys Lys Phe Asp Pro Glu Val His
                435                 440                 445

Ile Glu Asp His Leu Pro Val Arg Val Asn Glu Gln Arg Val Ser Asn
450                 455                 460

Leu Leu Gln Ser Val Leu Val Gly Leu Leu Ile Leu Ala Val Pro Val
465                 470                 475                 480

Leu Arg Met Ile Pro Thr Ser Val Leu Trp Gly Tyr Phe Thr Tyr Met
                485                 490                 495

Ala Val Asp Ser Leu Pro Gly Asn Gln Phe Trp Glu Arg Leu Gln Leu
                500                 505                 510

Leu Phe Ile Thr Pro Gly Arg Arg Phe Lys Val Leu Glu Gly Leu His
                515                 520                 525

Ala Ser Phe Val Glu Ile Val Pro Tyr Lys Ser Ile Val Met Phe Thr
530                 535                 540

Leu Phe Gln Leu Leu Tyr Phe Leu Ile Cys Tyr Gly Val Thr Trp Ile
545                 550                 555                 560

Pro Val Gly Gly Ile Leu Phe Pro Leu Pro Phe Phe Ile Leu Ile Ala
                565                 570                 575

Leu Arg Gln Tyr Ile Leu Gln Arg Leu Phe Asp Pro Ser His Leu Gln
                580                 585                 590

Val Leu Asp Ser Ser Glu Tyr Glu Glu Met Val Gly Ala Pro Gln Arg
                595                 600                 605

Asn Ser Ser Phe Gly Phe Asn Gly Glu Leu Arg Glu Ala His Asn Ile
610                 615                 620

Pro Leu Ser Val Val Glu Asn Ser Glu Asp Glu Phe Tyr Asp Ala Glu
625                 630                 635                 640

Ile Leu Asp Glu Ile Thr Thr Ser Arg Gly Glu Leu Lys His Arg Thr
                645                 650                 655

Leu Ser Val Lys Glu Asp Arg Ser Gln Met Val Lys Ile Tyr Asn His
                660                 665                 670

Ser
```